US006891006B2

(12) United States Patent
Hessen et al.

(10) Patent No.: US 6,891,006 B2
(45) Date of Patent: May 10, 2005

(54) YTTRIUM-BASED ETHYLENE POLYMERIZATION CATALYSTS WITH BULKY AMIDINATE ANCILLARY LIGANDS

(75) Inventors: Bart Hessen, Noordwijk (NL); Sergio De Araujo Bambirra, Groningen (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 35 days.

(21) Appl. No.: 10/465,477

(22) Filed: Jun. 19, 2003

(65) Prior Publication Data

US 2004/0033889 A1 Feb. 19, 2004

Related U.S. Application Data

(60) Provisional application No. 60/390,618, filed on Jun. 21, 2002.

(51) Int. Cl.$^7$ .................................................. C08F 4/44
(52) U.S. Cl. ....................... 526/164; 526/172; 526/160; 526/170; 502/104; 502/103
(58) Field of Search ................................ 526/172, 170, 526/161, 160, 164; 502/203, 204

(56) References Cited

U.S. PATENT DOCUMENTS

| | | | | |
|---|---|---|---|---|
| 5,318,935 | A | * | 6/1994 | Canich et al. ............... 502/117 |
| 5,502,128 | A | * | 3/1996 | Flores et al. ................ 526/160 |
| 5,707,913 | A | * | 1/1998 | Schlund et al. ............. 502/102 |
| 5,723,399 | A | * | 3/1998 | Takemoto et al. ........... 502/113 |
| 6,218,489 | B1 | * | 4/2001 | Riedel et al. ................ 526/161 |
| 6,262,198 | B1 | * | 7/2001 | Schlund et al. ............. 526/127 |
| 6,284,697 | B1 | * | 9/2001 | Windisch et al. ........... 502/102 |
| 6,303,714 | B1 | * | 10/2001 | Kibino et al. ................ 526/116 |
| 6,579,998 | B2 | * | 6/2003 | Sita et al. ..................... 556/53 |
| 6,627,574 | B2 | * | 9/2003 | Eisen et al. .................. 502/155 |

FOREIGN PATENT DOCUMENTS

| | | |
|---|---|---|
| EP | 0687693 | 6/1995 |
| WO | 99/05154 | 2/1999 |
| WO | 00/12568 | 3/2000 |

OTHER PUBLICATIONS

Bambirra et al. Organometallics 2000, 19, 3197–3204.*
Aubrecht et al. J. Poly, Sci. A: Polym. Chem. 2001, 39, 284–293.*
Duchateau et al. J. Am. Chem. Soc. 1993, 115, 4931–4932.*
Duchateau et al. Organometallics 1996, 15, 1656–1661.*
Littke et al. Organometallics 1998, 17, 446–451.*
D. H. McConville et al., *Polymerization of α–Olefins by Chelating Diamide Complexes of Titanium*, Macromolecules 1996, 29, 5241–5243.
Robbert Duchateau, Cornelis T. van Wee and Jan H. Teuben, *Insertion and C–H Bond Activation of Unsaturated Substrates by Bis (benzamidinato)ytrium Alkyl, [PhC(NSiMe$_3$)$_2$]$_2$YR(R=CH$_2$Ph·THF, CH(SiMe$_3$)$_2$), and Hydrido, {[PhC(N-SiMe$_3$)$_2$]$_2$Y (μ–H)}$_2$, Compounds*, 1996, Organometallics, 15, 2291–2302.
Katherine B. Aubrecht, Karen Chang, Marc A. Hillmyer, William B. Tolman, *Lactide Polymerization Activity of Alkoxide, Phenoxide, and Amide Derivatives of Yttrium (III) Arylamidinates*, Journal of Polymer Science, Part A: Polymer Chemistry 92000), 2001 39(2), 284–293.

* cited by examiner

*Primary Examiner*—David W. Wu
*Assistant Examiner*—Rip A Lee

(57) ABSTRACT

A cationic Group 3 or Lanthanide metal complex for coordination polymerization of olefins is disclosed. The precursor metal complex is stabilized by an anionic amidinate ancillary ligand. Upon reaction with an activator, the complex becomes an active olefin-polymerization catalyst. Some invention processes give narrow polymer polydispersities.

33 Claims, No Drawings

YTTRIUM-BASED ETHYLENE POLYMERIZATION CATALYSTS WITH BULKY AMIDINATE ANCILLARY LIGANDS

CROSS REFERENCE TO RELATED APPLICATIONS

This application claims the benefit of Provisional Application No. 60/390,618 filed Jun. 21, 2002.

FIELD

This invention relates to certain transition metal compounds from Group 3 of the Periodic Table of Elements and from the lanthanides, and to a catalyst system comprising Group-3 or Lanthanide transition metal compounds and alumoxane, modified alumoxane, non-coordinating anion activator, Lewis acid, or the like to form active cationic catalyst species for the production of polyolefins such as polyethylene, polypropylene and alpha-olefin copolymers of ethylene and propylene having a high molecular weight.

BACKGROUND

Ancillary ligand stabilized metal complexes (e.g., organometallic complexes) are useful as catalysts, additives, stoichiometric reagents, monomers, solid state precursors, therapeutic reagents, and drugs. The ancillary ligand system comprises organic substituents that bind to the metal centers, remain associated with the metal centers, and therefore, provide an opportunity to modify the shape and electronic and chemical properties of the active metal center(s) of the organometallic complex's active metal centers.

Certain organometallic complexes are catalysts for reactions such as oxidation, reduction, hydrogenation, hydrosilation, hydrocyanation, hydroformylation, polymerization, carbonylation, isomerization, metathesis, carbon-hydrogen activation, cross-coupling, Friedel-Crafts acylation and alkylation, hydration, dimerization, trimerization, oligomerization, Diels-Alder reactions, and other transformations. Organometallic complexes can be prepared by combining an ancillary ligand precursor with a suitable metal-containing precursor in a suitable solvent at a suitable temperature. For example, organometallic complexes are used for single-site, olefin polymerization catalysis. The active site typically comprises an ancillary-ligand-stabilized, coordinatively unsaturated, transition metal, alkyl complex.

PCT publication WO 99/05154 relates to a variety of pnictide-based ligands and their uses for catalyst systems. In particular, it discloses metal compositions and compounds, having an ancillary ligand structure, that polymerize non-functionalized and functionalized monomers, either alone or in the presence of an activator. The ancillary ligand structure is a chelating ligand that may optionally further connect to the metal.

Amidinato complexes of Group-3–6 metals are disclosed in U.S. Pat. No. 5,707,913 to Schlund et al. Group-4 bisamido catalysts are disclosed in U.S. Pat. No. 5,318,935 to Canich, et al., and related multidentate, bisarylamido catalysts are disclosed by D. H. McConville et al. *Macromolecules* 1996, 29, 5241–5243.

It is always a desire to discover new catalysts and catalyst systems as provided by these compositions and catalyst systems.

SUMMARY

One aspect of the invention relates to catalyst precursors useful as a catalyst after activation. The catalyst comprises the reaction product of an activator and a transition metal coordination complex with a Group-3 or lanthanide metal. At least one amidinate or phosphoamidinate ligand, with a central carbon atom connected between the nitrogen or phosphorus atoms connects to the metal. The ligand also has at least one adjuvant moiety connected to each nitrogen or phosphorus atom, where the adjuvant moiety comprises a substituted aryl group with at least two side groups. The side groups are independently methyl, isopropyl, cyclohexyl, phenyl, or tertiary butyl groups. These side groups may be chosen from fluoride, chloride, bromide, iodide and alkoxide, as well. They connect to the aryl group at the two positions adjacent to the aryl-nitrogen or aryl-phosphorus connection. Additionally, the metal complex has an apical substituent that connects to the central carbon atom. The metal may connect to zero or more Lewis bases. The apical substituents are, independently, $C_1$–$C_{30}$, substituted or unsubstituted, hydrocarbyl radicals. The complex has at least two other ligands: one abstractable by a cocatalyst; and one that allows for olefin insertion between it and the transition metal.

DEFINITIONS

Catalyst systems encompass a catalyst precursor/activator pair. When catalyst system is used to describe such a pair before activation, it means the unactivated catalyst together with the activator. When catalyst system is used to describe such a pair after activation, it means the activated catalyst and a non-coordinating anion (NCA) or other charge-balancing moiety that in most cases was part of the activator before activation. For purposes of this disclosure, an activator is any compound that can remove a ligand from the catalyst precursor under polymerization conditions.

Feedstocks are any desired mixture of ethylene, $C_3$–$C_{20}$ α-olefins, $C_4$–$C_{20}$ diolefins, acetylenically unsaturated monomers, or other unsaturated monomers. These feedstocks predominately contain one monomer for homopolymerization reactions; for copolymerization reactions, they contain two-or-more monomer mixtures.

Amidine represents a polyhapto-coordinating ligand that comprises at least a nitrogen-carbon-nitrogen linkage as shown below:

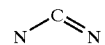

Phosphoamidines are amidines in which one or both nitrogen atoms have been replaced by phosphorous atoms. When ionized to their anionic form, the amidine and the phosphoamidine are called amidinates and phosphoamidinates, respectively. See the formula set out below for an amidinate. These moities form the backbone of the invention ancillary ligand Ancillary ligands serve to enforce the geometry around the metal center.

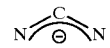

L' represents a neutral Lewis base: diethyl ether, tetrahydrofuran, dimethylaniline, trimethylphosphine, lithium chloride, or the like. It coordinates to the metal. It also optionally binds to one or both X, with an appropriate X. L' can also be a second transition metal complex of the same type as the first metal complex thereby creating a dimeric catalyst or catalyst precursor (if both transition metals are the same) or a bimetallic catalyst or catalyst precursor (if not). 'w' represents the number of L connected to the complex and is 0–2.

An adjuvant ligand is an aryl group substituted with two side groups such as methyl, isopropyl, phenyl, cyclohexyl, or tertiary butyl groups. It connects to a phosphorus or nitrogen on the amidinate or phosphoamidinate ancillary ligand, and thus, it affects the metal complex's catalytic behavior.

Noncoordinating anion (NCA) is art recognized to mean an anion either that does not coordinate to the metal cation or that does coordinate to the metal cation, but only weakly. An NCA coordinates weakly enough that a neutral Lewis base, such as an olefinically or acetylenically unsaturated monomer, can displace it. Any metal or metalloid that can form a compatible, weakly or negligibly coordinating complex may be used or contained in the noncoordinating anion. Suitable metals include, but are not limited to, aluminum, gold, and platinum. Suitable metalloids include, but are not limited to, boron, aluminum, phosphorus, and silicon.

The term "hydrocarbyl radical" is sometimes used interchangeably with "hydrocarbyl" throughout this document. For purposes of this disclosure, "hydrocarbyl radical" encompasses all $C_1$–$C_{50}$ radicals. They can be linear, branched, or cyclic, and when cyclic, aromatic or non-aromatic. The term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which one or more hydrogen atoms have been substituted with one or more functional groups such as $NR''_2$, $OR''$, $PR''_2$, $SR''$, $BR_2''$, $SiR''_3$, $GeR''_3$ and the like or where a non-hydrocarbon atom or group has been inserted within the hydrocarbyl radical, such as O, S, $NR''$, $PR''$, $BR''$, $SiR''_2$, $GeR''_2$ and the like, where $R''$ is independently a hydrocarbyl or halocarbyl radical.

Halocarbyl radicals are radicals in which one or more hydrocarbyl hydrogen atoms have been substituted with a halogen or halogen-containing group (e.g. F, Cl, Br, I).

Substituted halocarbyl radicals are radicals in which one or more hydrocarbyl hydrogen or halogen atoms have been substituted with one or more functional groups such as $NR''_2$, $OR''$, $PR''_2$, $SR''$, $BR_2''$, $SiR''_3$, $GeR''_3$ and the like or where a non-carbon atom or group has been inserted within the halocarbyl radical such as O, S, $NR''$, $PR''$, $BR''$, $SiR''_2$, $GeR''_2$ and the like where $R''$ is independently a hydrocarbyl or halocarbyl radical provided that at least one halogen atom remains on the original halocarbyl radical.

In some embodiments, the hydrocarbyl radical is independently selected from a propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomer. The radical may then be subjected to the types of substitutions described above.

When a hydrocarbyl radical is referred to by name, such as butyl, it encompasses all radical isomers containing the specified number of carbon atoms (four for butyl) including radicals that are unsubstituted or that have been subjected to the types of substitution described above. According to this naming scheme, butyl, therefore includes but is not limited to, n-butyl, t-butyl, i-butyl, 2-methylpropyl, chlorobutyl, perfluorobutyl, etc. Similarly, phenyl includes phenyl, perfluorophenyl, 2-methylphenyl, 2,4, dibromophenyl, etc.

Polymerization encompasses any reaction such as homopolymerization and copolymerization. It encompasses production of homopolymers and of copolymers with other α-olefin, α-olefinic diolefin, or non-conjugated diolefin monomers, for example $C_3$–$C_{20}$ olefins, $C_4$–$C_{20}$ diolefins, $C_4$–$C_{20}$ cyclic olefins, or $C_8$–$C_{20}$ styrenic olefins. Other olefinically unsaturated monomers besides those specifically described above may be polymerized using the invention catalysts, for example, styrene, alkyl-substituted styrene, ethylidene norbornene, norbornadiene, dicyclopentadiene, vinylcyclohexane, vinylcyclohexene, and other olefinically-unsaturated monomers, including other cyclic olefins, such as cyclopentene, norbornene, and alkyl-substituted norbornenes. Copolymerization reactions can also incorporate α-olefinic macromonomers of up to 2000 mer units.

Q are abstractable ligands or leaving groups and olefin insertion ligands connected to the metal center. Usually, activation occurs when one or more Q is removed from the metal. Also, one or more Q remains and, as part of the polymerization process, olefin monomer inserts into the metal-center-Q bond. Thus, a constraint on Q is that olefin monomer should be able to insert between it and the metal center. Alternatively, in cases in which Q cannot accommodate an olefin insertion, Q should be a ligand that can be readily exchanged for a ligand into which an olefin can insert.

Qs are univalent anionic ligands including halide ligands and substituted or unsubstituted hydrocarbyl ligands. Qs independently include, but are not limited to, monoanionic, hydride, hydrocarbyl, alkoxide, aryloxide, amide, or phosphide radicals. Furthermore, both Q together may be an alkylidene, a cyclometallated hydrocarbyl, or any other divalent anionic chelating ligand, or Q can be a diene. Exemplary Q in the formulas are methyl, ethyl propyl, butyl, pentyl, isopentyl, neopentyl, hexyl, isobutyl, heptyl, octyl, nonyl, decyl, cetyl, 2-ethylhexyl, phenyl, benzyl, trimethylsilylmethyl, triethylsilylmethyl and the like. Some embodiments limit at least one Q to trimethylsilylmethyl. Exemplary halogen atoms for Q include chlorine, bromine, and iodine. Some embodiments select Q as chlorine. Exemplary alkoxides and aryloxides for Q are methoxide, phenoxide and substituted phenoxides such as 4-methylphenoxide. Exemplary amides for Q are dimethylamide, diethylamide, methylethylamide, di-t-butylamide, diisopropylamide, and the like. Exemplary arylamides are diphenylamide and any other substituted phenylamides. Exemplary phosphides for Q are diphenylphosphide, dicyclohexylphosphide, diethylphosphide, dimethylphosphide, and the like. Exemplary alkylidene radicals for both Q together are methylidene, ethylidene, and propylidene. Exemplary cyclometallated hydrocarbyl radicals for both Q together are propylene, and isomers of butylene, pentylene, hexylene, and octylene. Exemplary dienes for both Q together are 1,3-butadiene, 1,3-pentadiene, 1,4-pentadiene, 1,3-hexadiene, 1,4-hexadiene, 1,5-hexadiene, 2,4-dimethyl-1,3-butadiene, 2-methyl-1,3- pentadiene, 2-methyl-1,3-hexadiene, and 2,4-hexadiene. Qs can also be simple alkyl ligands substituted with at least one trialkyl silyl group. Some embodiments select Q as $CH_2SiMe_3$, $CH_2CMe_3$, $CH_2CMe_2Ph$, $CH_2CHMe_2$, $CH_3$, $CH_2CH_3$, Cl, Br, and OiPr, OPh, $NMe_2$, and $N(iPr)_2$.

R is a $C_1$–$C_{30}$ hydrocarbyl radical (some embodiments select R as a bulky hydrocarbyl radical such as isopropyl). Suitable R include, but are not limited to, methyl, ethyl, propyl, cyclohexyl, phenyl, butyl, 2,2-dimethylethyl, dimethylphenylmethyl, methyldiphenylmethyl, trifluoromethyl, 2,6-dichlorophenyl, fluoro, chloro, bromo, methoxy, and dimethylamino. R is sometimes referred to as a side group.

R' is a hydrogen or a $C_1$–$C_{30}$ hydrocarbyl radical. Throughout this specification R' is sometimes referred to as a second R group. Suitable R' include, but are not limited to, hydrogen, methyl, ethyl, propyl, cyclohexyl, phenyl, butyl, 2,2-dimethylethyl, dimethylphenylmethyl, methyldiphenylmethyl, trifluoromethyl, 2,6-dichlorophenyl, fluoro, chloro, bromo, methoxy, dimethylamino, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$, $C_{20}H_{41}$, and $C_{21}H_{43}$.

R" is a $C_1$–$C_{30}$ hydrocarbyl radical (some embodiments select a bulky hydrocarbyl radical such as phenyl or perfluorophenyl). Suitable R" include, but are not limited to, hydrogen, methyl, ethyl, propyl, cyclohexyl, phenyl, butyl, 2,2-dimethylethyl, dimethylphenylmethyl, methyldiphenylmethyl, trifluoromethyl, 2,6-dichlorophenyl, fluoro, chloro, bromo, methoxy, dimethylamino, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $C_{18}H_{37}$, $C_{19}H_{39}$, $C_{20}H_{41}$, and $C_{21}H_{43}$.

Throughout this specification R" is sometimes referred to as an apical substituent.

Pn represents a pnictide, a Group-15 element. For purposes of this disclosure, pnictide is limited to nitrogen, phosphorus and arsenic.

DETAILED DESCRIPTION

In part, the current invention encompasses the use of a sterically encumbered benzamidinate ancillary ligand to prepare a mono(amidinate) yttrium dialkyl that, with a Bronsted acid activator, such as $[PhNMe_2H][B(C_6F_5)_4]$, can be converted into a cationic monoalkyl species that is active for ethylene polymerization. The polyethylenes produced with these catalysts have narrow polydispersities. In this case, narrow polydispersity means that polymer produced by invention catalysts have polydispersities lower than polymer produced by Ziegler-Natta catalysts. In some cases, polymer produced by invention catalysts have polydispersities less than two.

Thus, a useful catalyst precursor for invention catalyst systems has the following formula:

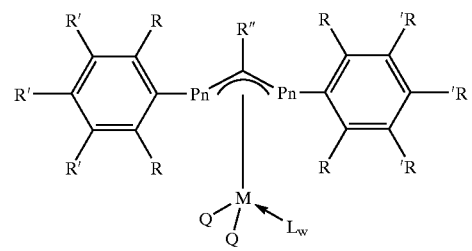

M is a Group-3 or lanthanide transition metal. Pn is pnictogen. And R, R', R", Q, L, and w are defined above.

The sterically demanding amidine ArN=CPhNHAr may be prepared from benzoic acid and the corresponding aniline using silylated polyphosphoric acid following the method described in the literature. S. Ogata, A. Mochizuki, M. -A. Kakimoto and Y. Imai, *Bull. Chem. Soc. Jpn.*, 1986, 59, 2171. This ligand can also be prepared in a stepwise fashion through the corresponding imidyl chloride, as reported by R. T. Boeré, V. Klassen and G. Wolmershäuser, *J. Chem. Soc., Dalton Trans.*, 1998, 4147.

The amidine reacts cleanly in benzene with $Y(CH_2SiMe_3)_3(THF)_2$ to give $SiMe_4$ and the amidinate yttrium dialkyl species. ($Y(CH_2SiMe_3)_3(THF)_2$ is described in: M. F. Lappert and R. Pearce, *J. Chem. Soc., Chem. Commun.*, 1973, 126.) Performing the reaction in pentane, followed by evaporation of the solvent and removal of residual THF from the material by stirring with additional pentane eventually allowed crystallization of the dialkyl complex as a mono-THF adduct:

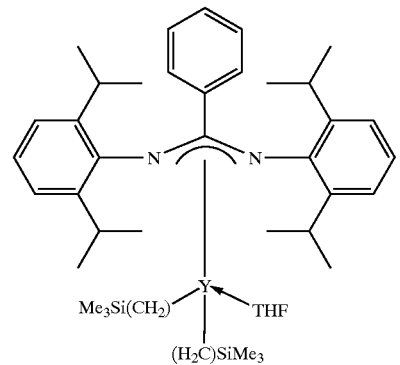

Reaction mixture workup by concentrating and cooling the initially formed solution cleanly yields crystals of the bis-THF adduct. Both of these yttrium complexes are characterized by single crystal X-ray diffraction.

Invention metal complexes (catalyst precursors) catalyze olefin polymerization when activated by methods known in the metallocene art. In cases such as those of the instant inventions, after ligand abstraction to generate the cationic catalyst, an additional Lewis acid activator is sometimes used to remove an additional Lewis base from the catalyst. Suitable activators typically include alumoxane compounds, modified alumoxane compounds, and ionizing anion precursor compounds that abstract one metal ligand making the metal complex cationic and providing a charge-balancing noncoordinating or weakly coordinating anion. When using ionizing anion precursor compounds alone, some embodiments limit Q to hydride, hydrocarbyl, and substituted hydrocarbyl radicals, including organometalloid-substituted hydrocarbyl radicals.

Alkylalumoxanes and modified alkylalumoxanes are suitable as catalyst activators, particularly when the abstractable ligand is a halide, alkoxide, or amide. Mixtures of different alumoxanes and modified alumoxanes may also be used. For further descriptions, see U.S. Pat. Nos. 4,665,208, 4,952, 540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator to be a 5000-fold molar excess over the catalyst precursor (per metal catalytic site). The minimum activator-to-catalyst-precursor ratio is a 1:1 molar ratio.

Descriptions of ionic catalysts with a transition-metal cationic complex and a noncoordinating anion, suitable for polymerization appear in U.S. Pat. Nos. 5,064,802, 5,132, 380, 5,198,401, 5,278,119, 5,321,106, 5,347,024, 5,408,017, 5,599,671, and WO 92/00333 and WO 93/14132. These teach a preparation method in which metallocenes are protonated by noncoordinating anion precursors such that a substituted or unsubstituted alkyl or hydride group (denoted Q in this disclosure) is abstracted from the transition metal compound making it both cationic and charge-balanced by the noncoordinating anion. Since similar ligands may be present in this invention's catalyst precursors, similar polymerization-catalyst activation methods may be followed.

Using ionic compounds lacking an active proton, but capable of producing both an active metal cationic complex and a noncoordinating anion, is also possible. See, EP-A-0 426 637, EP-A-0 573 403 and U.S. Pat. No. 5,387,568 for illustrative ionic compounds. Reactive cations other than Bronsted acids, include ferrocenium, silver, tropylium, triphenylcarbenium, and triethylsilylium, and alkali and alkaline earth metal cations such as sodium, magnesium, or lithium cations. A further class of suitable noncoordinating anion precursors contains hydrated salts of alkali- or alkaline-earth-metal cations and a non-coordinating anion as described above. The hydrated salts are made by reacting the metal-cation/noncoordinating-anion salt with water, for example, by hydrolysis of the commercially available or readily synthesized $[Li]^+[B(pfp)_4]^-$, which yields $[Li(H_2O)_x]^+[B(pfp)_4]^-$: pfp is pentafluorophenyl or perfluorophenyl.

An additional method of making active invention polymerization catalysts uses ionizing anion precursors that are initially neutral Lewis acids but form a cationic metal complex and a noncoordinating anion or a zwitterionic complex upon reaction with invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486, 632; and 5,527,929.

When the cations of noncoordinating anion precursors are Bronsted acids such as protons or protonated Lewis bases (excluding water), or reducible Lewis acids such as ferrocenium or silver cations, or alkali- or alkaline-earth-metal cations such as those of sodium, magnesium, or lithium, the catalyst-precursor-to-activator molar ratio may be any ratio. Combinations of the described activator compounds may also be used for activation. For example, tris (perfluorophenyl) boron can be used in conjunction with methylalumoxane.

Invention catalyst complexes are useful in polymerizing unsaturated monomers conventionally known to undergo metallocene-catalyzed polymerization such as solution, slurry, gas-phase, and high-pressure polymerization. These catalysts may be supported and as such will be particularly useful in the known, fixed-bed, moving-bed, fluid-bed, slurry, or solution operating modes conducted in single, series, or parallel reactors.

Those of ordinary skill in the art are well versed in preparing supported catalyst systems. For instance, the activator can be added to the support followed by adding the catalyst or catalyst mixture; the catalyst or catalyst mixture can be added to the support followed by adding the activator; or both the activator and catalyst or catalyst mixture can be added substantially simultaneously. Other methods and order of addition will be apparent to those skilled in the art.

Generally, when using invention catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization without using some scavenging compounds. Normally, the polymerization process will still use at least small amounts of scavenging compounds.

Typically, the scavenging compound will be an organometallic compound such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and tri-n-octyl aluminum. Those scavenging compounds having bulky or $C_6$–$C_{20}$ linear hydrocarbyl substituents connected to the metal or metalloid center usually minimize adverse interaction with the active catalyst. Examples include triethylaluminum, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$.

The invention catalysts can be supported for gas-phase, bulk, or slurry polymerization use, or otherwise as needed. Numerous support methods are known for catalysts in the olefin copolymerization art, particularly alumoxane-activated catalysts; any are suitable for this invention's broadest practice. See, for example, U.S. Pat. Nos. 5,057, 475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Varying embodiments employ the catalyst system in the liquid phase (solution, slurry, suspension, bulk phase, or suitable combinations); in high-pressure, liquid, or supercritical fluid phases; or in the gas phase. Each may be employed in singular, parallel, or series reactors. The liquid processes comprise contacting olefin monomers with the catalyst system described above. The reaction runs in a suitable diluent or solvent long enough to produce invention polymers. Both aliphatic and aromatic hydrocarbyl solvents are suitable; some embodiments select hexane or toluene. Typically, in bulk and slurry processes, the liquid monomer slurry contacts the supported catalysts. Gas-phase processes typically use a supported catalyst and are conducted in any suitable manner for ethylene homo- or copolymerization. Illustrative examples may be found in U.S. Pat. Nos. 4,543, 399, 4,588,790, 5,028,670, 5,382,638, 5352,749, 5,436,304, 5,453,471, 5,463,999, and WO 95/07942.

Polymerization reaction temperatures can vary. The minimum reaction temperature is $-50°$ C.; in some embodiments, the minimum is $-20°$ C. The maximum temperature is $250°$ C.; some embodiments select the reaction temperature to be at or below $200°$ C. Some embodiments select from the following temperature ranges: $-50$ to $250°$ C.; $-50$ to $200°$ C.; $-20$ to $250°$; and $-20$ to $200°$ C.

Linear polyethylene, including high- and ultra-high-molecular-weight polyethylenes are produced by adding ethylene, and optionally one or more other monomers, to a reaction vessel with an invention catalyst. The invention catalyst is first slurried with or dissolved in a solvent, such as hexane or toluene. Gas-phase polymerization can be conducted, for example, in a continuous, fluidized-bed, gas-phase reactor operated between 200–3000 kPa and at 60–160° C., using hydrogen as a reaction modifier (100–200 ppm), a $C_4$–$C_8$ comonomer feedstream (0.5–12 mol %), a $C_2$ feedstream (25–35 mol %), and a supported catalyst. See, U.S. Pat. Nos. 4,543,399; 4,588,790; 5,028,670; 5,405,922; and 5,462,999.

Ethylene-α-olefin (including ethylene-cyclic olefin and ethylene-α-olefin-diolefin) elastomers of high molecular weight and low crystallinity can be prepared using invention catalysts under traditional solution polymerization conditions or by introducing ethylene gas into a slurry of polymerization diluent and catalyst. The polymerization diluent contains α-olefin monomers, cyclic olefin monomers, or their mixtures with other polymerizable and non-polymerizable monomers. In this case, polymerization reaction pressure varies, as well. The minimum pressure is 0.00013 MPa; a pressure of at least 0.01 MPa sometimes selected. The reaction pressure is usually at least 0.1 MPa. The maximum pressure is 250 MPa. Some embodiments select the maximum pressure to be 160 or 50 MPa. Thus, different embodiments select pressure ranges from the following: 0.00013 to 160 MPa; 0.00013 to 250 MPa; 0.00013 to 50 MPa; 0.01 to 160 MPa; 0.01 to 250 MPa; 0.01 to 50 MPa; 0.1 to 160 MPa; 0.1 to 250 MPa; 0.1 to 50 MPa. Typical ethylene pressures will be between 10 and 1000 psig (69–6895 kPa) and the polymerization diluent temperature will typically be between $-10$ and $160°$ C. The process can use a stirred-tank reactor, or more than one reactor operated in series or parallel. See the general disclosure of U.S. Pat. No. 5,001,205.

Slurry or gas-phase reaction processes can use pre-polymerized supported invention catalyst to further control polymer particle morphology, as is known in the art. For example, such reaction can be accomplished by pre-polymerizing a $C_2$–$C_6$ α-olefin for a limited time. Ethylene contacts the supported catalyst at between $-15°$ to $30°$ C. and ethylene pressure of up to 250 psig (1724 kPa) for 75 min to obtain a polyethylene coating on the support (30,000–150,000 molecular weight). The above polymerization process can then use the pre-polymerized catalyst. Additionally, polymeric resins may be used as a support coating, typically by suspending a support in dissolved polystyrene resin or similar material followed by separation and drying.

The invention catalyst compositions can be used individually as described above or can be mixed together or with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

Suitable catalyst precursor compounds for use in the mixed catayst embodiments of this invention include the known organometallic, transition metal compounds useful for traditional Ziegler-Natta polymerization, particularly the metallocenes known to be useful in polymerization. Useful catalyst precursors include Group-3–10 transition metal compounds in which at least one metal ligand can be abstracted by an activator. Particularly, those abstractable ligands include hydride, hydrocarbyl, hydrocarbylsilyl, and their lower-alkyl-substituted ($C_1$–$C_{10}$) derivatives. Examples include hydride, methyl, benzyl, dimethylbutadiene, etc. Abstractable ligands and transition metal compounds comprising them include those metallocenes described in, for example, U.S. Pat. No. 5,198,401 and WO 92/00333. Additionally, in those cases where the metal ligands include labile halogen, amido, or alkoxy ligands (for example, biscyclopentadienyl zirconium dichloride), which may not allow for ready abstraction by invention's cocatalysts, the ligands can be replaced with abstractable ones. This replacement uses known routes such as alkylation with lithium or aluminum hydrides, alkyls, alkylalumoxanes, Grignard reagents, etc. See also EP 0 500 944 and EP 0 570 982 for the reaction of organoaluminum compounds with dihalo-substituted metallocenes prior to catalyst activation.

Additional descriptions of metallocene compounds, useful in the mixed-catalyst embodiments of the current invention, with, or that can be alkylated to contain, at least one ligand abstractable to form catalytically active transition-metal cations appear in the patent literature. (E.g., EP-A-0 129 368, U.S. Pat. Nos. 4,871,705, 4,937,299, 5,324,800, 5,470,993, 5,491,246, 5,512,693, EP-A-0 418 044, EP-A-0 591 756, WO-A-92/00333, WO-A-94/01471 and WO 97/22635.) Such metallocenes can be described as mono- or biscyclopentadienyl-substituted Group-3, -4, -5, or -6 transition metals. The transition metal ligands may themselves be substituted with one or more groups, and the ligands may bridge to each other or bridge through a heteroatom to the transition metal. The size and constituency of the ligands and bridging elements should be chosen in the literature-described manner to enhance activity and to select desired characteristics. Embodiments in which the cyclopentadienyl rings (including substituted, cyclopentadienyl-based, fused-ring systems, such as indenyl, fluorenyl, azulenyl, or their substituted analogs), when bridged to each other, are lower-alkyl substituted ($C_1$–$C_6$) in the 2 position (with or without a similar 4-position substituent in the fused ring are useful). The cyclopentadienyl rings may additionally comprise alkyl, cycloalkyl, aryl, alkylaryl, and arylalkyl substituents, the latter as linear, branched, or cyclic structures including multi-ring structures, for example, those of U.S. Pat. Nos. 5,278,264 and 5,304,614. In some embodiments, such substituents should each have essentially hydrocarbyl characteristics and will typically contain up to 30 carbon atoms, but may contain heteroatoms, such as 1 to 5 non-hydrogen or non-carbon atoms, e.g., N, S, O, P, Ge, B and Si.

The mixed-catalyst embodiments of the current invention can employ essentially all known metallocene catalyst that are suitable for preparing polyolefins from $C_2$–$C_{10}$ α-olefin monomer or mixtures of monomers, see again WO-A-92/00333 and U.S. Pat. Nos. 5,001,205, 5,198,401, 5,324,800, 5,304,614 and 5,308,816, for specific listings. Criteria for selecting suitable metallocene catalysts for making polyethylene and polypropylene are well known in the art, in both patent and academic literature, see for example *Journal of Organometallic Chemistry* 369, 359–370 (1989). Likewise, methods for preparing these metallocenes are also known. Typically, the catalysts are stereorigid, asymmetric, chiral, or bridged-chiral metallocenes. See, for example, U.S. Pat. Nos. 4,892,851, 5,017,714, 5,296,434, 5,278,264, WO-A-(PCT/US92/10066) WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al, *Organometallics* 1994, 13, 964–970, and documents referred to therein.

Representative metallocene compounds useful in the mixed-catalyst embodiments of the current invention can have the formula:

where Mc is a Group-3–10 metal; $L_A$ is a substituted or unsubstituted, cyclopentadienyl or heterocyclopentadienyl ligand connected to Mc; and $L_B$ is a ligand as defined for $L_A$, or is J, a heteroatom ligand connected to Mc. $L_A$ and $L_B$ may connect to each other through a Group-13-to-16-element-containing bridge. $L_{Ci}$ is an optional, neutral, non-oxidizing ligand connected to Mc (i equals 0 to 3); and D and E are the same or different labile ligands, optionally bridged to each other, $L_A$, or $L_B$. Each of D and E are connected to Mc. Some embodiments select Mc to be a member of the Group-3–6 transition metals. Other embodiments select Mc to be a Group-4 transition metal. Some embodiments select Mc to be Ti, Zr, or Hf.

D and E's identity is functionally constrained. The first constraint is that upon activation, either the D—Mc or the E—Mc connection must break. D and E should be chosen to facilitate this. Another constraint is that a polymerizable molecule must be able to insert between Mc and whichever of D or E remains.

Cyclopentadienyl and heterocyclopentadienyl ligands encompass fused-ring systems including but not limited to indenyl and fluorenyl radicals. Also, the use of heteroatom-containing rings or fused rings, where a non-carbon, Group-13, -14, -15, or -16 atom replaces a ring carbon is within the term "cyclopentadienyl" for this specification. See, for example, the background and illustrations of WO 98/37106, having priority with U.S. Ser. No. 08/999,214, filed Dec. 29, 1997, and WO 98/41530, having priority with U.S. Ser. No. 09/042,378, filed Mar. 13, 1998. Substituted cyclopentadienyl structures are structures in which one or more hydrogen atoms are replaced by a hydrocarbyl, hydrocarbylsilyl, or similar heteroatom-containing structure. Hydrocarbyl structures specifically include $C_1$–$C_{30}$ linear, branched, and cyclic alkyl, and aromatic fused and pendant rings. These rings may also be substituted with ring structures.

Catalyst precursors useful in the mixed-catalyst embodiments of the current invention also include the mono- and biscyclopentadienyl compounds such as those listed and described in U.S. Pat. Nos. 5,017,714, 5,324,800, WO 92/00333 and EP-A-0 591 756.

Bis amide catalyst precursors are also useful in the mixed-catalyst embodiments of the current invention. Bisamide catalyst precursors are those precursors that have the following formula:

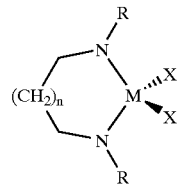

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the bisamide catalyst precursor must first be chemically modified to transform X into an abstractable ligand. This can be done by alkylation, for example.

Pyridine bisamide catalyst precursors are also useful in the mixed-catalyst embodiments of the current invention. Pyridine bisamide catalyst precursors are those precursors that have the following formula:

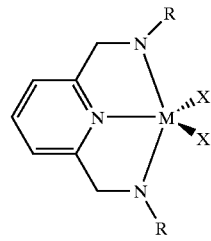

M is Ti, Zr, or Hf. R are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the pyridine bisamide catalyst precursor must first be chemically modified to transform X into an abstractable ligand. This can be done by alkylation, for example.

Amine bisamide catalyst precursors are also useful with invention cocatalysts. Amine bisamide catalyst precursors are those precursors that have the following formula:

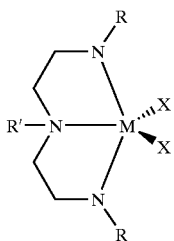

M is Ti, Zr, or Hf. R and R' are the same or different alkyls, aryls, substituted alkyl, or substituted aryls. X are the same or different alkyls, aryls, or halides.

Substituted alkyl and aryls can be alkyl-, aryl-, and halo-substituted. When X is a halide, the amine bisamide catalyst precursor must first be chemically modified to transform X into an abstractable ligand. This can be done by alkylation, for example.

Additional exemplary metallocene-type catalysts useful in the mixed-catalyst embodiments of the current invention include those metallocene compounds represented by the formula:

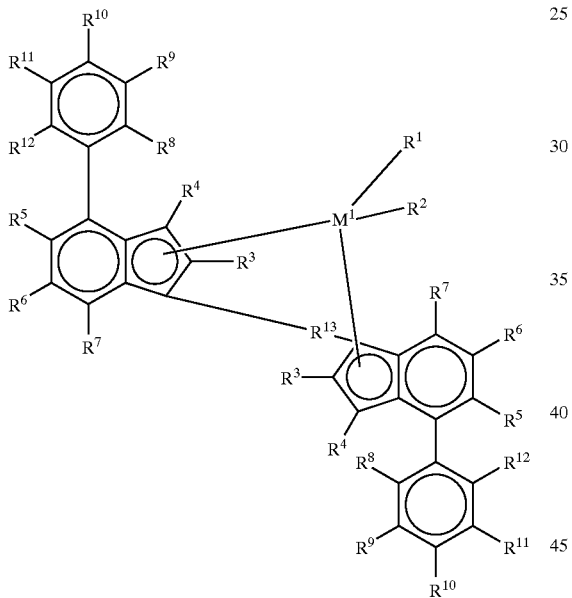

In the above structure, $M^1$ is selected from titanium, zirconium, hafnium, vanadium, niobium, tantalum, chromium, molybdenum, or tungsten.

$R^1$ and $R^2$ are identical or different and are selected from hydrogen atoms, $C_1$–$C_{10}$ alkyl groups, $C_1$–$C_{10}$ alkoxy groups, $C_6$–$C_{10}$ aryl groups, $C_6$–$C_{10}$ aryloxy groups, $C_2$–$C_{10}$ alkenyl groups, $C_2$–$C_{40}$ alkenyl groups, $C_7$–$C_{40}$ arylalkyl groups, $C_7$–$C_{40}$ alkylaryl groups, $C_8$–$C_{40}$ arylalkenyl groups, OH groups or halogen atoms; or conjugated dienes that are optionally substituted with one or more hydrocarbyl, tri(hydrocarbyl)silyl groups or hydrocarbyl, tri(hydrocarbyl) silylhydrocarbyl groups. The conjugated diene can contain up to 30 atoms not counting hydrogen.

$R^3$ are the same or different and are selected from hydrogen atom, halogen atoms, $C_1$–$C_{10}$ halogenated or unhalogenated alkyl groups, $C_6$–$C_{10}$ halogenated or unhalogenated aryl groups, $C_2$–$C_{10}$ halogenated or unhalogenated alkenyl groups, $C_7$–$C_{40}$ halogenated or unhalogenated arylalkyl groups, $C_7$–$C_{40}$ halogenated or unhalogenated alkylaryl groups, $C_8$–$C_{40}$ halogenated or unhalogenated arylalkenyl groups, —$NR'_2$, —$SR'$, —$OR'$, —$OSiR'_3$ or —$PR'_2$ radicals in which R' is one of a halogen atom, a $C_1$–$C_{10}$ alkyl group, or a $C_6$–$C_{10}$ aryl group.

$R^4$ to $R^7$ are the same or different and are hydrogen, as defined for $R^3$ or two or more adjacent radicals $R^5$ to $R^7$ together with the atoms connecting them form one or more rings.

$R^{13}$ is selected from

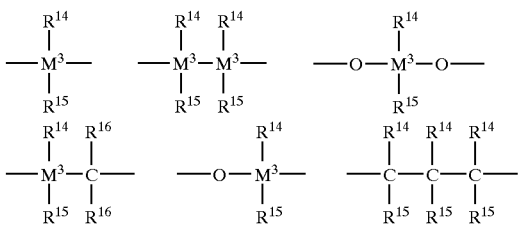

—$B(R^{14})$—, —$Al(R^{14})$—, —Ge—, —Sn—, —O—, —S—, —SO—, —$SO_2$—, —$N(R^{14})$—, —CO—, —$P(R)^{14}$— —$P(O)(R^{14})$—, —$B(NR^{14}R^{15})$— and —B[N$(SiR^{14}R^{15}R^{16})_2$]—. $R^{14}$, $R^{15}$ and $R^{16}$ are each independently selected from hydrogen, halogen, $C_1$–$C_{20}$ alkyl groups, $C_6$–$C_{30}$ aryl groups, $C_1$–$C_{20}$ alkoxy groups, $C_2$–$C_{20}$ alkenyl groups, $C_7$–$C_{40}$ arylalkyl groups, $C_8$–$C_{40}$ arylalkenyl groups and $C_7$–$C_{40}$ alkylaryl groups, or $R^{14}$ and $R^{15}$, together with the atom(s) connecting them, form a ring; and $M^3$ is selected from carbon, silicon, germanium and tin. Alternatively, $R^{13}$ is represented by the formula:

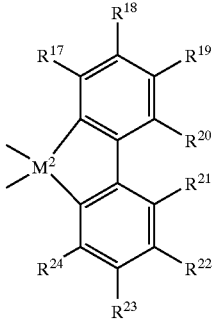

wherein $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings; $M^2$ is carbon, silicon, germanium, or tin. $R^8$, $R^9$, $R^{10}$ $R^{11}$ and $R^{12}$ are identical or different and have the meanings stated for $R^4$ to $R^7$.

Additional compounds suitable as olefin polymerization catalysts useful in the mixed-catalyst embodiments of the current invention will be any of those Group-3 to -10 compounds that can be converted by ligand abstraction or bond scission into a cationic catalyst and stabilized in that state by a noncoordinating or weakly coordinating anion sufficiently labile to be displaced by an olefinically unsaturated molecules such as ethylene.

Exemplary compounds include those described in the patent literature. International patent publications WO 96/23010, WO 97/48735 and Gibson, et al., *Chem. Comm.*, pp. 849–850 (1998), which disclose diimine-based ligands for Group-8 to -10 compounds that undergo ionic activation and polymerize olefins. Polymerization catalyst systems from Group-5–10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5–10, organometallic catalysts of copending U.S. application Ser. No. 09/302,243, filed 29 Apr. 1999, and its equivalent PCT/US99/09306. Group-11 catalyst precursor compounds, activable with ionizing cocatalysts, useful for olefin and vinylic polar molecules are described and exemplified in WO 99/30822 and its priority documents, including U.S. patent application Ser. No. 08/991,160, filed Dec. 16, 1997.

U.S. Pat. No. 5,318,935 describes bridged and unbridged, bisamido catalyst compounds of Group-4 metals capable of α-olefins polymerization. Bridged bis(arylamido) Group-4 compounds for olefin polymerization are described by D. H. McConville, et al., in *Organometallics* 1995, 14, 5478–5480. Synthetic methods and compound characterization are presented. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition metal compounds include those described in WO 96/40805. Cationic Group-3- or Lanthanide-metal olefin polymerization complexes are disclosed in copending U.S. application Ser. No. 09/408,050, filed Sep. 29, 1999, and its equivalent PCT/US99/22690. A monoanionic bidentate ligand and two monoanionic ligands stabilize those catalyst precursors, which can be activated with this invention's ionic cocatalysts.

The literature contains many additional descriptions of suitable catalyst-precursor compounds. Compounds that contain abstractable ligands or that can be alkylated to contain abstractable ligands are suitable for the practice of this invention. See, for instance, V. C. Gibson, et al; "The Search for New-Generation Olefin Polymerization Catalysts: Life Beyond Metallocenes", *Angew. Chem. Int. Ed.*, 38, 428–447 (1999).

Exemplary catalyst precursors useful in this invention include the following.

{[N-(2-phenyl-6-propyl-phenyl)-C-(butyl)-N-(2-phenyl-6-propyl-phenyl)]amidinato}di-{butyl}yttrium; {[N-(2-propyl-6-pentyl-phenyl)-C-(octyl)-N-(2-propyl-6-pentyl-phenyl)]amidinato}di-{methylethylamino}praseodymium; {[N-(2-pentyl-6-butylamino-phenyl)-C-(ethyl)-N-(2-pentyl-6-butylamino-phenyl)]amidinato}di-{tridecyl}yttrium; {[N-(2-butylamino-6-decyl-4-ethyl-phenyl)-C-(iodo)-N-(2-butylamino-6-decyl-4-ethyl-phenyl]amidinato}di-{ethyl}yttrium; {[N-(2-decyl-6-nonadecyl-phenyl)-C-(4-methylphenoxy)-N-(2-decyl-6-nonadecyl-phenyl)]amidinato}di-{dibutylamino}cerium; {[N-(2-nonadecyl-6-decyl-phenyl)-C-(methyl)-N-(2-nonadecyl-6-decyl-phenyl)]amidinato}di-{octadecyl}gadolinium; {[N-(2-decyl-6-benzyl-phenyl)-C-(methyl)-N-(2-decyl-6-benzyl-phenyl)]amidinato}di-{butyl}neodymium; {[N-(2-benzyl-6-butylamino-phenyl)-C-(butyl)-N-(2-benzyl-6-butylamino-phenyl)]amidinato}di-{tridecyl}praseodymium; {[N-(2-butylamino-6-dodecyl-phenyl)-C-(tetradecyl)-N-(2-butylamino-6-dodecyl-phenyl)]amidinato}di-{ethyl}yttrium; {[N-(2-dodecyl-6-heptadecyl-4-propyl-phenyl)-C-(propyl)-N-(2-dodecyl-6-heptadecyl-4-propyl-phenyl]amidinato}di-{ethyl}yttrium; {[N-(2-heptadecyl-6-hexadecyl-phenyl)-C-(butyl)-N-(2-heptadecyl-6-hexadecyl-phenyl)]amidinato}di-{propyl}neodymium; {[N-(2-hexadecyl-6-octadecyl-phenyl)-C-(propyl)-N-(2-hexadecyl-6-octadecyl-phenyl)]amidinato}di-{methyl}neodymium; {[N-(2-octadecyl-6-dodecyl-4-undecyl-phenyl)-C-(methyl)-N-(2-octadecyl-6-dodecyl-4-undecyl-phenyl]amidinato}di-{propyl}neodymium; {[P-(2-dodecyl-6-octyl-phenyl)-C-(methyl)-P-(2-dodecyl-6-octyl-phenyl)]phosphoamidinato}di-{hydrido}cerium; {[N-(2-octyl-6-pentadecyl-phenyl)-C-(triethylsilylmethyl)-P-(2-octyl-6-pentadecyl-phenyl)]phosphoamidinato}di-{propyl}samarium; {[N-(2-pentadecyl-6-diethylamino-phenyl)-C-(dibutylamino)-N-(2-pentadecyl-6-diethylamino-phenyl)]amidinato}di-{butyl}yttrium; {[N-(2-diethylamino-6-methylethylamino-phenyl)-C-(propyl)-N-(2-diethylamino-6-methylethylamino-phenyl)]amidinato}di-{hexyl}europium; {[N-(2-methylethylamino-6-heptadecyl-phenyl)-C-(methyl)-N-(2-methylethylamino-6-heptadecyl-phenyl)]amidinato}di-{ethyl}samarium; {[N-(2-heptadecyl-6-octadecyl-phenyl)-C-(bromo)-N-(2-heptadecyl-6-octadecyl-phenyl)]amidinato}di-{hydrido}samarium; {[N-(2-octadecyl-6-pentyl-phenyl)-C-(ethyl)-N-(2-octadecyl-6-pentyl-phenyl)]amidinato}di-{ethyl}cerium; {[N-(2-pentyl-6-heptadecyl-4-propyl-phenyl)-C-(chloro)-N-(2-pentyl-6-heptadecyl-4-propyl-phenyl]amidinato}di-{ethyl}neodymium; {[N-(2-heptadecyl-6-dimethylamino-phenyl)-C-(diethylphosphino)-N-(2-heptadecyl-6-dimethylamino-phenyl)]amidinato}di-{ethyl}samarium; {[N-(2-dimethylamino-6-pentyl-phenyl)-C-(propyl)-N-(2-dimethylamino-6-pentyl-phenyl)]amidinato}di-{ethyl}neodymium; {[N-(2-pentyl-6-phenyl-phenyl)-C-(ethyl)-P-(2-pentyl-6-phenyl-phenyl)]phosphoamidinato}di-{diphenylphosphino}yttrium; {[N-(2-phenyl-6-tridecyl-4-dodecyl-phenyl)-C-(butyl)-N-(2-phenyl-6-tridecyl-4-dodecyl-phenyl]amidinato}di-{propyl}yttrium; {[N-(2-tridecyl-6-diethylamino-phenyl)-C-(propyl)-N-(2-tridecyl-6-diethylamino-phenyl)]amidinato}di-{ethyl}neodymium; {[N-(2-diethylamino-6-undecyl-4-decyl-phenyl)-C-(butyl)-N-(2-diethylamino-6-undecyl-4-decyl-phenyl]amidinato}di-{propyl}neodymium; {[N-(2-undecyl-6-nonadecyl-phenyl)-C-(propyl)-N-(2-undecyl-6-nonadecyl-phenyl)]amidinato}di-{methyl}neodymium; {[N-(2-nonadecyl-6-heptadecyl-phenyl)-C-(methyl)-P-(2-nonadecyl-6-heptadecyl-phenyl)]phosphoamidinato}di-{propyl}yttrium; {[N-(2-heptadecyl-6-decyl-phenyl)-C-(propyl)-N-(2-heptadecyl-6-decyl-phenyl)]amidinato}di-{ethyl}neodymium; {[N-(2-decyl-6-benzyl-phenyl)-C-(chloro)-N-(2-decyl-6-benzyl-phenyl)]amidinato}di-{phenyl}praseodymium; {[N-(2-benzyl-6-iodo-phenyl)-C-(ethyl)-N-(2-benzyl-6-iodo-phenyl)]amidinato}di-{undecyl}samarium; {[N-(2-iodo-6-triethylsilylmethyl-phenyl)-C-(propyl)-N-(2-iodo-6-triethylsilylmethyl-phenyl]amidinato}di-{4-methylphenoxy}yttrium; {[N-(2-triethylsilylmethyl-6-phenyl-phenyl)-C-(4-methylphenoxy)-N-(2-triethylsilylmethyl-6-phenyl-phenyl)]amidinato}di-{ethyl}europium; {[P-(2-phenyl-6-heptadecyl-4-butyl-phenyl)-C-(butyl)-P-(2-phenyl-6-heptadecyl-4-butyl-phenyl]phosphoamidinato}di-{diphenylphosphino}neodymium; {[N-(2-heptadecyl-6-diethylamino-3-methyl-phenyl)-C-(tetradecyl)-P-(2-heptadecyl-6-diethylamino-3-methyl-phenyl]phosphoamidinato}di-{methyl}yttrium; {[N-(2-diethylamino-6-heptyl-phenyl)-C-(methyl)-N-(2-diethylamino-6-heptyl-phenyl)]amidinato}di-{ethyl}neodymium; {[N-(2-heptyl-6-octadecyl-phenyl)-C-(propyl)-N-(2-heptyl-6-octadecyl-phenyl)]amidinato}di-{hexyl}yttrium; {[N-(2-octadecyl-6-chloro-phenyl)-C-(ethyl)-P-(2-octadecyl-6-chloro-phenyl)]phosphoamidinato}di-{butyl}neodymium; {[N-(2-chloro-6- octyl-phenyl)-C-(methyl)-N-(2-chloro-6-octyl-phenyl)]amidinato}di-{chloro}yttrium; {[N-(2-octyl-6-hexyl-4-phenyl-phenyl)-C-(propyl)-P-(2-octyl-6-hexyl-4-phenyl-phenyl]phosphoamidinato}di-{methyl}yttrium; {[N-(2-hexyl-6-heptadecyl-phenyl)-C-(hexadecyl)-N-(2-hexyl-6-heptadecyl-phenyl)]amidinato}di-{butyl}cerium; {[N-(2-heptadecyl-6-butylamino-phenyl)-C-(chloro)-N-(2-heptadecyl-6-butylamino-phenyl)]amidinato}di-{butyl}neodymium; {[N-(2-butylamino-6-benzyl-phenyl)-C-(methyl)-N-(2-butylamino-6-benzyl-phenyl]amidinato}di-{propyl}neodymium; {[N-(2-benzyl-6-butylamino-3-diphenylphosphino-phenyl)-C-(propyl)-N-(2-benzyl-6-butylamino-3-diphenylphosphino-phenyl]amidinato}di-{tetradecyl}neodymium; {[N-(2-butylamino-6-tridecyl-phenyl)-C-(propyl)-N-(2-butylamino-6-tridecyl-phenyl)]amidinato}di-{diethylphosphino}cerium; {[N-(2-tridecyl-6-tetradecyl-phenyl)-C-(benzyl)-N-(2-tridecyl-6-tetradecyl-phenyl)]amidinato}di-{butyl}samarium; {[N-(2-tetradecyl-6-butylamino-phenyl)-C-(ethyl)-N-(2-tetradecyl-6-butylamino-phenyl)]amidinato}di-{propyl}yttrium; {[N-(2-butylamino-6-methylethylamino-phenyl)-C-(methyl)-N-(2-butylamino-6-methylethylamino-phenyl)]amidinato}di-{propyl}neodymium; {[N-(2-methylethylamino-6-benzyl-phenyl)-C-(hydrido)-N-(2-methylethylamino-6-benzyl-phenyl)]amidinato}di-{methylethylamino}yttrium; {[N-(2-benzyl-6-decyl-phenyl)-C-(ethyl)-N-(2-benzyl-6-decyl-phenyl)]amidinato}di-{propyl}neodymium; {[N-(2-decyl-6-butylamino-phenyl)-C-(ethyl)-N-(2-decyl-6-butylamino-phenyl)]amidinato}di-{butyl}europium; {[N-(2-butylamino-6-iodo-phenyl)-C-(butyl)-N-(2-butylamino-6-iodo-phenyl)]amidinato}di-{propyl}yttrium; {[N-(2-iodo-6-hexyl-phenyl)-C-(hydrido)-N-(2-iodo-6-hexyl-phenyl)]amidinato}di-{hexadecyl}samarium; {[N-(2-hexyl-6-dibutylamino-phenyl)-C-(ethyl)-N-(2-hexyl-6-dibutylamino-phenyl)]amidinato}di-{propyl}yttrium; {[N-(2-dibutylamino-6-hexadecyl-3-butyl-phenyl)-C-(methyl)-N-(2-dibutylamino-6-hexadecyl-3-butyl-phenyl]amidinato}di-{ethyl}cerium; {[N-(2-hexadecyl-6-methylethylamino-phenyl)-C-(dimethylamino)-N-(2-hexadecyl-6-methylethylamino-phenyl)]amidinato}di-{propyl}yttrium; {[N-(2-methylethylamino-6-propyl-phenyl)-C-(chloro)-N-(2-methylethylamino-6-propyl-phenyl)]amidinato}di-{butyl}yttrium; {[N-(2-propyl-6-nonadecyl-phenyl)-C-(butyl)-P-(2-propyl-6-nonadecyl-phenyl)]phosphoamidinato}di-{propyl}samarium; {[N-(2-nonadecyl-6-methylethylamino-phenyl)-C-(hydrido)-N-(2-nonadecyl-6-methylethylamino-6-methylethylamino-phenyl)]amidinato}di-{iodo}neodymium; {[N-(2-methylethylamino-6-nonyl-phenyl)-C-(heptyl)-N-(2-methylethylamino-6-nonyl-phenyl)]amidinato}di-{ethyl}europium; {[N-(2-nonyl-6-heptyl-phenyl)-C-(propyl)-P-(2-nonyl-6-heptyl-phenyl)]phosphoamidinato}di-{butyl}samarium; {[N-(2-heptyl-6-nonadecyl-phenyl)-C-(butyl)-P-(2-heptyl-6-nonadecyl-phenyl)]phosphoamidinato}di-{hydrido}yttrium; {[N-(2-nonadecyl-6-nonyl-phenyl)-C-(methyl)-P-(2-nonadecyl-6-nonyl-phenyl)]phosphoamidinato}di-{ethyl}neodymium; {[N-(2-nonyl-6-triethylsilylmethyl-phenyl)-C-(pentadecyl)-N-(2-nonyl-6-triethylsilylmethyl-phenyl)]amidinato}di-{ethyl}gadolinium; {[N-(2-triethylsilylmethyl-6-pentadecyl-phenyl)-C-(propyl)-N-(2-triethylsilylmethyl-6-pentadecyl-phenyl)]amidinato}di-{propyl}neodymium; {[N-(2-pentadecyl-6-heptyl-phenyl)-C-(hydrido)-P-(2-pentadecyl-6-heptyl-phenyl)]phosphoamidinato}di-{butyl}samarium; {[N-(2-heptyl-6-pentyl-phenyl)-C-(propyl)-N-(2-heptyl-6-pentyl-phenyl)]amidinato}di-{propyl}samarium; {[N-(2-pentyl-6-nonadecyl-phenyl)-C-(hydrido)-N-(2-pentyl-6-nonadecyl-phenyl)]amidinato}di-{hydrido}yttrium; {[N-(2-nonadecyl-6-trimethylsilylethyl-3-butyl-phenyl)-C-(ethyl)-N-(2-nonadecyl-6-trimethylsilylethyl-3-butyl-phenyl]amidinato}di-{methyl}neodymium; {[N-(2-trimethylsilylethyl-6-heptyl-phenyl)-C-(methyl)-P-(2-trimethylsilylethyl-6-heptyl-phenyl)]phosphoamidinato}di-{undecyl}neodymium; {[P-(2-heptyl-6-butyl-4-ethyl-phenyl)-C-(diphenylphosphino)-P-(2-heptyl-6-butyl-4-ethyl-phenyl]phosphoamidinato}di-{propyl}samarium; {[N-(2-butyl-6-heptadecyl-phenyl)-C-(4-methylphenoxy)-N-(2-butyl-6-heptadecyl-phenyl)]amidinato}di-{propyl}yttrium; {[N-(2-heptadecyl-6-decyl-phenyl)-C-(butylamino)-N-(2-heptadecyl-6-decyl-phenyl)]amidinato}di-{hydrido}yttrium; {[P-(2-decyl-6-dibutylamino-phenyl)-C-(diphenylphosphino)-P-(2-decyl-6-dibutylamino-phenyl)]phosphoamidinato}di-{propyl}neodymium; {[N-(2-dibutylamino-6-octadecyl-phenyl)-C-(tetradecyl)-N-(2-dibutylamino-6-octadecyl-phenyl)]amidinato}di-{butyl}neodymium; {[N-(2-octadecyl-6-phenyl-phenyl)-C-(hexyl)-N-(2-octadecyl-6-phenyl-phenyl)]amidinato}di-{chloro}yttrium; {[N-(2-phenyl-6-dibutylamino-4-methyl-phenyl)-C-(butyl)-N-(2-phenyl-6-dibutylamino-4-methyl-phenyl]amidinato}di-{methylethylamino}europium; {[N-(2-dibutylamino-6-tridecyl-4-butyl-phenyl)-C-(propyl)-N-(2-dibutylamino-6-tridecyl-4-butyl-phenyl]amidinato}di-{propyl}neodymium; {[N-(2-tridecyl-6-dibutylamino-phenyl)-C-(ethyl)-N-(2-tridecyl-6-dibutylamino-phenyl)]amidinato}di-{hydrido}neodymium; {[N-(2-dibutylamino-6-heptyl-phenyl)-C-(methyl)-N-(2-dibutylamino-6-heptyl-phenyl)]amidinato}di-{hydrido}neodymium; {[N-(2-heptyl-6-octyl-4-propyl-phenyl)-C-(hydrido)-N-(2-heptyl-6-octyl-4-propyl-phenyl]amidinato}di-{diethylamino}yttrium; {[N-(2-octyl-6-dimethylamino-phenyl)-C-(butyl)-N-(2-octyl-6-dimethylamino-phenyl)]amidinato}di-{propyl}neodymium; {[N-(2-dimethylamino-6-triethylsilylmethyl-phenyl)-C-(methyl)-N-(2-dimethylamino-6-triethylsilylmethyl-phenyl)]amidinato}di-{propyl}cerium; {[N-(2-triethylsilylmethyl-6-octyl-4-propyl-phenyl)-C-(methyl)-N-(2-triethylsilylmethyl-6-octyl-4-propyl-phenyl]amidinato}di-{methyl}yttrium; {[N-(2-octyl-6-nonadecyl-phenyl)-C-(propyl)-N-(2-octyl-6-nonadecyl-phenyl)]amidinato}di-{methylethylamino}praseodymium; {[N-(2-nonadecyl-6-pentadecyl-phenyl)-C-(methyl)-N-(2-nonadecyl-6-pentadecyl-phenyl)]amidinato}di-{nonyl}neodymium; {[N-(2-pentadecyl-6-tridecyl-phenyl)-C-(propyl)-N-(2-pentadecyl-6-tridecyl-phenyl)]amidinato}di-{butyl}yttrium; {[N-(2-tridecyl-6-propyl-phenyl)-C-(butyl)-N-(2-tridecyl-6-propyl-phenyl)]amidinato}di-{ethyl}cerium; {[N-(2-propyl-6-heptyl-phenyl)-C-(hydrido)-N-(2-propyl-6-heptyl-phenyl)]amidinato}di-{ethyl}yttrium; {[N-(2-heptyl-6-hexadecyl-3-butyl-phenyl)-C-(pentadecyl)-N-(2-heptyl-6-hexadecyl-3-butyl-phenyl]amidinato}di-{butyl}yttrium; {[N-(2-hexadecyl-6-pentyl-phenyl)-C-(butyl)-N-(2-hexadecyl-6-pentyl-phenyl)]amidinato}di-{nonyl}cerium; {[N-(2-pentyl-6-dimethylamino-4-propyl-phenyl)-C-(methyl)-N-(2-pentyl-6-dimethylamino-4-propyl-phenyl]amidinato}di-{decyl}praseodymium; {[N-(2-dimethylamino-6-phenyl-phenyl)-C-(propyl)-P-(2-dimethylamino-6-phenyl-phenyl)]phosphoamidinato}di-{hexadecyl}neodymium; {[N-(2-phenyl-6-iodo-phenyl)-C-(propyl)-N-(2-phenyl-6-iodo-phenyl)]amidinato}di-{tridecyl}samarium; {[N-(2-iodo-6-heptyl-phenyl)-C-(methyl)-N-(2-iodo-6-heptyl-phenyl)]amidinato}di-{ethyl}neodymium; {[P-(2-heptyl-6-butylamino-phenyl)-C-(butyl)-P-(2-heptyl-6-butylamino-phenyl)]phosphoamidinato}di-{methyl}neodymium; {[N-

(2-butylamino-6-diphenylphosphino-phenyl)-C-(hydrido)-N-(2-butylamino-6-diphenylphosphino-phenyl)]amidinato}di-{ethyl}yttrium; {[N-(2-diphenylphosphino-6-butylamino-phenyl)-C-(propyl)-N-(2-diphenylphosphino-6butylamino-phenyl)]amidinato}di-{iodo}neodymium; {[N-(2-butylamino-6-trimethylsilylethyl-phenyl)-C-(ethyl)-N-(2-butylamino-6-trimethylsilylethyl-phenyl)]amidinato}di-{propyl}yttrium; {[N-(2-trimethylsilylethyl-6-heptadecyl-phenyl)-C-(propyl)-N-(2-trimethylsilylethyl-6-heptadecyl-phenyl)]amidinato}di-{diethylphosphino}yttrium; {[N-(2-methylethylamino-6-decyl-phenyl)-C-(methyl)-N-(2-methylethylamino-6-decyl-phenyl)]amidinato}{octadecyl}{diethylamino}yttrium; {[N-(2-decyl-6-tetradecyl-phenyl)-C-(ethyl)-P-(2-decyl-6-tetradecyl-phenyl)]phosphoamidinato}{ethyl}{methyl}neodymium; {[N-(2-tetradecyl-6-nonadecyl-phenyl)-C-(ethyl)-N-(2-tetradecyl-6-nonadecyl-phenyl)]amidinato}di-{butyl}neodymium; {[P-(2-nonadecyl-6-pentadecyl-phenyl)-C-(propyl)-P-(2-nonadecyl-6-pentadecyl-phenyl)]phosphoamidinato}{hydrido}{butyl}europium; {[N-(2-pentadecyl-6-heptadecyl-phenyl)-C-(hydrido)-P-(2-pentadecyl-6-heptadecyl-phenyl)]phosphoamidinato}{ethyl}{butyl}samarium; {[N-(2-heptadecyl-6-nonadecyl-phenyl)-C-(methyl)-N-(2-heptadecyl-6-nonadecyl-phenyl)]amidinato}{methyl}{propyl}praseodymium; {[P-(2-nonadecyl-6-propyl-phenyl)-C-(ethyl)-P-(2-nonadecyl-6-propyl-phenyl)]phosphoamidinato}{diphenylphosphino}{ethyl}yttrium; {[N-(2-propyl-6-hexyl-phenyl)-C-(diethylphosphino)-N-(2-propyl-6-hexyl-phenyl)]amidinato}{bromo}{butyl}praseodymium; {[N-(2-hexyl-6-nonadecyl-phenyl)-C-(decyl)-N-(2-hexyl-6-nonadecyl-phenyl)]amidinato}{methyl}{hydrido}yttrium; {[N-(2-nonadecyl-6-bromo-phenyl)-C-(propyl)-N-(2nonadecyl-6-bromo-phenyl)]amidinato}{octadecyl}{butyl}neodymium; {[N-(2-bromo-6-undecyl-phenyl)-C-(butyl)-N-(2-bromo-6-undecyl-phenyl)]amidinato}{hexadecyl}{propyl}neodymium; {[N-(2-undecyl-6-hexadecyl-phenyl)-C-(benzyl)-N-(2-undecyl-6-hexadecyl-phenyl)]amidinato}{ethyl}{hydrido}yttrium; {[N-(2-hexadecyl-6-dodecyl-phenyl)-C-(butyl)-N-(2-hexadecyl-6-dodecyl-phenyl)]amidinato}{methyl}{propyl}yttrium; {[N-(2-dodecyl-6-octadecyl-phenyl)-C-(ethyl)-N-(2-dodecyl-6-octadecyl-phenyl)]amidinato}{diphenylphosphino}{propyl}neodymium; {[N-(2-octadecyl-6-dimethylamino-phenyl)-C-(propyl)-N-(2-octadecyl-6-dimethylamino-phenyl)]amidinato}{propyl}{hexyl}europium; {[N-(2-dimethylamino-6-heptyl-phenyl)-C-(butyl)-N-(2-dimethylamino-6-heptyl-phenyl)]amidinato}{butyl}{propyl}yttrium; {[N-(2-heptyl-6-dimethylamino-phenyl)-C-(ethyl)-N-(2-heptyl-6-dimethylamino-phenyl)]amidinato}{4-methylphenoxy}{iodo}europium; {[P-(2-dimethylamino-6-nonadecyl-phenyl)-C-(ethyl)-P-(2-dimethylamino-6-nonadecyl-phenyl)]phosphoamidinato}di-{methyl}cerium; {[N-(2-nonadecyl-6-methylethylamino-3-chloro-phenyl)-C-(ethyl)-N-(2-nonadecyl-6-methylethylamino-3-chloro-phenyl]amidinato}{ethyl}{hydrido}cerium; {[N-(2-methylethylamino-6-iodo-phenyl)-C-(hydrido)-N-(2-methylethylamino-6-iodo-phenyl)]amidinato}{tridecyl}{methyl}neodymium; {[N-(2-iodo-6-undecyl-4-hydrido-phenyl)-C-(propyl)-P-(2-iodo-6-undecyl-4-hydrido-phenyl]phosphoamidinato}{propyl}{hydrido}europium; {[N-(2-undecyl-6-tetradecyl-phenyl)-C-(butyl)-N-(2-undecyl-6-tetradecyl-phenyl)]amidinato}{butyl}{methyl}yttrium; {[N-(2-tetradecyl-6-hexadecyl-phenyl)-C-(hydrido)-N-(2-tetradecyl-6-hexadecyl-phenyl)]amidinato}{hexyl}{propyl}samarium; {[N-(2-hexadecyl-6-pentadecyl-phenyl)-C-(butyl)-N-(2-hexadecyl-6-pentadecyl-phenyl)]amidinato}{tridecyl}{butyl}cerium; {[N-(2-pentadecyl-6-heptadecyl-phenyl)-C-(methyl)-N-(2-pentadecyl-6-heptadecyl-phenyl)]amidinato}{propyl}{4-methylphenoxy}samarium; {[N-(2-heptadecyl-6-iodo-phenyl)-C-(dimethylamino)-N-(2-heptadecyl-6-iodo-phenyl)]amidinato}{propyl}{butyl}cerium; {[N-(2-iodo-6-methylethylamino-phenyl)-C-(butyl)-N-(2-iodo-6-methylethylamino-phenyl)]amidinato}di-{butyl}neodymium; {[N-(2-methylethylamino-6-phenyl-phenyl)-C-(butyl)-P-(2-methylethylamino-6-phenyl-phenyl)]phosphoamidinato}{propyl}{hydrido}cerium; {[N-(2-phenyl-6-nonadecyl-phenyl)-C-(ethyl)-N-(2-phenyl-6-nonadecyl-phenyl)]amidinato}{tetradecyl}{chloro}cerium; {[N-(2-nonadecyl-6-pentyl-phenyl)-C-(heptadecyl)-N-(2-nonadecyl-6-pentyl-phenyl)]amidinato}{methyl}{bromo}yttrium; {[N-(2-pentyl-6-undecyl-phenyl)-C-(propyl)-N-(2-pentyl-6-undecyl-phenyl)]amidinato}{propyl}{butyl}cerium; {[N-(2-undecyl-6-pentyl-phenyl)-C-(hydrido)-N-(2-undecyl-6-pentyl-phenyl)]amidinato}{hydrido}{butyl}gadolinium; {[N-(2-pentyl-6-benzyl-phenyl)-C-(butyl)-N-(2-pentyl-6-benzyl-phenyl)]amidinato}{methyl}{diphenylphosphino}yttrium; {[N-(2-benzyl-6-hexadecyl-phenyl)-C-(butyl)-N-(2-benzyl-6-hexadecyl-phenyl)]amidinato}{methyl}{propyl}samarium; {[P-(2-hexadecyl-6-bromo-phenyl)-C-(ethyl)-P-(2-hexadecyl-6-bromo-phenyl)]phosphoamidinato}{heptadecyl}{ethyl}neodymium; {[N-(2-bromo-nonyl-phenyl)-C-(propyl)-N-(2-bromo-6-nonyl-phenyl)]amidinato}di-{ethyl}yttrium; {[N-(2-nonyl-6-pentyl-phenyl)-C-(ethyl)-N-(2-nonyl-6-pentyl-phenyl)]amidinato}{iodo}{diethylphosphino}samarium; {[N-(2-pentyl-6-bromo-4-propyl-phenyl)-C-(butyl)-N-(2-pentyl-6-bromo-4-propyl-phenyl]amidinato}{propyl}{methyl}yttrium; {[N-(2-bromo-6-iodo-phenyl)-C-(bromo)-P-(2-bromo-6-iodo-phenyl)]phosphoamidinato}{phenyl}{butyl}samarium; {[N-(2-iodo-6-hexadecyl-phenyl)-C-(methyl)-N-(2-iodo-6-hexadecyl-phenyl)]amidinato}{butyl}{tridecyl}samarium; {[N-(2-hexadecyl-6-heptyl-4-phenyl-phenyl)-C-(pentyl)-N-(2-hexadecyl-6-heptyl-4-phenyl-phenyl]amidinato}di-{ethyl}neodymium; {[N-(2-heptyl-6-butyl-phenyl)-C-(butyl)-N-(2-heptyl-6-butyl-phenyl)]amidinato}{ethyl}{butyl}cerium; {[N-(2-butyl-6-undecyl-4-butyl-phenyl)-C-(tridecyl)-N-(2-butyl-6-undecyl-4-butyl-phenyl]amidinato}{propyl}{ethyl}samarium; {[N-(2-undecyl-6-octyl-phenyl)-C-(propyl)-N-(2-undecyl-6-octyl-phenyl)]amidinato}{methyl}{propyl}yttrium; {[N-(2-octyl-6-octadecyl-phenyl)-C-(methyl)-N-(2-octyl-6-octadecyl-phenyl)]amidinato}{butyl}{heptadecyl}neodymium; {[N-(2-octadecyl-6-trimethylsilylethyl-phenyl)-C-(hydrido)-N-(2-octadecyl-6-trimethylsilylethyl-phenyl)]amidinato}{methyl}{bromo}yttrium; {[N-(2-trimethylsilylethyl-6-octadecyl-phenyl)-C-(butyl)-N-(2-trimethylsilylethyl-6-octadecyl-phenyl)]amidinato}di-{butyl}cerium; {[N-(2-octadecyl-6-pentadecyl-phenyl)-C-(ethyl)-N-(2-octadecyl-6-pentadecyl-phenyl)]amidinato}{hydrido}{pentyl}yttrium; {[N-(2-pentadecyl-6-tridecyl-phenyl)-C-(hydrido)-N-(2-pentadecyl-6-tridecyl-phenyl)]amidinato}{methyl}{heptyl}gadolinium; {[N-(2- tridecyl-6-butylamino-4-hexadecyl-phenyl)-C-(bromo)-N-(2-tridecyl-6-butylamino-4-hexadecyl-phenyl]amidinato}{ethyl}{dimethylamino}yttrium; {[P-(2-butylamino-6-trimethylsilylethyl-phenyl)-C-(methyl)-P-(2-butylamino-6-trimethylsilylethyl-phenyl)]phosphoamidinato}{ethyl}{iodo}cerium; {[N-(2-trimethylsilylethyl-6-octyl-phenyl)-C-(ethyl)-N-(2-trimethylsilylethyl-6-octyl-phenyl)]amidinato}{ethyl}{methyl}praseodymium; {[N-(2-octyl-6-4-methylphenoxy-phenyl)-C-(propyl)-N-(2-octyl-6-4-methylphenoxy-phenyl)]amidinato}{propyl}{hydrido}neodymium; {[N-(2-4-methylphenoxy-6-diethylamino-4-ethyl-phenyl)-C-(propyl)-N-(2-4-methylphenoxy-6-diethylamino-4-ethyl-phenyl]amidinato}di-{butyl}cerium; {[N-(2-diethylamino-6-dimethylamino-phenyl)-C-(butyl)-N-(2-diethylamino-6-dimethylamino-phenyl)]amidinato}{propyl}{ethyl}europium; {[N-(2-dimethylamino-6-tetradecyl-phenyl)-C-(propyl)-N-(2-dimethylamino-6-tetradecyl-phenyl)]amidinato}{heptadecyl}{butyl}samarium; {[N-(2-tetradecyl-6-dimethylamino-phenyl)-C-(propyl)-N-(2-tetradecyl-6-dimethylamino-phenyl)]amidinato}{propyl}{ethyl}neodymium; {[N-(2-dimethylamino-6-nonyl-4-diethylphosphino-phenyl)-C-(hydrido)-N-(2-dimethylamino-6-nonyl-4-diethylphosphino-phenyl]amidinato}{ethyl}{benzyl}yttrium; {[N-(2-nonyl-6-butylamino-phenyl)-C-(perfluorophenyl)-N-(2-nonyl-6-butylamino-phenyl)]amidinato}{methyl}{phenyl}neodymium; {[N-(2-butylamino-6-triethylsilylmethyl-phenyl)-C-(pentyl)-N-(2-butylamino-6-triethylsilylmethyl-phenyl)]amidinato}{methyl}{ethyl}samarium; {[N-(2-triethylsilylmethyl-6-heptadecyl-phenyl)-C-(butyl)-P-(2-triethylsilylmethyl-6-heptadecyl-phenyl)]phosphoamidinato}{ethyl}{hydrido}cerium; {[N-(2-heptadecyl-6-octadecyl-phenyl)-C-(dimethylamino)-N-(2-heptadecyl-6-octadecyl-phenyl)]amidinato}{butyl}{hydrido}yttrium; {[N-(2-octadecyl-6-octyl-4-butyl-phenyl)-C-(heptadecyl)-N-(2-octadecyl-6-octyl-4-butyl-phenyl]amidinato}{ethyl}{chloro}cerium; {[N-(2-octyl-6-pentadecyl-phenyl)-C-(undecyl)-N-(2-octyl-6-pentadecyl-phenyl)]amidinato}{propyl}{octyl}neodymium; {[N-(2-pentadecyl-6-undecyl-4-propyl-phenyl)-C-(methyl)-N-(2-pentadecyl-6-undecyl-4-propyl-phenyl]amidinato}{benzyl}{butyl}samarium; {[N-(2-undecyl-6-dimethylamino-4-butyl-phenyl)-C-(methyl)-N-(2-undecyl-6-dimethylamino-4-butyl-phenyl]amidinato}{undecyl}{propyl}cerium; {[N-(2-dimethylamino-6-bromo-3-perfluorophenyl-phenyl)-C-(methyl)-N-(2-dimethylamino-6-bromo-3-perfluorophenyl-phenyl]amidinato}{ethyl}{methyl}cerium; {[N-(2-bromo-6-pentyl-phenyl)-C-(ethyl)-N-(2-bromo-6-pentyl-phenyl)]amidinato}{propyl}{ethyl}gadolinium; {[N-(2-pentyl-6-octyl-phenyl)-C-(methyl)-N-(2-pentyl-6-octyl-phenyl)]amidinato}{ethyl}{methyl}praseodymium; {[P-(2-octyl-6-tetradecyl-phenyl)-C-(methyl)-P-(2-octyl-6-tetradecyl-phenyl)]phosphoamidinato}{propyl}{butyl}neodymium; {[N-(2-tetradecyl-6-hexadecyl-phenyl)-C-(propyl)-N-(2-tetradecyl-6-hexadecyl-phenyl)]amidinato}{methyl}{propyl}gadolinium; {[N-(2-hexadecyl-6-trimethylsilylethyl-phenyl)-C-(propyl)-N-(2-hexadecyl-6-trimethylsilylethyl-phenyl)]amidinato}{methyl}{ethyl}europium; {[N-(2-trimethylsilylethyl-6-tetradecyl-phenyl)-C-(dibutylamino)-N-(2-trimethylsilylethyl-6-tetradecyl-phenyl)]amidinato}{propyl}{dimethylamino}neodymium; {[N-(2-tetradecyl-6-nonyl-phenyl)-C-(propyl)-N-(2-tetradecyl-6-nonyl-phenyl)]amidinato}{hydrido}{hexyl}neodymium; {[N-(2-nonyl-6-nonadecyl-phenyl)-C-(butyl)-P-(2-nonyl-6-nonadecyl-phenyl)]phosphoamidinato}{ethyl}{pentadecyl}yttrium; {[P-(2-nonadecyl-6-pentyl-phenyl)-C-(propyl)-P-(2-nonadecyl-6-pentyl-phenyl)]phosphoamidinato}{diethylamino}{ethyl}neodymium; {[N-(2-pentyl-6-nonadecyl-phenyl)-C-(pentadecyl)-P-(2-pentyl-6-nonadecyl-phenyl)]phosphoamidinato}{propyl}{methyl}cerium; {[N-(2-nonadecyl-6-chloro-phenyl)-C-(butyl)-N-(2-nonadecyl-6-chloro-phenyl)]amidinato}{propyl}{methyl}yttrium; {[N-(2-chloro-6-4-methylphenoxy-phenyl)-C-(ethyl)-N-(2-chloro-6-4-methylphenoxy-phenyl)]amidinato}{butyl}{butylamino}gadolinium; {[P-(2-4-methylphenoxy-6-diphenylphosphino-phenyl)-C-(methyl)-P-(2-4-methylphenoxy-6-diphenylphosphino-phenyl)]phosphoamidinato}{ethyl}{methyl}neodymium; {[N-(2-diphenylphosphino-6-dimethylamino-phenyl)-C-(propyl)-N-(2-diphenylphosphino-6-dimethylamino-phenyl)]amidinato}di-{butyl}yttrium; {[N-(2-dimethylamino-6-iodo-phenyl)-C-(octadecyl)-N-(2-dimethylamino-6-iodo-phenyl)]amidinato}{propyl}{methyl}europium; {[N-(2-iodo-6-hexadecyl-phenyl)-C-(hexadecyl)-N-(2-iodo-6-hexadecyl-phenyl)]amidinato}{butyl}{methyl}yttrium; {[N-(2-hexadecyl-6-benzyl-phenyl)-C-(methyl)-N-(2-hexadecyl-6-benzyl-phenyl)]amidinato}{undecyl}{methyl}europium; {[N-(2-benzyl-6-nonadecyl-phenyl)-C-(tridecyl)-N-(2-benzyl-6-nonadecyl-phenyl)]amidinato}{propyl}{undecyl}neodymium; {[N-(2-nonadecyl-6-decyl-phenyl)-C-(propyl)-N-(2-nonadecyl-6-decyl-phenyl)]amidinato}{propyl}{butyl}praseodymium; {[N-(2-decyl-6-trimethylsilylethyl-phenyl)-C-(methyl)-N-(2-decyl-6-trimethylsilylethyl-phenyl)]amidinato}{perfluorophenyl}{phenyl}praseodymium; {[N-(2-trimethylsilylethyl-6-butyl-phenyl)-C-(butyl)-N-(2-trimethylsilylethyl-6-butyl-phenyl)]amidinato}{methyl}{hydrido}yttrium; {[N-(2-butyl-6-iodo-phenyl)-C-(dibutylamino)-N-(2-butyl-6-iodo-phenyl)]amidinato}{butyl}{ethyl}yttrium; {[N-(2-iodo-6-hexyl-phenyl)-C-(ethyl)-N-(2-iodo-6-hexyl-phenyl)]amidinato}{propyl}{methyl}neodymium; {[N-(2-hexyl-6-benzyl-phenyl)-C-(ethyl)-N-(2-hexyl-6-benzyl-phenyl)]amidinato}{diphenylphosphino}{ethyl}europium; {[N-(2-benzyl-6-pentyl-phenyl)-C-(ethyl)-N-(2-benzyl-6-pentyl-phenyl)]amidinato}{dimethylamino}{tridecyl}yttrium; {[N-(2-pentyl-6-octyl-phenyl)-C-(ethyl)-N-(2-pentyl-6-octyl-phenyl)]amidinato}{chloro}{methyl}neodymium; {[N-(2-octyl-6-triethylsilylmethyl-phenyl)-C-(methyl)-P-(2-octyl-6-triethylsilylmethyl-phenyl)]phosphoamidinato}{propyl}{diphenylphosphino}yttrium; {[N-(2-triethylsilylmethyl-6-tridecyl-phenyl)-C-(ethyl)-N-(2-triethylsilylmethyl-6-tridecyl-phenyl)]amidinato}{nonyl}{ethyl}yttrium; {[N-(2-tridecyl-6-heptyl-4-propyl-phenyl)-C-(ethyl)-N-(2-tridecyl-6-heptyl-4-propyl-phenyl]amidinato}{ethyl}{hydrido}neodymium; {[N-(2-heptyl-6-pentyl-phenyl)-C-(ethyl)-N-(2-heptyl-6-pentyl-phenyl)]amidinato}{ethyl}{butyl}neodymium; {[N-(2-pentyl-6-trimethylsilylethyl-phenyl)-C-(tetradecyl)-N-(2-pentyl-6-trimethylsilylethyl-phenyl)]amidinato}{ethyl}{propyl}cerium; {[N-(2-trimethylsilylethyl-6-iodo-phenyl)-C-(butyl)-N-(2-trimethylsilylethyl-6-iodo-phenyl)]amidinato}{butyl}{propyl}cerium; {[N-(2-iodo-6-4- methylphenoxy-4-butyl-phenyl)-C-(butyl)-P-(2-iodo-6-4-methylphenoxy-4-butyl-phenyl]phosphoamidinato}{butyl}{ethyl}yttrium; {[N-(2-4-methylphenoxy-6-dibutylamino-phenyl)-C-(propyl)-P-(2-4-methylphenoxy-6-dibutylamino-phenyl)]phosphoamidinato}{ethyl}{perfluorophenyl}samarium; {[N-(2,6-didodecyl-phenyl)-C-(hydrido)-N-(2,6-didodecyl-phenyl)]amidinato}{butyl}{propyl}samarium; {[N-(2,6-ditridecyl-phenyl)-C-(methyl)-N-(2,6-ditridecyl-phenyl)]amidinato}di-{chloro}yttrium; {[N-(2,6-diheptadecyl-phenyl)-C-(propyl)-N-(2,6-diheptadecyl-phenyl)]amidinato}di-{propyl}neodymium; {[N-(2,6-ditridecyl-phenyl)-C-(methyl)-N-(2,6-ditridecyl-phenyl)]amidinato}{butyl}{propyl}yttrium; {[N-(2,6-diphenyl-phenyl)-C-(hydrido)-N-(2,6-diphenyl-phenyl)]amidinato}{ethyl}{methyl}europium; {[N-(2,6-dibromo-phenyl)-C-(methyl)-N-(2,6-dibromo-phenyl)]amidinato}{ethyl}{methyl}neodymium; {[N-(2,6-dipentadecyl-phenyl)-C-(methyl)-P-(2,6-dipentadecyl-phenyl)]phosphoamidinato}{hydrido}{pentadecyl}yttrium; {[P-(2,6-di4-methylphenoxy-phenyl)-C-(octyl)-P-(2,6-di4-methylphenoxy-phenyl)]phosphoamidinato}{butyl}{propyl}yttrium; {[N-(2,6-diphenyl-phenyl)-C-(propyl)-N-(2,6-diphenyl-phenyl)]amidinato}{propyl}{ethyl}neodymium; {[N-(2,6-didodecyl-phenyl)-C-(butyl)-N-(2,6-didodecyl-phenyl)]amidinato}{butylamino}{octyl}neodymium; {[N-(2,6-dibromo-phenyl)-C-(nonyl)-N-(2,6-dibromo-phenyl)]amidinato}{butyl}{propyl}cerium; {[N-(2,6-dibromo-phenyl)-C-(diethylphosphino)-N-(2,6-dibromo-phenyl)]amidinato}{ethyl}{propyl}neodymium; {[N-(2,6-dimethylethylamino-phenyl)-C-(hexyl)-N-(2,6-dimethylethylamino-phenyl)]amidinato}{diphenylphosphino}{methyl}neodymium; {[N-(2,6-dipentadecyl-phenyl)-C-(iodo)-N-(2,6-dipentadecyl-phenyl)]amidinato}{methyl}{butyl}yttrium; {[N-(2,6-dipentyl-phenyl)-C-(propyl)-N-(2,6-dipentyl-phenyl)]amidinato}{methyl}{methylethylamino}samarium; {[N-(2,6-ditrimethylsilylethyl-phenyl)-C-(ethyl)-P-(2,6-ditrimethylsilylethyl-phenyl)]phosphoamidinato}{butyl}{hydrido}neodymium; {[N-(2,6-dihexadecyl-phenyl)-C-(methyl)-N-(2,6-dihexadecyl-phenyl)]amidinato}di-{propyl}neodymium; {[N-(2,6-dihexadecyl-3-butyl-phenyl)-C-(methyl)-N-(2,6-dihexadecyl-3-butyl-phenyl)]amidinato}{dimethylamino}{butyl}yttrium; {[N-(2,6-diheptyl-phenyl)-C-(propyl)-P-(2,6-diheptyl-phenyl)]phosphoamidinato}{butyl}{hydrido}europium; {[N-(2,6-diundecyl-phenyl)-C-(propyl)-N-(2,6-diundecyl-phenyl)]amidinato}{ethyl}{butyl}yttrium; {[N-(2,6-bis(dimethylamino)-phenyl)-C-(butylamino)-P-(2,6-bis(dimethylamino)-phenyl)]phosphoamidinato}di-{propyl}neodymium; {[N-(2,6-ditridecyl-phenyl)-C-(butyl)-N-(2,6-ditridecyl-phenyl)]amidinato}{ethyl}{butyl}neodymium; {[P-(2,6-dimethylethylamino-phenyl)-C-(propyl)-P-(2,6-dimethylethylamino-phenyl)]phosphoamidinato}{chloro}{butyl}gadolinium; {[N-(2,6-ditetradecyl-phenyl)-C-(propyl)-N-(2,6-ditetradecyl-phenyl)]amidinato}{methyl}{butyl}samarium; {[N-(2,6-ditetradecyl-phenyl)-C-(ethyl)-N-(2,6-ditetradecyl-phenyl)]amidinato}di-{propyl}yttrium; {[N-(2,6-ditridecyl-4-hydrido-phenyl)-C-(methyl)-N-(2,6-ditridecyl-4-hydrido-phenyl]amidinato}di-{ethyl}neodymium; {[N-(2,6-dibenzyl-phenyl)-C-(propyl)-N-(2,6-dibenzyl-phenyl)]amidinato}{iodo}{4-methylphenoxy}yttrium; {[N-(2,6-bis(dibutylamino)-phenyl)-C-(4-methylphenoxy)-N-(2,6-bis(dibutylamino)-phenyl)]amidinato}{hydrido}{butyl}gadolinium; {[N-(2,6-didodecyl-phenyl)-C-(diphenylphosphino)-N-(2,6-didodecyl-phenyl)]amidinato}{phenyl}{butyl}neodymium; {[N-(2,6-ditriethylsilylmethyl-phenyl)-C-(methyl)-N-(2,6-ditriethylsilylmethyl-phenyl)]amidinato}{propyl}{methyl}cerium; {[N-(2,6-didodecyl-phenyl)-C-(methyl)-N-(2,6-didodecyl-phenyl)]amidinato}{ethyl}{methyl}neodymium; {[N-(2,6-diundecyl-4-hydrido-phenyl)-C-(ethyl)-N-(2,6-diundecyl-4-hydrido-phenyl]amidinato}{heptyl}{ethyl}yttrium; {[N-(2,6-bis(diethylamino)-phenyl)-C-(ethyl)-P-(2,6-bis(diethylamino)-phenyl)]phosphoamidinato}{phenyl}{benzyl}yttrium; {[N-(2,6-dihexadecyl-phenyl)-C-(methyl)-N-(2,6-dihexadecyl-phenyl)]amidinato}{diethylamino}{propyl}cerium; {[P-(2,6-ditriethylsilylmethyl-phenyl)-C-(butyl)-P-(2,6-ditriethylsilylmethyl-phenyl)]phosphoamidinato}{methyl}{propyl}praseodymium; {[P-(2,6-bis(diphenylphosphino)-phenyl)-C-(methyl)-P-(2,6-bis(diphenylphosphino)-phenyl)]phosphoamidinato}{hydrido}{butyl}neodymium; {[N-(2,6-dibutyl-phenyl)-C-(ethyl)-N-(2,6-dibutyl-phenyl)]amidinato}{decyl}{propyl}yttrium; {[N-(2,6-dibutylamino-phenyl)-C-(propyl)-N-(2,6-dibutylamino-phenyl)]amidinato}{ethyl}{methyl}yttrium; {[N-(2,6-diphenyl-phenyl)-C-(propyl)-N-(2,6-diphenyl-phenyl)]amidinato}{phenyl}{methyl}samarium; {[N-(2,6-ditridecyl-phenyl)-C-(butyl)-N-(2,6-ditridecyl-phenyl)]amidinato}{dodecyl}{octyl}gadolinium; {[N-(2,6-dibromo-phenyl)-C-(butyl)-P-(2,6-dibromo-phenyl)]phosphoamidinato}{ethyl}{propyl}neodymium; {[N-(2,6-dibutylamino-phenyl)-C-(methyl)-N-(2,6-dibutylamino-phenyl)]amidinato}{4-methylphenoxy}{butylamino}neodymium; {[N-(2,6-ditrimethylsilylethyl-phenyl)-C-(methyl)-N-(2,6-ditrimethylsilylethyl-phenyl)]amidinato}{ethyl}{phenyl}samarium; {[N-(2,6-dihexadecyl-phenyl)-C-(diphenylphosphino)-N-(2,6-dihexadecyl-phenyl)]amidinato}{hydrido}{methyl}neodymium; {[N-(2,6-didecyl-phenyl)-C-(butyl)-N-(2,6-didecyl-phenyl)]amidinato}{methyl}{propyl}samarium; {[N-(2,6-dioctadecyl-phenyl)-C-(propyl)-N-(2,6-dioctadecyl-phenyl)]amidinato}{methyl}{propyl}samarium; {[N-(2,6-dipentyl-phenyl)-C-(ethyl)-N-(2,6-dipentyl-phenyl)]amidinato}{diethylphosphino}{propyl}europium; {[N-(2,6-ditetradecyl-4-methyl-phenyl)-C-(decyl)-N-(2,6-ditetradecyl-4-methyl-phenyl]amidinato}{propyl}{octadecyl}yttrium; {[N-(2,6-dipentadecyl-phenyl)-C-(butyl)-N-(2,6-dipentadecyl-phenyl)]amidinato}{methyl}{butyl}neodymium; {[N-(2,6-ditriethylsilylmethyl-phenyl)-C-(butyl)-N-(2,6-ditriethylsilylmethyl-phenyl)]amidinato}{bromo}{dimethylamino}neodymium; {[N-(2,6-diheptyl-4-methyl-phenyl)-C-(methyl)-N-(2,6-diheptyl-4-methyl-phenyl]amidinato}di-{ethyl}neodymium; {[N-(2,6-ditetradecyl-phenyl)-C-(undecyl)-N-(2,6-ditetradecyl-phenyl)]amidinato}{propyl}{hydrido}neodymium; {[P-(2,6-dinonyl-phenyl)-C-(methyl)-P-(2,6-dinonyl-phenyl)]phosphoamidinato}{butyl}{phenyl}yttrium; {[N-(2,6-bis(diethylamino)-phenyl)-C-(butyl)-N-(2,6-bis(diethylamino)-phenyl)]amidinato}{ethyl}{propyl}neodymium; {[N-(2,6-bis(diphenylphosphino)-phenyl)-C-(ethyl)-N-(2,6-bis(diphenylphosphino)-phenyl)]amidinato}{butyl}{methyl}neodymium; {[N-(2,6-dihexylphenyl)-C-(diethylamino)-N-(2,6-dihexyl-phenyl)]amidinato}{propyl}{ethyl}europium; {[N-(2,6-bis(diphenylphosphino)-phenyl)-C-(propyl)-N-(2,6-bis(diphenylphosphino)-phenyl)]amidinato}{ethyl}{methyl}yttrium; {[N-(2,6-dibromo-phenyl)-C-(butyl)-N-(2,6-dibromo-phenyl)]amidinato}{methyl}{heptadecyl}yttrium; {[N-(2,6-dibutyl-phenyl)-C-(propyl)-N-(2,6-dibutyl-phenyl)]amidinato}{bromo}{propyl}yttrium; {[N-(2,6-diundecyl-phenyl)-C-(butylamino)-N-(2,6-diundecyl-phenyl)]amidinato}{ethyl}{methyl}gadolinium; {[N-(2,6-bis(diethylamino)-phenyl)-C-(ethyl)-N-(2,6-bis(diethylamino)-phenyl)]amidinato}di-{propyl}yttrium; {[N-(2,6-ditrimethylsilylethyl-phenyl)-C-(butyl)-N-(2,6-ditrimethylsilylethyl-phenyl)]amidinato}di-{ethyl}cerium; {[N-(2,6-dipentadecyl-phenyl)-C-(butyl)-N-(2,6-dipentadecyl-phenyl)]amidinato}{butyl}{propyl}yttrium; {[N-(2,6-dihexadecyl-phenyl)-C-(butyl)-N-(2,6-dihexadecyl-phenyl)]amidinato}di-{propyl}cerium; {[N-(2,6-dioctyl-phenyl)-C-(ethyl)-P-(2,6-dioctyl-phenyl)]phosphoamidinato}{bromo}{ethyl}yttrium; {[N-(2,6-bis(diethylamino)-phenyl)-C-(chloro)-N-(2,6-bis(diethylamino)-phenyl)]amidinato}{ethyl}{methyl}cerium; {[N-(2,6-dibenzyl-phenyl)-C-(methyl)-N-(2,6-dibenzyl-phenyl)]amidinato}{pentyl}{chloro}yttrium; {[N-(2,6-diheptadecyl-phenyl)-C-(butyl)-N-(2,6-diheptadecyl-phenyl)]amidinato}{pentyl}{butyl}neodymium; {[N-(2,6-dibromo-phenyl)-C-(methyl)-P-(2,6-dibromo-phenyl)]phosphoamidinato}di-{methyl}europium; {[N-(2,6-dipentadecyl-phenyl)-C-(propyl)-N-(2,6-dipentadecyl-phenyl)]amidinato}{propyl}{diethylphosphino}praseodymium; {[N-(2,6-dioctadecyl-phenyl)-C-(propyl)-N-(2,6-dioctadecyl-phenyl)]amidinato}{propyl}{triethylsilylmethyl}yttrium; {[N-(2,6-di4-methylphenoxy-3-ethyl-phenyl)-C-(methyl)-N-(2,6-di4-methylphenoxy-3-ethyl-phenyl]amidinato}{butyl}{propyl}neodymium; {[N-(2,6-dipropyl-phenyl)-C-(phenyl)-N-(2,6-dipropyl-phenyl)]amidinato}{tridecyl}{propyl}prascodymium; {[N-(2,6-dipentadecyl-phenyl)-C-(bromo)-P-(2,6-dipentadecyl-phenyl)]phosphoamidinato}{dibutylamino}{butyl}gadolinium; {[N-(2,6-diundecyl-4-butyl-phenyl)-C-(methyl)-N-(2,6-diundecyl-4-butyl-phenyl]amidinato}{methyl}{bromo}europium; {[N-(2,6-diheptadecyl-phenyl)-C-(hexyl)-N-(2,6-diheptadecyl-phenyl)]amidinato}{octadecyl}{diphenylphosphino}samarium; {[N-(2,6-bis(dimethylamino)-3-perfluorophenyl-phenyl)-C-(methyl)-N-(2,6-bis(dimethylamino)-3-perfluorophenyl-phenyl]amidinato}{hexyl}{iodo}cerium; {[N-(2,6-ditetradecyl-phenyl)-C-(butyl)-N-(2,6-ditetradecyl-phenyl)]amidinato}{butyl}{diethylamino}yttrium; {[N-(2,6-dibromo-phenyl)-C-(butyl)-N-(2,6-dibromo-phenyl)]amidinato}{phenyl}{methyl}yttrium; {[N-(2,6-dihexyl-phenyl)-C-(ethyl)-N-(2,6-dihexyl-phenyl)]amidinato}{propyl}{ethyl}yttrium; {[N-(2,6-bis(dibutylamino)-phenyl)-C-(propyl)-N-(2,6-bis(dibutylamino)-phenyl)]amidinato}{dibutylamino}{propyl}neodymium; {[N-(2,6-dinonadecyl-phenyl)-C-(methyl)-N-(2,6-dinonadecyl-phenyl)]amidinato}{triethylsilylmethyl}{propyl}cerium; {[N-(2,6-di4-methylphenoxy-phenyl)-C-(butyl)-P-(2,6-di4-methylphenoxy-phenyl)]phosphoamidinato}{methyl}{propyl}samarium; {[N-(2,6-dinonadecyl-4-benzyl-phenyl)-C-(butyl)-N-(2,6-dinonadecyl-4-benzyl-phenyl]amidinato}{butyl}{propyl}europium; {[N-(2,6-dibutyl-phenyl)-C-(heptadecyl)-N-(2,6-dibutyl-phenyl)]amidinato}{octadecyl}{heptadecyl}yttrium; {[N-(2,6-diheptadecyl-phenyl)-C-(chloro)-N-(2,6-diheptadecyl-phenyl)]amidinato}{ethyl}{hydrido}yttrium; {[N-(2,6-dibutyl-phenyl)-C-(ethyl)-P-(2,6-dibutyl-phenyl)]phosphoamidinato}{ethyl}{propyl}neodymium; {[N-(2,6-diundecyl-3-hexyl-phenyl)-C-(iodo)-N-(2,6-diundecyl-3-hexyl-phenyl]amidinato}{ethyl}{propyl}samarium; {[N-(2,6-dibromo-phenyl)-C-(heptyl)-P-(2,6-dibromo-phenyl)]phosphoamidinato}{diphenylphosphino}{phenyl}yttrium; {[N-(2,6-bis(diphenylphosphino)-phenyl)-C-(butyl)-N-(2,6-bis(diphenylphosphino)-phenyl)]amidinato}{ethyl}{pentyl}yttrium; {[N-(2,6-dimethylethylamino-phenyl)-C-(butyl)-N-(2,6-dimethylethylamino-phenyl)]amidinato}{ethyl}{butyl}cerium; {[N-(2,6-diheptadecyl-phenyl)-C-(hydrido)-N-(2,6-diheptadecyl-phenyl)]amidinato}{tetradecyl}{methyl}neodymium; {[N-(2,6-dibutylamino-phenyl)-C-(propyl)-N-(2,6-dibutylamino-phenyl)]amidinato}{propyl}{diethylphosphino}samarium; {[N-(2,6-diheptyl-3-ethyl-phenyl)-C-(ethyl)-P-(2,6-diheptyl-3-ethyl-phenyl]phosphoamidinato}{methyl}{hydrido}yttrium; {[N-(2,6-bis(diethylamino)-4-butyl-phenyl)-C-(propyl)-N-(2,6-bis(diethylamino)-4-butyl-phenyl]amidinato}{propyl}{ethyl}europium; {[N-(2,6-dihexadecyl-phenyl)-C-(hydrido)-N-(2,6-dihexadecyl-phenyl)]amidinato}{dibutylamino}{octyl}yttrium; {[N-(2,6-bis(diphenylphosphino)-phenyl)-C-(butyl)-P-(2,6-bis(diphenylphosphino)-phenyl)]phosphoamidinato}{ethyl}{butyl}neodymium; {[P-(2,6-bis(diethylamino)-phenyl)-C-(hydrido)-P-(2,6-bis(diethylamino)-phenyl)]phosphoamidinato}di-{propyl}yttrium; {[P-(2,6-dioctyl-phenyl)-C-(chloro)-P-(2,6-dioctyl-phenyl)]phosphoamidinato}{hexyl}{hexadecyl}yttrium; {[N-(2,6-dimethylethylamino-phenyl)-C-(butyl)-N-(2,6-dimethylethylamino-phenyl)]amidinato}{methyl}{decyl}samarium; {[N-(2,6-didecyl-phenyl)-C-(ethyl)-N-(2,6-didecyl-phenyl)]amidinato}{nonyl}{iodo}yttrium; {[N-(2,6-bis(dimethylamino)-phenyl)-C-(pentyl)-N-(2,6-bis(dimethylamino)-phenyl)]amidinato}di-{methyl}yttrium; {[N-(2,6-dioctadecyl-phenyl)-C-(hydrido)-N-(2,6-dioctadecyl-phenyl)]amidinato}{ethyl}{propyl}yttrium; {[N-(2,6-dibenzyl-4-hydrido-phenyl)-C-(butyl)-N-(2,6-dibenzyl-4-hydrido-phenyl]amidinato}{methyl}{propyl}cerium; {[N-(2,6-dioctadecyl-phenyl)-C-(methyl)-N-(2,6-dioctadecyl-phenyl)]amidinato}{methyl}{propyl}neodymium; {[P-(2,6-ditridecyl-phenyl)-C-(propyl)-P-(2,6-ditridecyl-phenyl)]phosphoamidinato}{propyl}{pentadecyl}cerium; {[N-(2,6-dinonadecyl-phenyl)-C-(hydrido)-N-(2,6-dinonadecyl-phenyl)]amidinato}{tetradecyl}{undecyl}neodymium; {[P-(2,6-dinonadecyl-phenyl)-C-(pentyl)-P-(2,6-dinonadecyl-phenyl)]phosphoamidinato}di-{methyl}yttrium; {[N-(2,6-diiodo-phenyl)-C-(hydrido)-N-(2,6-diiodo-phenyl)]amidinato}{propyl}{butyl}yttrium; {[N-(2,6-di4-methylphenoxy-4-butyl-phenyl)-C-(ethyl)-N-(2,6-di4-methylphenoxy-4-butyl-phenyl]amidinato}{heptyl}{ethyl}samarium; {[N-(2,6-ditridecyl-phenyl)-C-(butyl)-N-(2,6-ditridecyl-phenyl)]amidinato}{ethyl}{butyl}samarium; {[N-(2,6-bis(diethylamino)-phenyl)-C-(methyl)-N-(2,6-bis(diethylamino)-phenyl)]

amidinato}{benzyl}{undecyl}gadolinium; {[N-(2,6-di4-methylphenoxy-phenyl)-C-(hydrido)-N-(2,6-di4-methylphenoxy-phenyl)]amidinato}{dimethylamino}{ethyl}yttrium; {[N-(2,6-dipentadecyl-phenyl)-C-(diethylamino)-N-(2,6-dipentadecyl-phenyl)]amidinato}{nonyl}{propyl}yttrium; {[N-(2,6-diiodo-phenyl)-C-(butyl)-N-(2,6-diiodo-phenyl)]amidinato}{propyl}{ethyl}yttrium; {[N-(2,6-dibutylamino-phenyl)-C-(methylethylamino)-N-(2,6-dibutylamino-phenyl)]amidinato}di-{ethyl}neodymium; {[N-(2,6-bis(diphenylphosphino)-phenyl)-C-(butyl)-N-(2,6-bis(diphenylphosphino)-phenyl)]amidinato}{butyl}{hydrido}neodymium; {[N-(2,6-ditridecyl-phenyl)-C-(methyl)-N-(2,6-ditridecyl-phenyl)]amidinato}{butyl}{propyl}yttrium; {[N-(2,6-diphenyl-phenyl)-C-(tetradecyl)-N-(2,6-diphenyl-phenyl)]amidinato}{methyl}{ethyl}samarium; {[N-(2,6-dinonyl-4-propyl-phenyl)-C-(propyl)-N-(2,6-dinonyl-4-propyl-phenyl]amidinato}{butyl}{propyl}samarium; {[N-(2,6-dihexadecyl-phenyl)-C-(butyl)-N-(2,6-dihexadecyl-phenyl)]amidinato}{propyl}{ethyl}neodymium; {[N-(2,6-ditriethylsilylmethyl-4-ethyl-phenyl)-C-(butyl)-N-(2,6-ditriethylsilylmethyl-4-ethyl-phenyl]amidinato}{4-methylphenoxy}{methyl}europium; {[N-(2,6-dinonyl-phenyl)-C-(ethyl)-N-(2,6-dinonyl-phenyl)]amidinato}{ethyl}{propyl}neodymium; {[N-(2,6-bis(dimethylamino)-4-diethylphosphino-phenyl)-C-(ethyl)-N-(2,6-bis(dimethylamino)-4-diethylphosphino-phenyl]amidinato}{propyl}{ethyl}cerium; {[P-(2,6-dipentyl-phenyl)-C-(chloro)-P-(2,6-dipentyl-phenyl)]phosphoamidinato}{heptadecyl}{butyl}neodymium; {[N-(2,6-diiodo-phenyl)-C-(methyl)-N-(2,6-diiodo-phenyl)]amidinato}{butyl}{octadecyl}yttrium; {[N-(2,6-bis(diethylamino)-phenyl)-C-(ethyl)-N-(2,6-bis(diethylamino)-phenyl]amidinato}di-{butyl}yttrium; {[P-(2,6-dipentyl-phenyl)-C-(butyl)-P-(2,6-dipentyl-phenyl)]phosphoamidinato}di-{propyl}praseodymium; {[P-(2,6-diphenyl-phenyl)-C-(methyl)-P-(2,6-diphenyl-phenyl)]phosphoamidinato}{propyl}{butyl}neodymium; {[N-(2,6-ditetradecyl-phenyl)-C-(dodecyl)-N-(2,6-ditetradecyl-phenyl)]amidinato}{butyl}{dimethylamino}yttrium; {[N-(2,6-didodecyl-phenyl)-C-(ethyl)-N-(2,6-didodecyl-phenyl)]amidinato}{butyl}{benzyl}cerium; {[N-(2,6-dibenzyl-phenyl)-C-(butyl)-P-(2,6-dibenzyl-phenyl)]phosphoamidinato}{propyl}{dibutylamino}europium; {[N-(2,6-bis(dibutylamino)-4-propyl-phenyl)-C -(methyl)-N-(2,6-bis(dibutylamino)-4-propyl-phenyl]amidinato}{propyl}{dimethylamino}yttrium; {[N-(2,6-didodecyl-phenyl)-C-(methyl)-N-(2,6-didodecyl-phenyl)]amidinato}{iodo}{perfluorophenyl}yttrium; {[N-(2,6-di4-methylphenoxy-phenyl)-C-(dodecyl)-P-(2,6-di4-methylphenoxy-phenyl)]phosphoamidinato}{hexyl}{diethylamino}neodymium; {[N-(2,6-dinonyl-phenyl)-C-(butyl)-N-(2,6-dinonyl-phenyl)]amidinato}di-{ethyl}neodymium; {[N-(2,6-dihexadecyl-phenyl)-C-(4-methylphenoxy)-N-(2,6-dihexadecyl-phenyl]amidinato}di-{butyl}yttrium; {[N-(2,6-dimethylethylamino-phenyl)-C-(dimethylamino)-N-(2,6-dimethylethylamino-phenyl)]amidinato}{butyl}{dibutylamino}yttrium; {[N-(2,6-diundecyl-phenyl)-C-(propyl)-N-(2,6-diundecyl-phenyl)]amidinato}{4-methylphenoxy}{undecyl}europium; {[N-(2,6-ditridecyl-phenyl)-C-(propyl)-N-(2,6-ditridecyl-phenyl)]amidinato}{butyl}{methyl}neodymium; {[N-(2,6-dimethylethylamino-phenyl)-C-(methyl)-N-(2,6-dimethylethylamino-phenyl)]amidinato}{propyl}{ethyl}yttrium; {[P-(2,6-diheptyl-phenyl)-C-(butyl)-P-(2,6-diheptyl-phenyl)]phosphoamidinato}{ethyl}{butyl}samarium; {[P-(2,6-didecyl-phenyl)-C-(propyl)-P-(2,6-didecyl-phenyl)]phosphoamidinato}{ethyl}{butyl}neodymium; {[N-(2,6-diiodo-phenyl)-C-(bromo)-N-(2,6-diiodo-phenyl)]amidinato}{butyl}{phenyl}neodymium; {[N-(2,6-dimethylethylamino-phenyl)-C-(chloro)-N-(2,6-dimethylethylamino-phenyl)]amidinato}di-{butyl}yttrium; {[N-(2,6-dibenzyl-phenyl)-C-(pentadecyl)-N-(2,6-dibenzyl-phenyl)]amidinato}di-{propyl}neodymium; {[N-(2,6-dihexyl-phenyl)-C-(ethyl)-N-(2,6-dihexyl-phenyl)]amidinato}{propyl}{ethyl}yttrium; {[N-(2,6-dibromo-4-hydrido-phenyl)-C-(propyl)-N-(2,6-dibromo-4-hydrido-phenyl]amidinato}{ethyl}{butyl}neodymium; {[N-(2,6-bis(diphenylphosphino)-phenyl)-C-(propyl)-N-(2,6-bis(diphenylphosphino)-phenyl)]amidinato}{ethyl}{methyl}yttrium; {[N-(2,6-dipentadecyl-phenyl)-C-(propyl)-P-(2,6-dipentadecyl-phenyl)]phosphoamidinato}{propyl}{hydrido}cerium; {[N-(2,6-dinonadecyl-phenyl)-C-(octadecyl)-N-(2,6-dinonadecyl-phenyl)]amidinato}{ethyl}{butyl}neodymium; {[N-(2,6-ditrimethylsilylethyl-phenyl)-C-(methyl)-N-(2,6-ditrimethylsilylethyl-phenyl)]amidinato}{propyl}{methyl}praseodymium; {[N-(2,6-dipentadecyl-phenyl)-C-(pentadecyl)-N-(2,6-dipentadecyl-phenyl)]amidinato}{triethylsilylmethyl}{methyl}samarium; {[N-(2,6-ditetradecyl-phenyl)-C-(methyl)-N-(2,6-ditetradecyl-phenyl)]amidinato}{butyl}{propyl}neodymium; {[N-(2,6-dipentyl-phenyl)-C-(butyl)-N-(2,6-dipentyl-phenyl)]amidinato}di-{propyl}yttrium; {[N-(2,6-dinonadecyl-phenyl)-C-(heptyl)-N-(2,6-dinonadecyl-phenyl)]amidinato}di-{methyl}yttrium; {[N-(2,6-dinonadecyl-phenyl)-C-(butyl)-N-(2,6-dinonadecyl-phenyl)]amidinato}{chloro}{diphenylphosphino}yttrium; {[N-(2,6-bis(diphenylphosphino)-phenyl)-C-(butyl)-N-(2,6-bis(diphenylphosphino)-phenyl)]amidinato}di-{propyl}neodymium; {[N-(2,6-dibromo-phenyl)-C-(diethylphosphino)-N-(2,6-dibromo-phenyl)]amidinato}{propyl}{methyl}yttrium; {[N-(2,6-dihexyl-phenyl)-C-(methyl)-N-(2,6-dihexyl-phenyl)]amidinato}{dodecyl}{propyl}yttrium; {[P-(2,6-dioctadecyl-4-phenyl-phenyl)-C-(ethyl)-P-(2,6-dioctadecyl-4-phenyl-phenyl]phosphoamidinato}{triethylsilylmethyl}{butyl}yttrium; {[N-(2,6-dinonadecyl-phenyl)-C-(propyl)-N-(2,6-dinonadecyl-phenyl)]amidinato}{methyl}{butylamino}samarium; {[N-(2,6-bis(dimethylamino)-3-ethyl-phenyl)-C-(propyl)-N-(2,6-bis(dimethylamino)-3-ethyl-phenyl]amidinato}{methyl}{propyl}yttrium; {[N-(2,6-dibutyl-phenyl)-C-(nonyl)-N-(2,6-dibutyl-phenyl)]amidinato}{ethyl}{propyl}yttrium; {[N-(2,6-dibutyl-phenyl)-C-(methyl)-N-(2,6-dibutyl-phenyl)]amidinato}{propyl}{4-methylphenoxy}yttrium; {[P-(2,6-dipentadecyl-4-propyl-phenyl)-C-(phenyl)-P-(2,6-dipentadecyl-4-propyl-phenyl]phosphoamidinato}{chloro}{propyl}yttrium; {[N-(2,6-bis(diethylamino)-phenyl)-C-(triethylsilylmethyl)-N-(2,6-bis(diethylamino)-phenyl)]amidinato}{methyl}{propyl}yttrium; {[P-(2,6-dihexadecyl-phenyl)-C-(methyl)-P-(2,6-dihexadecyl-phenyl)]phosphoamidinato}{ethyl}{nonyl}samarium; {[N-(2,6-di4-methylphenoxy-phenyl)-C-(propyl)-N-(2,6-di4-methylphenoxy-phenyl)]amidinato}di-{butyl}neodymium; {[N-(2,6-didodecyl-3-ethyl-phenyl)-C-(propyl)-P-(2,6-didodecyl-3-ethyl-phenyl]phosphoamidinato}di- {ethyl}neodymium; {[N-(2,6-bis(dibutylamino)-phenyl)-C-(dimethylamino)-P-(2,6-bis(dibutylamino)-phenyl)]phosphoamidinato}di-{methyl}neodymium; {[N-(2,6-bis(dibutylamino)-phenyl)-C-(hydrido)-N-(2,6-bis(dibutylamino)-phenyl)]amidinato}{hydrido}{ethyl}yttrium; {[N-(2,6-dioctadecyl-phenyl)-C-(pentyl)-P-(2,6-dioctadecyl-phenyl)]phosphoamidinato}{ethyl}{methyl}neodymium; {[N-(2,6-bis(diphenylphosphino)-phenyl)-C-(butyl)-N-(2,6-bis(diphenylphosphino)-phenyl)]amidinato}{diphenylphosphino}{hydrido}yttrium; {[N-(2,6-di4-methylphenoxy-phenyl)-C-(butyl)-N-(2,6-di4-methylphenoxy-phenyl)]amidinato}{ethyl}{butyl}neodymium; {[N-(2,6-bis(dimethylamino)-phenyl)-C-(propyl)-N-(2,6-bis(dimethylamino)-phenyl)]amidinato}{butyl}{methyl}gadolinium; {[N-(2,6-dipentadecyl-phenyl)-C-(propyl)-N-(2,6-dipentadecyl-phenyl)]amidinato}{methyl}{decyl}gadolinium; {[N-(2,6-ditetradecyl-phenyl)-C-(octadecyl)-N-(2,6-ditetradecyl-phenyl)]amidinato}{diphenylphosphino}{butyl}yttrium; {[N-(2,6-dibutylamino-phenyl)-C-(bromo)-N-(2,6-dibutylamino-phenyl)]amidinato}di-{ethyl}yttrium; {[N-(2,6-dibutyl-phenyl)-C-(phenyl)-N-(2,6-dibutyl-phenyl)]amidinato}{propyl}{hydrido}yttrium; {[N-(2,6-didodecyl-4-tridecyl-phenyl)-C-(hydrido)-N-(2,6-didodecyl-4-tridecyl-phenyl]amidinato}{propyl}{ethyl}neodymium; {[N-(2,6-dihexyl-phenyl)-C-(ethyl)-N-(2,6-dihexyl-phenyl)]amidinato}{propyl}{butyl}neodymium; {[N-(2,6-diiodo-phenyl)-C-(methyl)-N-(2,6-diiodo-phenyl)]amidinato}{phenyl}{methylethylamino}neodymium; {[N-(2,6-dihexadecyl-4-methyl-phenyl)-C-(tridecyl)-N-(2,6-dihexadecyl-4-methyl-phenyl]amidinato}{butyl}{ethyl}samarium; {[N-(2,6-bis(diphenylphosphino)-phenyl)-C-(methyl)-N-(2,6-bis(diphenylphosphino)-phenyl)]amidinato}{dibutylamino}{diethylamino}neodymium; {[N-(2,6-diheptadecyl-phenyl)-C-(methyl)-N-(2,6-diheptadecyl-phenyl)]amidinato}{propyl}{tridecyl}cerium; {[N-(2,6-dipentyl-4-tetradecyl-phenyl)-C-(ethyl)-N-(2,6-dipentyl-4-tetradecyl-phenyl]amidinato}{nonyl}{methyl}praseodymium; {[N-(2,6-ditridecyl-phenyl)-C-(methyl)-N-(2,6-ditridecyl-phenyl)]amidinato}{nonyl}{phenyl}samarium; {[N-(2,6-ditriethylsilylmethyl-phenyl)-C-(butyl)-N-(2,6-ditriethylsilylmethyl-phenyl)]amidinato}{propyl}{butyl}yttrium; {[N-(2,6-dipentyl-phenyl)-C-(propyl)-P-(2,6-dipentyl-phenyl)]phosphoamidinato}{ethyl}{methyl}yttrium; {[N-(2,6-diheptadecyl-4-hydrido-phenyl)-C-(butyl)-N-(2,6-diheptadecyl-4-hydrido-phenyl]amidinato}{butyl}{ethyl}yttrium; {[N-(2,6-dibutylamino-4-propyl-phenyl)-C-(propyl)-N-(2,6-dibutylamino-4-propyl-phenyl]amidinato}di-{propyl}yttrium; {[N-(2,6-dichloro-phenyl)-C-(nonyl)-N-(2,6-dichloro-phenyl)]amidinato}{dimethylamino}{butyl}neodymium; {[N-(2,6-di4-methylphenoxy-phenyl)-C-(butyl)-N-(2,6-di4-methylphenoxy-phenyl)]amidinato}{benzyl}{methyl}neodymium; {[P-(2,6-dihexadecyl-phenyl)-C-(ethyl)-P-(2,6-dihexadecyl-phenyl)]phosphoamidinato}{methyl}{triethylsilylmethyl}yttrium; {[N-(2,6-dichloro-phenyl)-C-(butyl)-N-(2,6-dichloro-phenyl)]amidinato}{propyl}{ethyl}yttrium; {[N-(2,6-diheptadecyl-phenyl)-C-(propyl)-N-(2,6-diheptadecyl-phenyl)]amidinato}{methyl}{butyl}praseodymium; {[N-(2,6-dipropyl-4-ethyl-phenyl)-C-(ethyl)-N-(2,6-dipropyl-4-ethyl-phenyl]amidinato}{diphenylphosphino}{ethyl}neodymium; {[N-(2,6-dipentadecyl-4-hydrido-phenyl)-C-(diethylphosphino)-N-(2,6-dipentadecyl-4-hydrido-phenyl]amidinato}{butyl}{ethyl}cerium; {[N-(2,6-ditrimethylsilylethyl-phenyl)-C-(propyl)-N-(2,6-ditrimethylsilylethyl-phenyl)]amidinato}{diphenylphosphino}{propyl}yttrium; {[N-(2,6-diundecyl-4-iodo-phenyl)-C-(methylethylamino)-N-(2,6-diundecyl-4-iodo-phenyl]amidinato}{hydrido}{ethyl}yttrium; {[N-(2,6-dibromo-phenyl)-C-(butyl)-N-(2,6-dibromo-phenyl)]amidinato}{propyl}{methyl}yttrium; {[N-(2,6-bis(dimethylamino)-phenyl)-C-(methyl)-N-(2,6-bis(dimethylamino)-phenyl)]amidinato}{diethylamino}{butyl}cerium; {[N-(2,6-diiodo-4-propyl-phenyl)-C-(propyl)-N-(2,6-diiodo-4-propyl-phenyl]amidinato}{decyl}{butyl}praseodymium; {[N-(2,6-di4-methylphenoxy-4-ethyl-phenyl)-C-(butyl)-N-(2,6-di4-methylphenoxy-4-ethyl-phenyl]amidinato}{propyl}{methyl}neodymium; {[N-(2,6-bis(dimethylamino)-phenyl)-C-(iodo)-N-(2,6-bis(dimethylamino)-phenyl)]amidinato}{methyl}{butyl}europium; {[N-(2,6-dibenzyl-phenyl)-C-(perfluorophenyl)-N-(2,6-dibenzyl-phenyl)]amidinato}{ethyl}{hydrido}neodymium; {[N-(2,6-bis(dibutylamino)-phenyl)-C-(pentyl)-N-(2,6-bis(dibutylamino)-phenyl)]amidinato}{methyl}{,propyl}cerium; {[N-(2,6-bis(diphenylphosphino)-phenyl)-C-(diethylphosphino)-N-(2,6-bis(diphenylphosphino)-phenyl)]amidinato}{methyl}{undecyl}cerium; {[N-(2,6-diheptyl-phenyl)-C-(butyl)-N-(2,6-diheptyl-phenyl)]amidinato}{methyl}{butyl}neodymium; {[N-(2,6-diphenyl-phenyl)-C-(butyl)-N-(2,6-diphenyl-phenyl)]amidinato}{phenyl}{iodo}yttrium; {[N-(2,6-dioctyl-3-diphenylphosphino-phenyl)-C-(hydrido)-N-(2,6-dioctyl-3-diphenylphosphino-phenyl]amidinato}{methyl}{butyl}neodymium; {[N-(2,6-dibutyl-phenyl)-C-(benzyl)-N-(2,6-dibutyl-phenyl)]amidinato}{methylethylamino}{phenyl}samarium; {[N-(2,6-dioctadecyl-phenyl)-C-(methyl)-N-(2,6-dioctadecyl-phenyl)]amidinato}{propyl}{ehtyl}praseodymium; {[N-(2,6-diiodo-3-butyl-phenyl)-C-(butylamino)-N-(2,6-diiodo-3-butyl-phenyl]amidinato}{triethylsilylmethyl}{butyl}yttrium; {[N-(2,6-dioctadecyl-phenyl)-C-(propyl)-N-(2,6-dioctadecyl-phenyl)]amidinato}{ethyl}{butyl}neodymium; {[N-(2,6-didodecyl-4-propyl-phenyl)-C-(diethylphosphino)-N-(2,6-didodecyl-4-propyl-phenyl]amidinato}{methyl}{dibutylamino}cerium; {[N-(2,6-dipentadecyl-phenyl)-C-(dodecyl)-N-(2,6-dipentadecyl-phenyl)]amidinato}{ethyl}{methyl}yttrium; {[N-(2,6-bis(dimethylamino)-phenyl)-C-(hydrido)-N-(2,6-bis(dimethylamino)-phenyl)]amidinato}{propyl}{iodo}yttrium; {[N-(2,6-dioctadecyl-phenyl)-C-(ethyl)-P-(2,6-dioctadecyl-phenyl)]phosphoamidinato}{pentyl}{ethyl}cerium; {[N-(2,6-diundecyl-phenyl)-C-(ethyl)-N-(2,6-diundecyl-phenyl)]amidinato}{hydrido}{propyl}gadolinium; {[N-(2,6-didodecyl-phenyl)-C-(butyl)-N-(2,6-didodecyl-phenyl)]amidinato}di-{dimethylamino}neodymium; {[P-(2,6-dibutylamino-phenyl)-C-(butyl)-P-(2,6-dibutylamino-phenyl)]phosphoamidinato}{propyl}{methyl}neodymium; {[N-(2,6-didecyl-4-propyl-phenyl)-C-(chloro)-N-(2,6-didecyl-4-propyl-phenyl]amidinato}{propyl}{benzyl}neodymium; {[N-(2,6-bis(dimethylamino)-phenyl)-C-(hydrido)-N-(2,6-bis(dimethylamino)-phenyl)]

amidinato}{ethyl}{butyl}yttrium; {[N-(2,6-dibutyl-3-butyl-phenyl)-C-(propyl)-N-(2,6-dibutyl-3-butyl-phenyl] amidinato}{heptadecyl}{butyl}yttrium; {[N-(2,6-ditetradecyl-4-methyl-phenyl)-C-(ethyl)-N-(2,6-ditetradecyl-4-methyl-phenyl] amidinato}{butyl}{methyl}neodymium; {[N-(2,6-dimethylethylamino-phenyl)-C-(ethyl)-N-(2,6-dimethylethylamino-phenyl)] amidinato}{propyl}{undecyl}yttrium; {[N-(2,6-bis(dibutylamino)-phenyl)-C-(methyl)-N-(2,6-bis(dibutylamino)-phenyl)]amidinato}{butyl}{propyl}cerium; {[N-(2,6-bis(dibutylamino)-phenyl)-C-(phenyl)-N-(2,6-bis(dibutylamino)-phenyl)] amidinato}{hydrido}{propyl}neodymium; {[N-(2,6-dipropyl-phenyl)-C-(propyl)-N-(2,6-dipropyl-phenyl)] amidinato}di-{butyl}praseodymium; {[N-(2,6-dichloro-phenyl)-C-(methyl)-N-(2,6-dichloro-phenyl)] amidinato}{butyl}{phenyl}yttrium; {[N-(2,6-dihexadecyl-phenyl)-C-(ethyl)-P-(2,6-dihexadecyl-phenyl)] phosphoamidinato}{heptadecyl}{butyl}cerium; {[N-(2,6-didodecyl-phenyl)-C-(butylamino)-P-(2,6-didodecyl-phenyl)]phosphoamidinato}{propyl}{methyl}neodymium; {[N-(2,6-bis(diphenylphosphino)-phenyl)-C-(ethyl)-N-(2,6-bis(diphenylphosphino)-phenyl)] amidinato}{butylamino}{methyl}neodymium; {[N-(2,6-ditridecyl-phenyl)-C-(pentyl)-N-(2,6-ditridecyl-phenyl)] amidinato}{methyl}{propyl}yttrium; {[N-(2,6-ditetradecyl-phenyl)-C-(methyl)-N-(2,6-ditetradecyl-phenyl)]amidinato}{methyl}{propyl}neodymium; {[N-(2,6-diheptyl-phenyl)-C-(ethyl)-N-(2,6-diheptyl-phenyl)] amidinato}{ethyl}{butyl}samarium; {[N-(2,6-ditrimethylsilylethyl-phenyl)-C-(propyl)-N-(2,6-ditrimethylsilylethyl-phenyl)] amidinato}{propyl}{ethyl}samarium; {[N-(2,6-bis(diethylamino)-phenyl)-C-(phenyl)-N-(2,6-bis(diethylamino)-phenyl)] amidinato}{octadecyl}{butylamino}gadolinium; {[N-(2,6-di4-methylphenoxyphenyl)-C-(ethyl)-N-(2,6-di4-methylphenoxy-phenyl)]amidinato}{butyl}{4-methylphenoxy}praseodymium; {[N-(2,6-bis(dibutylamino)-phenyl)-C-(butyl)-N-(2,6-bis(dibutylamino)-phenyl)] amidinato}{propyl}{methyl}yttrium; {[N-(2,6-dibenzyl-phenyl)-C-(ethyl)-N-(2,6-dibenzyl-phenyl)] amidinato}{iodo}{ethyl}yttrium; {[N-(2,6-bis(dibutylamino)-phenyl)-C-(propyl)-N-(2,6-bis(dibutylamino)-phenyl)] amidinato}{ethyl}{butyl}neodymium; {[N-(2,6-dipentyl-phenyl)-C-(diphenylphosphino)-N-(2,6-dipentyl-phenyl)] amidinato}{propyl}{ethyl}yttrium; {[P-(2,6-dioctyl-phenyl)-C-(butyl)-P-(2,6-dioctyl-phenyl)] phosphoamidinato}{butyl}{ethyl}samarium; {[N-(2,6-bis(dibutylamino)-phenyl)-C-(4-methylphenoxy)-N-(2,6-bis(dibutylamino)-phenyl)] amidinato}{dodecyl}{ethyl}yttrium; {[N-(2,6-di4-methylphenoxy-phenyl)-C-(ethyl)-N-(2,6-di4-methylphenoxy-phenyl)] amidinato}{methyl}{dibutylamino}neodymium; {[N-(2,6-dibutyl-phenyl)-C-(methyl)-N-(2,6-dibutyl-phenyl)] amidinato}{butyl}{methyl}yttrium; {[P-(2,6-dibutylamino-phenyl)-C-(ethyl)-P-(2,6-dibutylamino-phenyl)] phosphoamidinato}{ethyl}{heptyl}cerium; {[N-(2,6-dichloro-phenyl)-C-(propyl)-N-(2,6-dichloro-phenyl)] amidinato}{methyl}{butyl}neodymium; {[N-(2,6-dimethylethylamino-phenyl)-C-(dodecyl)-N-(2,6-dimethylethylamino-phenyl)] amidinato}{butyl}{ethyl}cerium; {[N-(2,6-bis(diethylamino)-phenyl)-C-(methyl)-N-(2,6-bis(diethylamino)-phenyl)]amidinato}di-{propyl}gadolinium; {[N-(2,6-dibenzyl-phenyl)-C-(methyl)-N-(2,6-dibenzyl-phenyl)]amidinato}{hydrido}{phenyl}cerium; {[N-(2,6-diheptadecyl-4-propyl-phenyl)-C-(propyl)-N-(2,6-diheptadecyl-4-propyl-phenyl] amidinato}{methyl}{propyl}yttrium; {[N-(2,6-ditridecyl-phenyl)-C-(hexadecyl)-N-(2,6-ditridecyl-phenyl)] amidinato}di-{methyl}yttrium; {[N-(2,6-dipentadecyl-phenyl)-C-(methyl)-N-(2,6-dipentadecyl-phenyl)] amidinato}{iodo}{ethyl}neodymium; {[N-(2,6-diphenyl-phenyl)-C-(propyl)-N-(2,6-diphenyl-phenyl)] amidinato}{iodo}{propyl}neodymium; {[N-(2,6-ditriethylsilylmethyl-phenyl)-C-(propyl)-N-(2,6-ditriethylsilylmethyl-phenyl)] amidinato}{butyl}{triethylsilylmethyl}cerium; {[N-(2,6-dinonyl-phenyl)-C-(methyl)-N-(2,6-dinonyl-phenyl)] amidinato}{methyl}{diethylphosphino}neodymium; {[N-(2,6-dihexadecyl-phenyl)-C-(propyl)-N-(2,6-dihexadecyl-phenyl)]amidinato}{propyl}{butyl}neodymium; {[N-(2,6-dichloro-phenyl)-C-(butyl)-N-(2,6-dichloro-phenyl)] amidinato}{hydrido}{methyl}europium; {[N-(2,6-ditetradecyl-phenyl)-C-(butyl)-N-(2,6-ditetradecyl-phenyl)] amidinato}{dimethylamino}{butyl}gadolinium; {[N-(2,6-ditrimethylsilylethyl-phenyl)-C-(methyl)-N-(2,6-ditrimethylsilylethyl-phenyl)]amidinato}di-{ethyl}yttrium; {[N-(2,6-dinonyl-phenyl)-C-(propyl)-N-(2,6-dinonyl-phenyl)]amidinato}{butyl}{propyl}yttrium; {[N-(2,6-dimethylethylamino-phenyl)-C-(propyl)-N-(2,6-dimethylethylamino-phenyl)] amidinato}{methyl}{hydrido}yttrium; {[N-(2,6-diheptyl-phenyl)-C-(propyl)-P-(2,6-diheptyl-phenyl)] phosphoamidinato}{methyl}{hydrido}neodymium; {[N-(2,6-bis(diethylamino)-phenyl)-C-(methyl)-N-(2,6-bis(diethylamino)-phenyl)]amidinato}{ethyl}{methyl}cerium; {[N-(2,6-diiodo-phenyl)-C-(butyl)-P-(2,6-diiodo-phenyl)] phosphoamidinato}{ethyl}{methyl}samarium; {[N-(2,6-ditridecyl-4-propyl-phenyl)-C-(ethyl)-N-(2,6-ditridecyl-4-propyl-phenyl]amidinato}{propyl}{ethyl}yttrium; {[N-(2,6-dipropyl-4-propyl-phenyl)-C-(diethylphosphino)-N-(2,6-dipropyl-4-propyl-phenyl] amidinato}{phenyl}{diethylamino}yttrium; {[N-(2,6-dibromo-phenyl)-C-(ethyl)-N-(2,6-dibromo-phenyl)] amidinato}{methyl}{dodecyl}neodymium; {[N-(2,6-diiodo-phenyl)-C-(heptadecyl)-N-(2,6-diiodo-phenyl)] amidinato}{butyl}{ethyl}europium; {[P-(2,6-dibromo-3-methyl-phenyl)-C-(propyl)-P-(2,6-dibromo-3-methyl-phenyl]phosphoamidinato}{propyl}{ethyl}neodymium; {[N-(2,6-dipentyl-phenyl)-C-(undecyl)-N-(2,6-dipentyl-phenyl)]amidinato}{methyl}{ethyl}neodymium; {[N-(2,6-bis(diphenylphosphino)-phenyl)-C-(ethyl)-N-(2,6-bis(diphenylphosphino)-phenyl)] amidinato}{propyl}{methyl}neodymium; {[N-(2,6-bis(dimethylamino)-phenyl)-C-(decyl)-N-(2,6-bis(dimethylamino)-phenyl)] amidinato}{propyl}{ethyl}samarium; {[N-(2,6-diheptyl-phenyl)-C-(propyl)-N-(2,6-diheptyl-phenyl)] amidinato}{methyl}{propyl}yttrium; {[N-(2,6-dihexyl-phenyl)-C-(iodo)-N-(2,6-dihexyl-phenyl)] amidinato}{phenyl}{methyl}gadolinium; {[N-(2,6-ditrimethylsilylethyl-phenyl)-C-(propyl)-P-(2,6-ditrimethylsilylethyl-phenyl)] phosphoamidinato}{butyl}{methyl}neodymium; {[N-(2,6-dinonyl-4-dodecyl-phenyl)-C-(ethyl)-N-(2,6-dinonyl-4-dodecyl-phenyl]amidinato}{octyl}{butyl}yttrium; {[N-(2,6-dioctyl-3-hydrido-phenyl)-C-(ethyl)-N-(2,6-dioctyl-3-hydrido-phenyl]amidinato}{heptyl}{butyl}yttrium; {[N-(2, 6-dioctyl-phenyl)-C-(butyl)-N-(2,6-dioctyl-phenyl)]amidinato}{ethyl}{methyl}praseodymium; {[N-(2,6-dinonyl-phenyl)-C-(hydrido)-N-(2,6-dinonyl-phenyl)]amidinato}{propyl}{methyl}neodymium; {[N-(2,6-dinonadecyl-phenyl)-C-(ethyl)-N-(2,6-dinonadecyl-phenyl)]amidinato}{hydrido}{butyl}neodymium; {[N-(2,6-diundecyl-4-butyl-phenyl)-C-(triethylsilylmethyl)-N-(2,6-diundecyl-4-butyl-phenyl]amidinato}{dodecyl}{methyl}neodymium; {[N-(2,6-dibutylamino-phenyl)-C-(propyl)-N-(2,6-dibutylamino-phenyl)]amidinato}{ethyl}{butyl}neodymium; {[P-(2,6-diheptadecyl-3-methyl-phenyl)-C-(propyl)-P-(2,6-diheptadecyl-3-methyl-phenyl]phosphoamidinato}{propyl}{ethyl}neodymium; {[N-(2,6-dihexadecyl-phenyl)-C-(propyl)-P-(2,6-dihexadecyl-phenyl)]phosphoamidinato}di-{propyl}samarium; {[N-(2,6-dibutylamino-phenyl)-C-(methyl)-N-(2,6-dibutylamino-phenyl)]amidinato}{propyl}{hydrido}neodymium; {[N-(2,6-ditridecyl-3-diphenylphosphino-phenyl)-C-(ethyl)-N-(2,6-ditridecyl-3-diphenylphosphino-phenyl]amidinato}{propyl}{hydrido}yttrium; {[P-(2,6-dinonyl-4-methyl-phenyl)-C-(chloro)-P-(2,6-dinonyl-4-methyl-phenyl]phosphoamidinato}{undecyl}{ethyl}neodymium; {[N-(2,6-dimethylethylamino-phenyl)-C-(heptyl)-N-(2,6-dimethylethylamino-phenyl)]amidinato}{ethyl}{propyl}samarium; {[N-(2,6-dioctyl-phenyl)-C-(chloro)-P-(2,6-dioctyl-phenyl)]phosphoamidinato}{diethylphosphino}{butyl}neodymium; {[N-(2,6-ditriethylsilylmethyl-phenyl)-C-(ethyl)-N-(2,6-ditriethylsilylmethyl-phenyl)]amidinato}{butyl}{propyl}europium; {[N-(2,6-didecyl-phenyl)-C-(butyl)-N-(2,6-didecyl-phenyl)]amidinato}{hydrido}{ethyl}yttrium; {[N-(2,6-dioctyl-phenyl)-C-(ethyl)-N-(2,6-dioctyl-phenyl)]amidinato}{methyl}{propyl}neodymium; {[N-(2,6-didodecyl-phenyl)-C-(butylamino)-N-(2,6-didodecyl-phenyl)]amidinato}{butyl}{hexyl}yttrium; {[N-(2,6-bis(diethylamino)-phenyl)-C-(butyl)-N-(2,6-bis(diethylamino)-phenyl)]amidinato}{methyl}{butyl}yttrium; {[N-(2,6-didodecyl-phenyl)-C-(hydrido)-N-(2,6-didodecyl-phenyl)]amidinato}{butyl}{propyl}yttrium; {[N-(2,6-bis(dimethylamino)-phenyl)-C-(methyl)-N-(2,6-bis(dimethylamino)-phenyl)]amidinato}{ethyl}{butyl}neodymium; {[N-(2,6-bis(dibutylamino)-phenyl)-C-(propyl)-P-(2,6-bis(dibutylamino)-phenyl)]phosphoamidinato}{butyl}{ethyl}neodymium; {[N-(2,6-diheptadecyl-phenyl)-C-(butyl)-N-(2,6-diheptadecyl-phenyl)]amidinato}{ethyl}{methyl}samarium; {[N-(2,6-diheptyl-phenyl)-C-(ethyl)-N-(2,6-diheptyl-phenyl)]amidinato}{hydrido}{butyl}cerium; {[N-(2,6-dibromo-phenyl)-C-(methyl)-N-(2,6-dibromo-phenyl)]amidinato}{diphenylphosphino}{ethyl}cerium; {[N-(2,6-dipropyl-phenyl)-C-(dibutylamino)-N-(2,6-dipropyl-phenyl)]amidinato}{triethylsilylmethyl}{diphenylphosphino}cerium; {[N-(2,6-di4-methylphenoxy-4-butyl-phenyl)-C-(octyl)-N-(2,6-di4-methylphenoxy-4-butyl-phenyl]amidinato}di-{propyl}yttrium; {[N-(2,6-bis(dimethylamino)-3-octyl-phenyl)-C-(butyl)-N-(2,6-bis(dimethylamino)-3-octyl-phenyl]amidinato}{methyl}{dimethylamino}samarium; {[N-(2,6-dioctadecyl-phenyl)-C-(methyl)-N-(2,6-dioctadecyl-phenyl)]amidinato}{ethyl}{methyl}gadolinium; {[N-(2,6-diheptadecyl-phenyl)-C-(butyl)-N-(2,6-diheptadecyl-phenyl)]amidinato}{ethyl}{dimethylamino}neodymium; {[N-(2,6-ditrimethylsilylethyl-phenyl)-C-(propyl)-N-(2,6-ditrimethylsilylethyl-phenyl)]amidinato}{methyl}{propyl}neodymium; {[N-(2,6-dioctadecyl-phenyl)-C-(tridecyl)-N-(2,6-dioctadecyl-phenyl)]amidinato}di-{ethyl}samarium; {[N-(2,6-dibenzyl-phenyl)-C-(hexadecyl)-N-(2,6-dibenzyl-phenyl)]amidinato}di-{methyl}yttrium; {[N-(2,6-dibutyl-3-nonyl-phenyl)-C-(diphenylphosphino)-N-(2,6-dibutyl-3-nonyl-phenyl]amidinato}{ethyl}{butyl}yttrium; {[N-(2,6-ditetradecyl-phenyl)-C-(tridecyl)-N-(2,6-ditetradecyl-phenyl)]amidinato}{butyl}{propyl}yttrium; {[N-(2,6-bis(dibutylamino)-phenyl)-C-(butyl)-P-(2,6-bis(dibutylamino)-phenyl)]phosphoamidinato}{methyl}{butyl}yttrium; {[N-(2,6-dihexyl-phenyl)-C-(ethyl)-N-(2,6-dihexyl-phenyl)]amidinato}{butyl}{hydrido}neodymium; {[N-(2,6-dipentyl-phenyl)-C-(heptyl)-N-(2,6-dipentyl-phenyl)]amidinato}{methyl}{chloro}yttrium; {[N-(2,6-diheptyl-phenyl)-C-(ethyl)-N-(2,6-diheptyl-phenyl)]amidinato}{ethyl}{butyl}neodymium; {[P-(2,6-dibenzyl-4-ethyl-phenyl)-C-(butylamino)-P-(2,6-dibenzyl-4-ethyl-phenyl]phosphoamidinato}{triethylsilylmethyl}{ethyl}neodymium; {[N-(2,6-ditriethylsilylmethyl-phenyl)-C-(methyl)-N-(2,6-ditriethylsilylmethylphenyl)]amidinato}{phenyl}{ethyl}neodymium; {[P-(2,6-dioctadecyl-phenyl)-C-(butyl)-P-(2,6-dioctadecyl-phenyl)]phosphoamidinato}{methylethylamino}{methyl}yttrium; {[N-(2,6-di4-methylphenoxy-phenyl)-C-(propyl)-N-(2,6-di4-methylphenoxy-phenyl)]amidinato}{butyl}{propyl}neodymium; {[N-(2,6-dichloro-phenyl)-C-(butyl)-N-(2,6-dichloro-phenyl)]amidinato}{ethyl}{dimethylamino}yttrium; {[N-(2,6-diheptadecyl-phenyl)-C-(hydrido)-N-(2,6-diheptadecyl-phenyl)]amidinato}{diphenylphosphino}{methyl}yttrium; {[N-(2,6-ditriethylsilylmethyl-phenyl)-C-(butyl)-N-(2,6-ditriethylsilylmethyl-phenyl)]amidinato}{butyl}{methyl}neodymium; {[N-(2,6-dinonyl-phenyl)-C-(propyl)-N-(2,6-dinonyl-phenyl)]amidinato}{dimethylamino}{nonyl}yttrium; {[P-(2,6-bis(diethylamino)-phenyl)-C-(butyl)-P-(2,6-bis(diethylamino)-phenyl)]phosphoamidinato}{methyl}{undecyl}yttrium; {[N-(2,6-dimethylethylamino-phenyl)-C-(4-methylphenoxy)-N-(2,6-dimethylethylamino-phenyl)]amidinato}{methyl}{heptadecyl}europium; {[N-(2,6-dibutylamino-phenyl)-C-(hydrido)-N-(2,6-dibutylamino-phenyl)]amidinato}{tridecyl}{hydrido}praseodymium; {[P-(2,6-dibenzyl-phenyl)-C-(propyl)-P-(2,6-dibenzyl-phenyl)]phosphoamidinato}{heptyl}{propyl}gadolinium; {[N-(2,6-didecyl-phenyl)-C-(propyl)-P-(2,6-didecyl-phenyl)]phosphoamidinato}{propyl}{ethyl}neodymium; {[N-(2,6-bis(dimethylamino)-phenyl)-C-(methyl)-N-(2,6-bis(dimethylamino)-phenyl)]amidinato}{butyl}{ethyl}neodymium; {[N-(2,6-bis(diethylamino)-phenyl)-C-(butyl)-N-(2,6-bis(diethylamino)-phenyl)]amidinato}{ethyl}{butyl}neodymium; {[N-(2,6-ditridecyl-phenyl)-C-(diethylphosphino)-N-(2,6-ditridecyl-phenyl)]amidinato}{propyl}{methyl}europium; {[N-(2,6-ditriethylsilylmethylphenyl)-C-(ethyl)-N-(2,6-ditriethylsilylmethyl-phenyl)]amidinato}{methyl}{propyl}europium; {[N-(2,6-dimethylethylamino-phenyl)-C-(propyl)-N-(2,6-dimethylethylamino-phenyl)]amidinato}di-{butyl}yttrium; {[N-(2,6-dibenzyl-phenyl)-C-(benzyl)-N-(2,6-dibenzyl-phenyl)]amidinato}{propyl}{butylamino}yttrium; {[N-(2,6-dipentyl-phenyl)-C-(propyl)-N-(2,6-dipentyl-phenyl)]

amidinato}{butyl}{methyl}praseodymium; {[N-(2,6-bis(diethylamino)-phenyl)-C-(methyl)-N-(2,6-bis(diethylamino)-phenyl)]amidinato}{butyl}{ethyl}gadolinium; {[N-(2,6-diundecyl-phenyl)-C-(methyl)-N-(2,6-diundecyl-phenyl)]amidinato}{methyl}{propyl}yttrium; {[N-(2,6-dinonyl-phenyl)-C-(butyl)-N-(2,6-dinonyl-phenyl)]amidinato}{propyl}{butyl}samarium; {[N-(2,6-bis(dibutylamino)-phenyl)-C-(diphenylphosphino)-P-(2,6-bis(dibutylamino)-phenyl)]phosphoamidinato}{butyl}{propyl}neodymium; {[N-(2,6-dibromophenyl)-C-(methyl)-N-(2,6-dibromo-phenyl)]amidinato}{propyl}{butyl}neodymium; {[N-(2,6-ditrimethylsilylethyl-phenyl)-C-(octyl)-N-(2,6-ditrimethylsilylethyl-phenyl)]amidinato}{propyl}{phenyl}europium; {[N-(2,6-dibutyl-phenyl)-C-(ethyl)-N-(2,6-dibutyl-phenyl]amidinato}di-{butyl}yttrium; {[N-(2,6-dinonadecyl-phenyl)-C-(ethyl)-N-(2,6-dinonadecyl-phenyl)]amidinato}{propyl}{butyl}europium; {[N-(2,6-dihexadecyl-phenyl)-C-(ethyl)-N-(2,6-dihexadecyl-phenyl)]amidinato}{propyl}{butyl}yttrium; {[P-(2,6-bis(dibutylamino)-4-propyl-phenyl)-C-(propyl)-P-(2,6-bis(dibutylamino)-4-propyl-phenyl]phosphoamidinato}di-{methyl}neodymium; {[N-(2,6-dibutyl-phenyl)-C-(hydrido)-N-(2,6-dibutyl-phenyl)]amidinato}{ethyl}{perfluorophenyl}praseodymium; {[N-(2,6-dibenzyl-phenyl)-C-(triethylsilylmethyl)-N-(2,6-dibenzyl-phenyl)]amidinato}{methyl}{pentyl}yttrium; {[N-(2,6-dioctyl-phenyl)-C-(methyl)-N-(2,6-dioctyl-phenyl)]amidinato}{propyl}{chloro}yttrium; {[N-(2,6-diheptyl-phenyl)-C-(propyl)-N-(2,6-diheptyl-phenyl)]amidinato}di-{methyl}europium; {[N-(2,6-didecyl-4-propyl-phenyl)-C-(propyl)-N-(2,6-didecyl-4-propyl-phenyl]amidinato}{propyl}{butyl}cerium; {[N-(2,6-bis(dibutylamino)-phenyl)-C-(phenyl)-N-(2,6-bis(dibutylamino)-phenyl)]amidinato}{methyl}{butyl}praseodymium; {[N-(2,6-dibutyl-phenyl)-C-(hydrido)-N-(2,6-dibutyl-phenyl)]amidinato}{ethyl}{methyl}europium; {[N-(2,6-diheptyl-phenyl)-C-(propyl)-N-(2,6-diheptyl-phenyl)]amidinato}{propyl}{4-methylphenoxy}yttrium; {[N-(2,6-dipentadecyl-phenyl)-C-(decyl)-N-(2,6-dipentadecyl-phenyl)]amidinato}di-{methyl}yttrium; {[N-(2,6-dibutylamino-phenyl)-C-(undecyl)-N-(2,6-dibutylamino-phenyl)]amidinato}{butyl}{propyl}praseodymium; {[N-(2,6-bis(diphenylphosphino)-phenyl)-C-(methyl)-N-(2,6-bis(diphenylphosphino)-phenyl)]amidinato}{dimethylamino}{methyl}neodymium; {[N-(2,6-didecyl-phenyl)-C-(dibutylamino)-N-(2,6-didecyl-phenyl)]amidinato}{ethyl}{butyl}praseodymium; {[N-(2,6-dimethylethylamino-phenyl)-C-(methyl)-N-(2,6-dimethylethylamino-phenyl)]amidinato}{phenyl}{undecyl}praseodymium; {[N-(2,6-dinonadecyl-phenyl)-C-(iodo)-N-(2,6-dinonadecyl-phenyl)]amidinato}{ethyl}{propyl}europium; {[N-(2,6-didodecyl-phenyl)-C-(ethyl)-N-(2,6-didodecyl-phenyl)]amidinato}{ethyl}{benzyl}yttrium; {[N-(2,6-dihexadecyl-phenyl)-C-(dimethylamino)-N-(2,6-dihexadecyl-phenyl)]amidinato}{propyl}{hydrido}neodymium; {[N-(2,6-diphenyl-phenyl)-C-(butyl)-N-(2,6-diphenyl-phenyl)]amidinato}{dibutylamino}{ethyl}yttrium; {[N-(2,6-bis(dimethylamino)-4-hydrido-phenyl)-C-(butyl)-N-(2,6-bis(dimethylamino)-4-hydrido-phenyl]amidinato}{propyl}{hydrido}neodymium; {[N-(2,6-diphenyl-phenyl)-C-(methyl)-N-(2,6-diphenyl-phenyl)]amidinato}{ethyl}{methyl}neodymium; {[N-(2,6-dibutyl-phenyl)-C-(propyl)-N-(2,6-dibutyl-phenyl)]amidinato}{propyl}{ethyl}yttrium; {[N-(2,6-dihexyl-phenyl)-C-(butyl)-N-(2,6-dihexyl-phenyl)]amidinato}{methyl}{ethyl}neodymium; {[N-(2,6-bis(diethylamino)-phenyl)-C-(diethylamino)-N-(2,6-bis(diethylamino)-phenyl)]amidinato}{perfluorophenyl}{undecyl}neodymium; {[N-(2,6-bis(dibutylamino)-phenyl)-C-(ethyl)-N-(2,6-bis(dibutylamino)-phenyl)]amidinato}{propyl}{butyl}yttrium; {[N-(2,6-ditetradecyl-4-ethyl-phenyl)-C-(butyl)-P-(2,6-ditetradecyl-4-ethyl-phenyl]phosphoamidinato}{propyl}{octyl}neodymium; {[N-(2,6-diheptadecyl-phenyl)-C-(butyl)-N-(2,6-diheptadecyl-phenyl)]amidinato}{propyl}{dimethylamino}cerium; {[N-(2,6-bis(diethylamino)-phenyl)-C-(butyl)-N-(2,6-bis(diethylamino)-phenyl)]amidinato}{iodo}{butyl}neodymium; {[N-(2,6-dipentadecyl-phenyl)-C-(octadecyl)-N-(2,6-dipentadecyl-phenyl)]amidinato}{propyl}{chloro}neodymium; {[N-(2,6-diiodo-phenyl)-C-(pentyl)-N-(2,6-diiodo-phenyl)]amidinato}{butyl}{ethyl}yttrium; {[P-(2,6-ditrimethylsilylethyl-phenyl)-C-(phenyl)-P-(2,6-ditrimethylsilylethyl-phenyl)]phosphoamidinato}{methyl}{chloro}yttrium; {[N-(2,6-dibutyl-phenyl)-C-(propyl)-N-(2,6-dibutyl-phenyl)]amidinato}{butyl}{propyl}neodymium; {[N-(2,6-ditriethylsilylmethyl-phenyl)-C-(hydrido)-N-(2,6-ditriethylsilylmethyl-phenyl)]amidinato}di-{butyl}samarium; {[N-(2,6-diheptyl-phenyl)-C-(undecyl)-N-(2,6-diheptyl-phenyl)]amidinato}{iodo}{ethyl}neodymium; {[N-(2,6-ditetradecyl-phenyl)-C-(butyl)-N-(2,6-ditetradecyl-phenyl)]amidinato}di-{butyl}cerium; {[N-(2,6-bis(diphenylphosphino)-phenyl)-C-(ethyl)-N-(2,6-bis(diphenylphosphino)-phenyl)]amidinato}{methyl}{propyl}neodymium; {[N-(2,6-dipropyl-phenyl)-C-(methyl)-N-(2,6-dipropyl-phenyl)]amidinato}di-{butyl}europium; {[N-(2,6-dichloro-phenyl)-C-(propyl)-N-(2,6-dichloro-phenyl)]amidinato}{ethyl}{butyl}cerium; {[N-(2,6-ditetradecyl-phenyl)-C-(methyl)-N-(2,6-ditetradecyl-phenyl)]amidinato}{propyl}{hydrido}yttrium; {[N-(2,6-bis(dibutylamino)-3-ethyl-phenyl)-C-(benzyl)-N-(2,6-bis(dibutylamino)-3-ethyl-phenyl]amidinato}di-{butyl}yttrium; {[P-(2,6-bis(diphenylphosphino)-phenyl)-C-(propyl)-P-(2,6-bis(diphenylphosphino)-phenyl)]phosphoamidinato}{butyl}{propyl}yttrium; {[N-(2,6-dihexyl-phenyl)-C-(methyl)-P-(2,6-dihexyl-phenyl)]phosphoamidinato}di-{methyl}samarium; {[N-(2,6-dimethylethylamino-phenyl)-C-(propyl)-N-(2,6-dimethylethylamino-phenyl)]amidinato}{phenyl}{ethyl}samarium; {[N-(2,6-ditetradecyl-phenyl)-C-(methyl)-N-(2,6-ditetradecyl-phenyl)]amidinato}{hydrido}{ethyl}neodymium; {[N-(2,6-bis(diphenylphosphino)-phenyl)-C-(propyl)-N-(2,6-bis(diphenylphosphino)-phenyl)]amidinato}{butyl}{tridecyl}yttrium; {[N-(2,6-bis(diethylamino)-phenyl)-C-(propyl)-N-(2,6-bis(diethylamino)-phenyl)]amidinato}{methyl}{butyl}yttrium; {[N-(2,6-ditetradecyl-phenyl)-C-(ethyl)-N-(2,6-ditetradecyl-phenyl)]amidinato}{benzyl}{tetradecyl}praseodymium; {[P-(2,6-dibenzyl-phenyl)-C-(chloro)-P-(2,6-dibenzyl-phenyl)]phosphoamidinato}{heptyl}{methyl}yttrium; {[N-(2,6-diheptadecyl-3-hydrido-phenyl)-C-(ethyl)-N-(2,6-diheptadecyl-3-hydrido-phenyl]

amidinato}{hexyl}{heptyl}praseodymium; {[N-(2,6-dipentadecyl-phenyl)-C-(pentadecyl)-N-(2,6-dipentadecyl-phenyl)]amidinato}{ethyl}{diethylamino}neodymium; {[N-(2,6-ditetradecyl-phenyl)-C-(pentyl)-N-(2,6-ditetradecyl-phenyl)]amidinato}{propyl}{nonyl}cerium; {[N-(2,6-didodecyl-4-phenyl-phenyl)-C-(butyl)-N-(2,6-didodecyl-4-phenyl-phenyl]amidinato}di-{ethyl}neodymium; {[N-(2,6-bis(diethylamino)-4-hydrido-phenyl)-C-(butyl)-N-(2,6-bis(diethylamino)-4-hydrido-phenyl]amidinato}{propyl}{methyl}yttrium; {[N-(2,6-bis(diethylamino)-phenyl)-C-(propyl)-N-(2,6-bis(diethylamino)-phenyl)]amidinato}{butyl}{methyl}yttrium; {[N-(2,6-ditetradecyl-phenyl)-C-(ethyl)-N-(2,6-ditetradecyl-phenyl)]amidinato}{diethylamino}{ethyl}yttrium; {[N-(2,6-bis(dibutylamino)-phenyl)-C-(ethyl)-N-(2,6-bis(dibutylamino)-phenyl)]amidinato}{hydrido}{propyl}cerium; {[N-(2,6-diheptadecyl-phenyl)-C-(4-methylphenoxy)-N-(2,6-diheptadecyl-phenyl)]amidinato}{propyl}{butyl}yttrium; {[N-(2,6-di4-methylphenoxy-phenyl)-C-(octadecyl)-N-(2,6-di4-methylphenoxy-phenyl)]amidinato}{butyl}{decyl}gadolinium; {[N-(2,6-bis(diphenylphosphino)-phenyl)-C-(butyl)-N-(2,6-bis(diphenylphosphino)-phenyl)]amidinato}{ethyl}{propyl}yttrium; {[N-(2,6-ditriethylsilylmethyl-3-butyl-phenyl)-C-(ethyl)-N-(2,6-ditriethylsilylmethyl-3-butyl-phenyl]amidinato}{propyl}{butyl}yttrium; {[N-(2,6-ditrimethylsilylethyl-phenyl)-C-(butyl)-N-(2,6-ditrimethylsilylethyl-phenyl)]amidinato}{triethylsilylmethyl}{ethyl}neodymium; {[N-(2,6-ditriethylsilylmethyl-phenyl)-C-(bromo)-N-(2,6-ditriethylsilylmethyl-phenyl)]amidinato}{diethylamino}{ethyl}yttrium; {[N-(2,6-ditridecyl-phenyl)-C-(butyl)-N-(2,6-ditridecyl-phenyl)]amidinato}{methyl}{ethyl}samarium; {[N-(2,6-diheptyl-phenyl)-C-(propyl)-N-(2,6-diheptyl-phenyl)]amidinato}{butyl}{propyl}neodymium; {[N-(2,6-ditetradecyl-phenyl)-C-(ethyl)-N-(2,6-ditetradecyl-phenyl)]amidinato}{butyl}{ethyl}yttrium; {[N-(2,6-dibromo-phenyl)-C-(methyl)-N-(2,6-dibromo-phenyl)]amidinato}{hydrido}{ethyl}cerium; {[N-(2,6-dichloro-phenyl)-C-(ethyl)-N-(2,6-dichloro-phenyl)]amidinato}{butyl}{propyl}neodymium; {[N-(2,6-bis(diphenylphosphino)-phenyl)-C-(methyl)-N-(2,6-bis(diphenylphosphino)-phenyl)]amidinato}{perfluorophenyl}{methyl}neodymium; {[N-(2,6-diundecyl-phenyl)-C-(ethyl)-N-(2,6-diundecyl-phenyl)]amidinato}{nonyl}{methyl}yttrium; {[N-(2,6-diundecyl-phenyl)-C-(hexadecyl)-N-(2,6-diundecyl-phenyl)]amidinato}{diphenylphosphino}{propyl}neodymium; {[N-(2,6-diheptadecyl-phenyl)-C-(propyl)-P-(2,6-diheptadecyl-phenyl)]phosphoamidinato}{methyl}{butyl}yttrium; {[N-(2,6-dioctadecyl-phenyl)-C-(methyl)-N-(2,6-dioctadecyl-phenyl)]amidinato}{4-methylphenoxy}{methyl}neodymium; {[P-(2,6-bis(diphenylphosphino)-phenyl)-C-(butyl)-P-(2,6-bis(diphenylphosphino)-phenyl)]phosphoamidinato}{butyl}{methyl}neodymium; {[P-(2,6-dibutyl-phenyl)-C-(octadecyl)-P-(2,6-dibutyl-phenyl)]phosphoamidinato}{diethylphosphino}{chloro}cerium; {[N-(2,6-dipropyl-phenyl)-C-(propyl)-N-(2,6-dipropyl-phenyl)]amidinato}{propyl}{iodo}yttrium; {[N-(2,6-dioctyl-phenyl)-C-(heptyl)-N-(2,6-dioctyl-phenyl)]amidinato}{tridecyl}{undecyl}gadolinium; {[N-(2,6-dinonyl-3-butyl-phenyl)-C-(diethylamino)-N-(2,6-dinonyl-3-butyl-phenyl]amidinato}{undecyl}{ethyl}neodymium; {[P-(2,6-dinonyl-4-methyl-phenyl)-C-(ethyl)-P-(2,6-dinonyl-4-methyl-phenyl)]phosphoamidinato}{propyl}{hydrido}yttrium; {[N-(2,6-ditetradecyl-phenyl)-C-(ethyl)-N-(2,6-ditetradecyl-phenyl)]amidinato}{undecyl}{ethyl}neodymium; {[N-(2,6-diheptyl-phenyl)-C-(propyl)-N-(2,6-diheptyl-phenyl)]amidinato}{hydrido}{ethyl}neodymium; {[N-(2,6-didecyl-phenyl)-C-(butyl)-N-(2,6-didecyl-phenyl)]amidinato}{butyl}{methyl}neodymium; {[N-(2,6-dioctyl-phenyl)-C-(hydrido)-N-(2,6-dioctyl-phenyl)]amidinato}{butyl}{methyl}yttrium; {[N-(2,6-dinonadecyl-phenyl)-C-(butyl)-N-(2,6-dinonadecyl-phenyl)]amidinato}di-{hydrido}yttrium; {[N-(2,6-dihexyl-phenyl)-C-(propyl)-N-(2,6-dihexyl-phenyl)]amidinato}{methyl}{butyl}neodymium; {[N-(2,6-dipropyl-phenyl)-C-(methyl)-N-(2,6-dipropyl-phenyl)]amidinato}{octyl}{methyl}yttrium; {[N-(2,6-ditetradecyl-4-propyl-phenyl)-C-(butyl)-N-(2,6-ditetradecyl-4-propyl-phenyl]amidinato}di-{propyl}yttrium; {[N-(2,6-ditridecyl-phenyl)-C-(propyl)-N-(2,6-ditridecyl-phenyl)]amidinato}{methyl}{decyl}yttrium; {[N-(2,6-dioctadecyl-phenyl)-C-(hydrido)-N-(2,6-dioctadecyl-phenyl)]amidinato}{hydrido}{ethyl}yttrium; {[N-(2,6-ditrimethylsilylethyl-phenyl)-C-(methyl)-N-(2,6-ditrimethylsilylethyl-phenyl)]amidinato}di-{ethyl}neodymium; {[N-(2,6-di4-methylphenoxy-phenyl)-C-(heptyl)-N-(2,6-di4-methylphenoxy-phenyl)]amidinato}{ethyl}{pentyl}yttrium; {[N-(2,6-dinonadecyl-4-propyl-phenyl)-C-(propyl)-N-(2,6-dinonadecyl-4-propyl-phenyl]amidinato}{hexadecyl}{propyl}yttrium; {[N-(2,6-bis(dimethylamino)-phenyl)-C-(decyl)-N-(2,6-bis(dimethylamino)-phenyl)]amidinato}{butyl}{propyl}yttrium; {[N-(2,6-diheptadecyl-phenyl)-C-(hydrido)-N-(2,6-diheptadecyl-phenyl)]amidinato}di-{butyl}yttrium; {[N-(2,6-dihexyl-phenyl)-C-(propyl)-P-(2,6-dihexyl-phenyl)]phosphoamidinato}{butyl}{ethyl}neodymium; {[N-(2,6-bis(dibutylamino)-phenyl)-C-(octadecyl)-N-(2,6-bis(dibutylamino)-phenyl)]amidinato}{ethyl}{phenyl}samarium; {[N-(2,6-bis(dimethylamino)-phenyl)-C-(bromo)-N-(2,6-bis(dimethylamino)-phenyl)]amidinato}{ethyl}{dodecyl}samarium; {[N-(2,6-di4-methylphenoxy-phenyl)-C-(hydrido)-N-(2,6-di4-methylphenoxy-phenyl)]amidinato}{ethyl}{propyl}gadolinium; {[N-(2,6-dihexyl-phenyl)-C-(propyl)-N-(2,6-dihexyl-phenyl)]amidinato}di-{ethyl}praseodymium; {[N-(2,6-dibutyl-phenyl)-C-(ethyl)-P-(2,6-dibutyl-phenyl)]phosphoamidinato}{methyl}{tetradecyl}europium; {[N-(2,6-dipentadecyl-phenyl)-C-(perfluorophenyl)-N-(2,6-dipentadecyl-phenyl)]amidinato}{nonyl}{diphenylphosphino}neodymium; {[N-(2,6-bis(dimethylamino)-phenyl)-C-(methyl)-N-(2,6-bis(dimethylamino)-phenyl)]amidinato}{tridecyl}{propyl}yttrium; {[N-(2,6-dinonyl-phenyl)-C-(butyl)-N-(2,6-dinonyl-phenyl)]amidinato}{butyl}{propyl}samarium; {[N-(2,6-diheptyl-4-phenyl-phenyl)-C-(methyl)-N-(2,6-diheptyl-4-phenyl-phenyl]amidinato}{propyl}{ethyl}yttrium; {[P-(2,6-bis(diphenylphosphino)-phenyl)-C-(propyl)-P-(2,6-bis(diphenylphosphino)-phenyl)]phosphoamidinato}{chloro}{propyl}cerium; {[N-(2,6-diundecyl-phenyl)-C-(methyl)-N-(2,6-diundecyl-phenyl)]amidinato}{ethyl}{methyl}gadolinium; {[N-(2,6-dioctylphenyl)-C-(butyl)-N-(2,6-dioctyl-phenyl)]amidinato}di-{methyl}gadolinium; {[N-(2,6-dimethylethylamino-phenyl)-C-(butyl)-N-(2,6-dimethylethylamino-phenyl)]amidinato}{butyl}{hydrido}neodymium; {[N-(2,6-diheptadecyl-phenyl)-C-(iodo)-N-(2,6-diheptadecyl-phenyl)]amidinato}{dibutylamino}{ethyl}yttrium; {[N-(2,6-dibutyl-phenyl)-C-(diphenylphosphino)-N-(2,6-dibutyl-phenyl)]amidinato}{ethyl}{propyl}yttrium; {[N-(2,6-dihexadecyl-phenyl)-C-(4-methylphenoxy)-N-(2,6-dihexadecyl-phenyl)]amidinato}{iodo}{propyl}neodymium; {[N-(2,6-ditrimethylsilylethyl-phenyl)-C-(chloro)-N-(2,6-ditrimethylsilylethyl-phenyl)]amidinato}di-{methyl}yttrium; {[N-(2,6-dioctadecyl-phenyl)-C-(butyl)-N-(2,6-dioctadecyl-phenyl)]amidinato}{methyl}{benzyl}yttrium; {[N-(2,6-di4-methylphenoxy-phenyl)-C-(methyl)-N-(2,6-di4-methylphenoxy-phenyl)]amidinato}{ethyl}{octyl}samarium; {[N-(2,6-dibromo-phenyl)-C-(triethylsilylmethyl)-N-(2,6-dibromo-phenyl)]amidinato}{methyl}{propyl}yttrium; {[N-(2,6-bis(dibutylamino)-phenyl)-C-(methyl)-N-(2,6-bis(dibutylamino)-phenyl)]amidinato}{ethyl}{decyl}gadolinium; {[N-(2,6-dihexyl-phenyl)-C-(propyl)-N-(2,6-dihexyl-phenyl)]amidinato}{ethyl}{methyl}neodymium; {[P-(2,6-di4-methylphenoxy-phenyl)-C-(ethyl)-P-(2,6-di4-methylphenoxy-phenyl)]phosphoamidinato}{ethyl}{propyl}praseodymium; {[N-(2,6-ditrimethylsilylethyl-phenyl)-C-(propyl)-N-(2,6-ditrimethylsilylethyl-phenyl)]amidinato}{methyl}{dodecyl}cerium; {[P-(2,6-bis(diethylamino)-phenyl)-C-(ethyl)-P-(2,6-bis(diethylamino)-phenyl)]phosphoamidinato}{hexyl}{ethyl}yttrium; {[N-(2,6-didodecyl-phenyl)-C-(ethyl)-N-(2,6-didodecyl-phenyl)]amidinato}{methyl}{butyl}yttrium; {[P-(2,6-dinonyl-phenyl)-C-(butyl)-P-(2,6-dinonyl-phenyl)]phosphoamidinato}{iodo}{ethyl}yttrium; {[N-(2,6-dioctyl-phenyl)-C-(ethyl)-N-(2,6-dioctyl-phenyl)]amidinato}{ethyl}{dibutylamino}yttrium; {[N-(2,6-dioctyl-phenyl)-C-(ethyl)-N-(2,6-dioctyl-phenyl)]amidinato}{undecyl}{butyl}samarium; {[N-(2,6-dichloro-phenyl)-C-(heptadecyl)-N-(2,6-dichloro-phenyl)]amidinato}{hydrido}{{[N-(2,6-dipropyl-4-propyl-phenyl)-C-(methyl)-N-(2,6-dipropyl-4-propyl-phenyl)]amidinato}{butyl}{bromo}praseodymium; {[N-(2,6-bis(dibutylamino)-phenyl)-C-(butyl)-N-(2,6-bis(dibutylamino)-phenyl)]amidinato}di-{propyl}cerium; {[N-(2,6-didodecyl-phenyl)-C-(tridecyl)-P-(2,6-didodecyl-phenyl)]phosphoamidinato}{methyl}{perfluorophenyl}yttrium; {[P-(2,6-dioctyl-phenyl)-C-(bromo)-P-(2,6-dioctyl-phenyl)]phosphoamidinato}{ethyl}{propyl}yttrium; {[N-(2,6-bis(diethylamino)-phenyl)-C-(propyl)-N-(2,6-bis(diethylamino)-phenyl)]amidinato}{butyl}{ethyl}cerium; {[N-(2,6-bis(dimethylamino)-phenyl)-C-(propyl)-N-(2,6-bis(dimethylamino)-phenyl)]amidinato}{phenyl}{dimethylamino}gadolinium; {[N-(2,6-dioctadecyl-phenyl)-C-(butyl)-N-(2,6-dioctadecyl-phenyl)]amidinato}{butyl}{chloro}yttrium; {[N-(2,6-bis(diphenylphosphino)-phenyl)-C-(propyl)-N-(2,6-bis(diphenylphosphino)-phenyl)]amidinato}{ethyl}{butyl}neodymium; {[N-(2,6-dinonyl-4-methyl-phenyl)-C-(propyl)-N-(2,6-dinonyl-4-methyl-phenyl]amidinato}{tridecyl}{ethyl}europium; {[N-(2,6-bis(diethylamino)-phenyl)-C-(hydrido)-N-(2,6-bis(diethylamino)-phenyl)]amidinato}{tridecyl}{ethyl}cerium; {[N-(2,6-dipropyl-phenyl)-C-(iodo)-N-(2,6-dipropyl-phenyl)]amidinato}di-{propyl}neodymium; {[N-(2,6-dibutyl-phenyl)-C-(methyl)-N-(2,6-dibutyl-phenyl)]amidinato}{methylethylamino}{butyl}neodymium; {[N-(2,6-dioctyl-phenyl)-C-(butyl)-N-(2,6-dioctyl-phenyl)]amidinato}{propyl}{chloro}praseodymium; {[N-(2,6-bis(diphenylphosphino)-phenyl)-C-(ethyl)-N-(2,6-bis(diphenylphosphino)-phenyl)]amidinato}di-{propyl}yttrium; {[P-(2,6-diheptadecyl-phenyl)-C-(methyl)-P-(2,6-diheptadecyl-phenyl)]phosphoamidinato}{4-methylphenoxy}{propyl}gadolinium; {[N-(2,6-dioctadecyl-4-hydrido-phenyl)-C-(phenyl)-P-(2,6-dioctadecyl-4-hydrido-phenyl]phosphoamidinato}{propyl}{heptyl}cerium; {[N-(2,6-diiodo-phenyl)-C-(diphenylphosphino)-N-(2,6-diiodo-phenyl)]amidinato}{ethyl}{hydrido}yttrium; {[N-(2,6-ditriethylsilylmethyl-phenyl)-C-(propyl)-N-(2,6-ditriethylsilylmethyl-phenyl)]amidinato}{methyl}{butyl}neodymium; {[N-(2,6-dioctyl-phenyl)-C-(propyl)-N-(2,6-dioctyl-phenyl)]amidinato}{propyl}{decyl}cerium; {[N-(2,6-bis(diphenylphosphino)-phenyl)-C-(butyl)-P-(2,6-bis(diphenylphosphino)-phenyl)]phosphoamidinato}{butyl}{propyl}neodymium; {[N-(2,6-dipropyl-phenyl)-C-(methyl)-N-(2,6-dipropyl-phenyl)]amidinato}{hydrido}{butyl}neodymium; {[N-(2,6-dichloro-phenyl)-C-(phenyl)-N-(2,6-dichloro-phenyl)]amidinato}{hydrido}{methyl}cerium; {[N-(2,6-dinonyl-phenyl)-C-(ethyl)-N-(2,6-dinonyl-phenyl)]amidinato}{octyl}{ethyl}neodymium; {[N-(2,6-dibutylamino-phenyl)-C-(propyl)-N-(2,6-dibutylamino-phenyl)]amidinato}{pentyl}{ethyl}yttrium; {[N-(2,6-dichloro-phenyl)-C-(ethyl)-N-(2,6-dichloro-phenyl)]amidinato}{hexadecyl}{propyl}gadolinium; {[N-(2,6-ditridecyl-phenyl)-C-(diethylamino)-P-(2,6-ditridecyl-phenyl)]phosphoamidinato}di-{hexadecyl}praseodymium; {[N-(2,6-bis(diethylamino)-phenyl)-C-(chloro)-N-(2,6-bis(diethylamino)-phenyl)]amidinato}{benzyl}{perfluorophenyl}gadolinium; {[N-(2,6-didodecyl-phenyl)-C-(decyl)-N-(2,6-didodecyl-phenyl)]amidinato}{dodecyl}{methylethylamino}neodymium; {[N-(2,6-diundecyl-phenyl)-C-(methyl)-N-(2,6-diundecyl-phenyl)]amidinato}{hydrido}{butyl}yttrium; {[N-(2,6-dinonyl-phenyl)-C-(ethyl)-P-(2,6-dinonyl-phenyl)]phosphoamidinato}{hexadecyl}{dimethylamino}gadolinium; {[N-(2,6-dipropyl-phenyl)-C-(methyl)-N-(2,6-dipropyl-phenyl)]amidinato}{propyl}{chloro}gadolinium; {[N-(2,6-diiodo-phenyl)-C-(propyl)-N-(2,6-diiodo-phenyl)]amidinato}{pentyl}{phenyl}neodymium; {[N-(2,6-dinonyl-phenyl)-C-(dodecyl)-N-(2,6-dinonyl-phenyl)]amidinato}{ethyl}{butyl}neodymium; {[N-(2,6-ditridecyl-phenyl)-C-(propyl)-N-(2,6-ditridecyl-phenyl)]amidinato}{butyl}{iodo}europium; {[P-(2,6-diiodo-phenyl)-C-(butyl)-P-(2,6-diiodo-phenyl)]phosphoamidinato}di-{butyl}yttrium; {[N-(2,6-dioctyl-phenyl)-C-(hydrido)-N-(2,6-dioctyl-phenyl)]amidinato}di-{propyl}yttrium; {[N-(2,6-ditriethylsilylmethyl-4-hydrido-phenyl)-C-(methyl)-N-(2,6-ditriethylsilylmethyl-4-hydrido-phenyl]amidinato}{ethyl}{butyl}neodymium; {[N-(2,6-diphenyl-phenyl)-C-(heptyl)-N-(2,6-diphenyl-phenyl)]amidinato}{hydrido}{propyl}yttrium; {[N-(2,6-diheptyl-phenyl)-C-(propyl)-N-(2,6-diheptyl-phenyl)]amidinato}{chloro}{propyl}neodymium; {[N-(2,6-ditriethylsilylmethyl-phenyl)-C-(propyl)-N-(2,6-ditriethylsilylmethyl-phenyl)]

amidinato}{butyl}{propyl}cerium; {[N-(2,6-didodecyl-phenyl)-C-(butyl)-N-(2,6-didodecyl-phenyl)]amidinato}di-{methyl}yttrium; {[N-(2,6-di4-methylphenoxy-phenyl)-C-(propyl)-N-(2,6-di4-methylphenoxy-phenyl)]amidinato}{methyl}{pentadecyl}neodymium; {[N-(2,6-dihexyl-4-chloro-phenyl)-C-(butyl)-N-(2,6-dihexyl-4-chloro-phenyl]amidinato}{ethyl}{triethylsilylmethyl}yttrium; {[P-(2,6-bis(dibutylamino)-phenyl)-C-(chloro)-P-(2,6-bis(dibutylamino)-phenyl)]phosphoamidinato}{dimethylamino}{diphenylphosphino}neodymium; {[N-(2,6-bis(diethylamino)-phenyl)-C-(butyl)-N-(2,6-bis(diethylamino)-phenyl)]amidinato}{butyl}{ethyl}neodymium; {[N-(2,6-bis(diphenylphosphino)-phenyl)-C-(iodo)-N-(2,6-bis(diphenylphosphino)-phenyl)]amidinato}di-{methyl}yttrium; {[N-(2,6-dibromo-phenyl)-C-(perfluorophenyl)-N-(2,6-dibromo-phenyl)]amidinato}{butyl}{ethyl}yttrium; {[N-(2,6-didecyl-phenyl)-C-(iodo)-N-(2,6-didecyl-phenyl)]amidinato}{propyl}{methyl}yttrium; {[N-(2,6-dinonyl-phenyl)-C-(octyl)-N-(2,6-dinonyl-phenyl)]amidinato}{hexadecyl}{propyl}gadolinium; {[N-(2,6-dipentyl-4-propyl-phenyl)-C-(butyl)- {[N-(2,6-bis(diphenylphosphino)-phenyl)-C-(propyl)-N-(2,6-bis(diphenylphosphino)-phenyl)]amidinato}di-{methyl}yttrium; {[N-(2,6-dichloro-phenyl)-C-(hydrido)-N-(2,6-dichloro-phenyl)]amidinato}{propyl}{ethyl}neodymium; {[N-(2,6-diiodo-4-ethyl-phenyl)-C-(ethyl)-N-(2,6-diiodo-4-ethyl-phenyl]amidinato}{propyl}{ethyl}samarium; {[N-(2,6-dibutyl-phenyl)-C-(ethyl)-N-(2,6-dibutyl-phenyl)]amidinato}di-{hydrido}europium; {[N-(2,6-dibromo-phenyl)-C-(ethyl)-N-(2,6-dibromo-phenyl)]amidinato}di-{propyl}yttrium; {[N-(2,6-diundecyl-phenyl)-C-(pentadecyl)-N-(2,6-diundecyl-phenyl)]amidinato}di-{undecyl}neodymium; {[N-(2,6-diheptadecyl-3-hydrido-phenyl)-C-(dibutylamino)-N-(2,6-diheptadecyl-3-hydrido-phenyl]amidinato}di-{butyl}yttrium; {[N-(2,6-diheptadecyl-phenyl)-C-(hydrido)-N-(2,6-diheptadecyl-phenyl)]amidinato}di-{methyl}yttrium; {[N-(2,6-dipentadecyl-3-propyl-phenyl)-C-(methyl)-N-(2,6-dipentadecyl-3-propyl-phenyl]amidinato}di-{benzyl}yttrium; {[N-(2,6-diphenyl-phenyl)-C-(butyl)-P-(2,6-diphenyl-phenyl)]phosphoamidinato}di-{ethyl}neodymium; {[N-(2,6-ditridecyl-3-ethyl-phenyl)-C-(butyl)-P-(2,6-ditridecyl-3-ethyl-phenyl]phosphoamidinato}di-{butyl}yttrium; {[N-(2,6-dibromo-phenyl)-C-(dodecyl)-N-(2,6-dibromo-phenyl)]amidinato}di-{octyl}yttrium; {[N-(2,6-ditriethylsilylmethyl-phenyl)-C-(chloro)-N-(2,6-ditriethylsilylmethyl-phenyl)]amidinato}di-{methyl}samarium; {[N-(2,6-diiodo-phenyl)-C-(methyl)-N-(2,6-diiodo-phenyl)]amidinato}di-{methyl}gadolinium; {[N-(2,6-dipentyl-phenyl)-C-(propyl)-N-(2,6-dipentyl-phenyl)]amidinato}di-{propyl}neodymium; {[N-(2,6-diundecyl-phenyl)-C-(ethyl)-P-(2,6-diundecyl-phenyl)]phosphoamidinato}di-{octyl}yttrium; {[N-(2,6-dihexyl-phenyl)-C-(methyl)-N-(2,6-dihexyl-phenyl)]amidinato}di-{phenyl}yttrium; {[N-(2,6-ditrimethylsilylethyl-phenyl)-C-(methyl)-N-(2,6-ditrimethylsilylethyl-phenyl)]amidinato}di-{ethyl}neodymium; {[N-(2,6-dihexadecyl-phenyl)-C-(propyl)-P-(2,6-dihexadecyl-phenyl)]phosphoamidinato}di-{diphenylphosphino}praseodymium; {[N-(2,6-dipentadecyl-phenyl)-C-(butyl)-P-(2,6-dipentadecyl-phenyl)]phosphoamidinato}di-{butyl}neodymium; {[N-(2,6-dipentadecyl-4-ethyl-phenyl)-C-(methyl)-P-(2,6-dipentadecyl-4-ethyl-phenyl)phosphoamidinato}di-{perfluorophenyl}praseodymium; {[N-(2,6-ditetradecyl-phenyl)-C-(butyl)-N-(2,6-ditetradecyl-phenyl)]amidinato}di-{propyl}neodymium; {[N-(2,6-dibutylamino-phenyl)-C-(butyl)-N-(2,6-dibutylamino-phenyl)]amidinato}di-{tetradecyl}neodymium; {[N-(2,6-dioctyl-phenyl)-C-(butyl)-N-(2,6-dioctyl-phenyl)]amidinato}di-{propyl}neodymium; {[N-(2,6-di4-methylphenoxy-phenyl)-C-(ethyl)-N-(2,6-di4-methylphenoxy-phenyl)]amidinato}di-{4-methylphenoxy}yttrium; {[N-(2,6-dipentyl-phenyl)-C-(diphenylphosphino)-N-(2,6-dipentyl-phenyl)]amidinato}di-{propyl}neodymium; {[N-(2,6-dipentadecyl-phenyl)-C-(diethylamino)-P-(2,6-dipentadecyl-phenyl)]phosphoamidinato}di-{propyl}yttrium; {[N-(2,6-bis(dimethylamino)-phenyl)-C-(triethylsilylmethyl)-N-(2,6-bis(dimethylamino)-phenyl)]amidinato}di-{butyl}neodymium; {[N-(2,6-dimethylethylamino-phenyl)-C-(ethyl)-N-(2,6-dimethylethylamino-phenyl)]amidinato}di-{butyl}europium; {[N-(2,6-dipentadecyl-phenyl)-C-(propyl)-N-(2,6-dipentadecyl-phenyl)]amidinato}di-{ethyl}samarium; {[N-(2,6-dioctadecyl-phenyl)-C-(octadecyl)-N-(2,6-dioctadecyl-phenyl)]amidinato}di-{methyl}neodymium; {[N-(2,6-diiodo-phenyl)-C-(hexyl)-N-(2,6-diiodo-phenyl)]amidinato}di-{propyl}neodymium; {[P-(2,6-ditriethylsilylmethyl-phenyl)-C-(propyl)-P-(2,6-ditriethylsilylmethyl-phenyl)]phosphoamidinato}di-{ethyl}neodymium; {[N-(2,6-diundecyl-phenyl)-C-(propyl)-N-(2,6-diundecyl-phenyl)]amidinato}di-{ethyl}cerium; {[N-(2,6-bis(diethylamino)-phenyl)-C-(ethyl)-N-(2,6-bis(diethylamino)-phenyl)]amidinato}di-{methyl}yttrium; {[N-(2,6-ditrimethylsilylethyl-phenyl)-C-(butyl)-N-(2,6-ditrimethylsilylethyl-phenyl)]amidinato}di-{propyl}yttrium; {[N-(2,6-dinonyl-phenyl)-C-(methyl)-N-(2,6-dinonyl-phenyl)]amidinato}di-{ethyl}neodymium; {[N-(2,6-dioctyl-phenyl)-C-(hydrido)-N-(2,6-dioctyl-phenyl)]amidinato}di-{ethyl}yttrium; {[N-(2,6-bis(dibutylamino)-phenyl)-C-(chloro)-N-(2,6-bis(dibutylamino)-phenyl)]amidinato}di-{ethyl}europium; {[N-(2,6-diundecyl-phenyl)-C-(methyl)-N-(2,6-diundecyl-phenyl)]amidinato}di-{propyl}yttrium; {[N-(2,6-dipentyl-4-propyl-phenyl)-C-(ethyl)-N-(2,6-dipentyl-4-propyl-phenyl]amidinato}di-{propyl}praseodymium; {[N-(2,6-diiodo-phenyl)-C-(propyl)-N-(2,6-diiodo-phenyl)]amidinato}di-{butyl}neodymium; {[N-(2,6-bis(dibutylamino)-phenyl)-C-(hydrido)-N-(2,6-bis(dibutylamino)-phenyl)]amidinato}di-{propyl}neodymium; {[N-(2,6-di4-methylphenoxy-phenyl)-C-(propyl)-N-(2,6-di4-methylphenoxy-phenyl)]amidinato}di-{propyl}yttrium; {[N-(2,6-bis(diphenylphosphino)-3-butyl-phenyl)-C-(propyl)-P-(2,6-bis(diphenylphosphino)-3-butyl-phenyl]phosphoamidinato}di-{butyl}neodymium; {[N-(2,6-diundecyl-phenyl)-C-(hydrido)-N-(2,6-diundecyl-phenyl)]amidinato}di-{propyl}samarium; {[N-(2,6-dioctadecyl-phenyl)-C-(butyl)-N-(2,6-dioctadecyl-phenyl)]amidinato}di-{propyl}praseodymium; {[N-(2,6-ditetradecyl-phenyl)-C-(propyl)-N-(2,6-ditetradecyl-phenyl)]amidinato}di-{methyl}cerium; {[N-(2,6-dioctadecyl-phenyl)-C-(hydrido)-N-(2,6-dioctadecyl-phenyl)]amidinato}di-{phenyl}samarium; {[N-(2,6-dinonyl-phenyl)-C-(ethyl)-N-(2,6-dinonyl-phenyl)]amidinato}di-{butyl}europium; {[N-(2,6-dipentyl-phenyl)-C-(methyl)-N-(2,6-dipentyl-phenyl)]amidinato}di-{methyl}yttrium; {[N-(2,6-dioctyl-phenyl)-C-(ethyl)-N-(2,6-dioctyl-phenyl)]amidinato}di-{phenyl}yttrium; {[N-(2,6-dipropyl-phenyl)-C-(hydrido)-N-(2,6-dipropyl-phenyl)]amidinato}di-{ethyl}yttrium; {[N-(2,6-didecyl-phenyl)-C-

(methyl)-N-(2,6-didecyl-phenyl)]amidinato}di-{butyl}yttrium; {[N-(2,6-diheptadecyl-4-ethyl-phenyl)-C-(ethyl)-N-(2,6-diheptadecyl-4-ethyl-phenyl]amidinato}di-{butyl}neodymium; {[N-(2,6-diiodo-phenyl)-C-(propyl)-N-(2,6-diiodo-phenyl)]amidinato}di-{ethyl}neodymium; {[N-(2,6-dihexadecyl-3-propyl-phenyl)-C-(propyl)-N-(2,6-dihexadecyl-3-propyl-phenyl]amidinato}di-{propyl}yttrium; {[N-(2,6-ditridecyl-phenyl)-C-(propyl)-N-(2,6-ditridecyl-phenyl)]amidinato}di-{butyl}neodymium; {[N-(2,6-ditrimethylsilylethyl-phenyl)-C-(nonyl)-N-(2,6-ditrimethylsilylethyl-phenyl)]amidinato}di-{methyl}praseodymium; {[N-(2,6-ditriethylsilylmethyl-phenyl)-C-(propyl)-N-(2,6-ditriethylsilylmethyl-phenyl)]amidinato}di-{nonyl}yttrium; {[N-(2,6-dinonyl-phenyl)-C-(ethyl)-N-(2,6-dinonyl-phenyl)]amidinato}di-{propyl}europium; {[N-(2,6-dibutylamino-phenyl)-C-(hydrido)-N-(2,6-dibutylamino-phenyl)]amidinato}di-{ethyl}samarium; {[N-(2,6-diphenyl-phenyl)-C-(methyl)-N-(2,6-diphenyl-phenyl)]amidinato}di-{ethyl}yttrium; {[N-(2,6-didecyl-phenyl)-C-(hydrido)-N-(2,6-didecyl-phenyl)]amidinato}di-{methyl}yttrium; {[N-(2,6-ditrimethylsilylethyl-phenyl)-C-(propyl)-N-(2,6-ditrimethylsilylethyl-phenyl)]amidinato}di-{heptadecyl}praseodymium; {[N-(2,6-didodecyl-phenyl)-C-(iodo)-N-(2,6-didodecyl-phenyl)]amidinato}di-{heptyl}yttrium; {[N-(2,6-dipropyl-phenyl)-C-(iodo)-N-(2,6-dipropyl-phenyl)]amidinato}di-{diethylamino}yttrium; {[N-(2,6-dinonyl-phenyl)-C-(heptadecyl)-N-(2,6-dinonyl-phenyl)]amidinato}di-{octadecyl}yttrium; {[N-(2,6-dihexyl-phenyl)-C-(methyl)-N-(2,6-dihexyl-phenyl)]amidinato}di-{butyl}gadolinium; {[N-(2,6-didodecyl-4-methyl-phenyl)-C-(propyl)-P-(2,6-didodecyl-4-methyl-phenyl]phosphoamidinato}di-{dibutylamino}neodymium; {[N-(2,6-dipentyl-phenyl)-C-(propyl)-N-(2,6-dipentyl-phenyl)]amidinato}di-{methyl}gadolinium; {[N-(2,6-ditrimethylsilylethyl-phenyl)-C-(ethyl)-N-(2,6-ditrimethylsilylethyl-phenyl]amidinato}di-{ethyl}yttrium; {[P-(2,6-diheptadecyl-phenyl)-C-(propyl)-P-(2,6-diheptadecyl-phenyl)]phosphoamidinato}di-{methyl}neodymium; {[N-(2,6-diheptadecyl-phenyl)-C-(heptadecyl)-N-(2,6-diheptadecyl-phenyl)]amidinato}di-{propyl}praseodymium; {[N-(2,6-ditetradecyl-phenyl)-C-(4-methylphenoxy)-N-(2,6-ditetradecyl-phenyl)]amidinato}di-{chloro}yttrium; {[N-(2,6-diundecyl-phenyl)-C-(propyl)-N-(2,6-diundecyl-phenyl)]amidinato}di-{methyl}neodymium; {[N-(2,6-dinonadecyl-phenyl)-C-(propyl)-N-(2,6-dinonadecyl-phenyl)]amidinato}di-{methyl}neodymium; {[N-(2,6-dichloro-phenyl)-C-(perfluorophenyl)-N-(2,6-dichloro-phenyl)]amidinato}di-{methylethylamino}neodymium; {[N-(2,6-ditrimethylsilylethyl-phenyl)-C-(butyl)-P-(2,6-ditrimethylsilylethyl-phenyl)]phosphoamidinato}di-{methylethylamino}yttrium; {[N-(2,6-diheptadecyl-phenyl)-C-(methyl)-N-(2,6-diheptadecyl-phenyl)]amidinato}di-{ethyl}cerium; {[N-(2,6-dihexyl-phenyl)-C-(methyl)-N-(2,6-dihexyl-phenyl)]amidinato}di-{triethylsilylmethyl}samarium; {[N-(2,6-dihexadecyl-phenyl)-C-(methyl)-N-(2,6-dihexadecyl-phenyl)]amidinato}di-{dimethylamino}neodymium; {[P-(2,6-diphenyl-phenyl)-C-(propyl)-P-(2,6-diphenyl-phenyl)]phosphoamidinato}di-{ethyl}cerium; {[N-(2,6-didecyl-4-propyl-phenyl)-C-(tetradecyl)-N-(2,6-didecyl-4-propyl-phenyl]amidinato}di-{methyl}europium; {[N-(2,6-diundecyl-phenyl)-C-(ethyl)-N-(2,6-diundecyl-phenyl)]amidinato}di-{ethyl}yttrium; {[P-(2,6-dioctyl-4-hexadecyl-phenyl)-C-(propyl)-P-(2,6-dioctyl-4-hexadecyl-phenyl]phosphoamidinato}di-{methyl}neodymium; {[N-(2,6-ditriethylsilylmethyl-phenyl)-C-(ethyl)-P-(2,6-ditriethylsilylmethyl-phenyl)]phosphoamidinato}di-{triethylsilylmethyl}neodymium; {[N-(2,6-dichloro-phenyl)-C-(methyl)-N-(2,6-dichloro-phenyl)]amidinato}di-{methyl}yttrium; {[N-(2,6-bis(dibutylamino)-phenyl)-C-(propyl)-N-(2,6-bis(dibutylamino)-phenyl)]amidinato}di-{ethyl}yttrium; {[N-(2,6-ditridecyl-4-butyl-phenyl)-C-(propyl)-N-(2,6-ditridecyl-4-butyl-phenyl]amidinato}di-{methyl}samarium; {[N-(2,6-diiodo-phenyl)-C-(ethyl)-N-(2,6-diiodo-phenyl)]amidinato}di-{methyl}yttrium; {[N-(2,6-dibutyl-phenyl)-C-(butyl)-N-(2,6-dibutyl-phenyl)]amidinato}di-{butyl}yttrium; {[N-(2,6-didecyl-4-ethyl-phenyl)-C-(phenyl)-N-(2,6-didecyl-4-ethyl-phenyl]amidinato}di-{butyl}europium; {[N-(2,6-ditetradecyl-phenyl)-C-(ethyl)-N-(2,6-ditetradecyl-phenyl)]amidinato}di-{methyl}europium; {[N-(2,6-dibutylamino-phenyl)-C-(perfluorophenyl)-N-(2,6-dibutylamino-phenyl)]amidinato}di-{tridecyl}neodymium; {[N-(2,6-bis(diethylamino)-phenyl)-C-(dimethylamino)-N-(2,6-bis(diethylamino)-phenyl)]amidinato}di-{methyl}yttrium; {[N-(2,6-dipropyl-phenyl)-C-(propyl)-N-(2,6-dipropyl-phenyl)]amidinato}di-{propyl}yttrium; {[N-(2,6-di4-methylphenoxy-phenyl)-C-(butyl)-N-(2,6-di4-methylphenoxy-phenyl)]amidinato}di-{butyl}neodymium; {[N-(2,6-dinonadecyl-phenyl)-C-(pentyl)-N-(2,6-dinonadecyl-phenyl)]amidinato}di-{methyl}praseodymium; {[N-(2,6-dinonadecyl-phenyl)-C-(propyl)-N-(2,6-dinonadecyl-phenyl)]amidinato}di-{methyl}yttrium; {[N-(2,6-dihexyl-phenyl)-C-(methyl)-N-(2,6-dihexyl-phenyl)]amidinato}di-{ethyl}cerium; {[N-(2,6-ditridecyl-phenyl)-C-(iodo)-N-(2,6-ditridecyl-phenyl)]amidinato}di-{ethyl}praseodymium; {[N-(2,6-dioctyl-phenyl)-C-(butyl)-N-(2,6-dioctyl-phenyl)]amidinato}di-{hydrido}europium; {[N-(2,6-diheptadecyl-phenyl)-C-(benzyl)-N-(2,6-diheptadecyl-phenyl)]amidinato}di-{benzyl}neodymium; {[N-(2,6-dibromo-phenyl)-C-(butyl)-N-(2,6-dibromo-phenyl)]amidinato}di-{perfluorophenyl}yttrium; {[N-(2,6-di4-methylphenoxy-3-butyl-phenyl)-C-(methyl)-N-(2,6-di4-methylphenoxy-3-butyl-phenyl]amidinato}di-{butyl}samarium; {[N-(2,6-dibutylamino-phenyl)-C-(methyl)-N-(2,6-dibutylamino-phenyl)]amidinato}di-{dimethylamino}yttrium; {[N-(2,6-diiodo-phenyl)-C-(tetradecyl)-N-(2,6-diiodo-phenyl)]amidinato}di-{propyl}yttrium; {[N-(2,6-dibenzyl-phenyl)-C-(methyl)-N-(2,6-dibenzyl-phenyl)]amidinato}di-{ethyl}yttrium; {[N-(2,6-bis(diethylamino)-phenyl)-C-(heptyl)-N-(2,6-bis(diethylamino)-phenyl)]amidinato}di-{propyl}yttrium; {[N-(2,6-bis(dibutylamino)-phenyl)-C-(iodo)-N-(2,6-bis(dibutylamino)-phenyl)]amidinato}di-{butyl}neodymium; {[N-(2,6-dipentadecyl-phenyl)-C-(bromo)-N-(2,6-dipentadecyl-phenyl)]amidinato}di-{butyl}yttrium; {[N-(2,6-diiodo-phenyl)-C-(triethylsilylmethyl)-N-(2,6-diiodo-phenyl)]amidinato}di-{propyl}neodymium; {[N-(2,6-bis(dimethylamino)-phenyl)-C-(propyl)-N-(2,6-bis(dimethylamino)-phenyl)]amidinato}di-{propyl}neodymium; {[N-(2,6-dipentadecyl-phenyl)-C-(butyl)-N-(2,6-dipentadecyl-phenyl)]amidinato}di-{propyl}praseodymium; {[N-(2,6-dinonadecyl-phenyl)-C-(methyl)-P-(2,6-dinonadecyl-phenyl)]phosphoamidinato}di-{propyl}neodymium; {[N-(2,6-didodecyl-phenyl)-C-(propyl)-N-(2,6-didodecyl-phenyl)]amidinato}di-{ethyl}neodymium; {[N-(2,6-dipentadecyl-phenyl)-C-(iodo)-N-(2,6-dipentadecyl-phenyl)]amidinato}di-{ethyl}yttrium; {[N-(2,6-dichloro-phenyl)-C-(hexyl)-N-(2,6-dichloro-phenyl)]amidinato}di-{butyl}yttrium; {[N-(2,6-dibutylamino-4-methyl-phenyl)-C-(methyl)-N-(2,6-dibutylamino-4-methyl-phenyl]

amidinato}di-{ethyl}neodymium; {[N-(2,6-didecyl-phenyl)-C-(propyl)-N-(2,6-didecyl-phenyl)]amidinato}di-{butyl}yttrium; {[N-(2,6-bis(dimethylamino)-3-octyl-phenyl)-C-(butyl)-N-(2,6-bis(dimethylamino)-3-octyl-phenyl)]amidinato}di-{heptyl}yttrium; {[N-(2,6-dioctadecyl-phenyl)-C-(ethyl)-P-(2,6-dioctadecyl-phenyl)]phosphoamidinato}di-{methyl}neodymium; {[N-(2,6-dibutyl-3-methyl-phenyl)-C-(methyl)-N-(2,6-dibutyl-3-methyl-phenyl]amidinato}di-{methyl}neodymium; {[N-(2,6-dipentyl-phenyl)-C-(ethyl)-N-(2,6-dipentyl-phenyl)]amidinato}di-{propyl}cerium; {[N-(2,6-bis(diphenylphosphino)-phenyl)-C-(propyl)-N-(2,6-bis(diphenylphosphino)-phenyl)]amidinato}di-{butyl}neodymium; {[P-(2,6-dinonyl-phenyl)-C-(propyl)-P-(2,6-dinonyl-phenyl)]phosphoamidinato}di-{methyl}neodymium; {[N-(2,6-diphenyl-phenyl)-C-(ethyl)-N-(2,6-diphenyl-phenyl)]amidinato}di-{propyl}europium; {[N-(2,6-ditriethylsilylmethyl-phenyl)-C-(butyl)-N-(2,6-ditriethylsilylmethyl-phenyl)]amidinato}di-{butyl}europium; {[N-(2,6-dimethylethylamino-phenyl)-C-(diphenylphosphino)-N-(2,6-dimethylethylamino-phenyl)]amidinato}di-{benzyl}yttrium; {[N-(2,6-didecyl-phenyl)-C-(dibutylamino)-N-(2,6-didecyl-phenyl)]amidinato}di-{propyl}yttrium; {[N-(2,6-ditriethylsilylmethyl-4-benzyl-phenyl)-C-(ethyl)-N-(2,6-ditriethylsilylmethyl-4-benzyl-phenyl]amidinato}di-{octadecyl}yttrium; {[P-(2,6-dinonadecyl-phenyl)-C-(propyl)-P-(2,6-dinonadecyl-phenyl)]phosphoamidinato}di-{tetradecyl}neodymium; {[N-(2,6-ditridecyl-phenyl)-C-(methyl)-N-(2,6-ditridecyl-phenyl)]amidinato}di-{ethyl}cerium; {[N-(2,6-dioctyl-phenyl)-C-(diphenylphosphino)-N-(2,6-dioctyl-phenyl)]amidinato}di-{propyl}yttrium; {[N-(2,6-bis(dibutylamino)-4-ethyl-phenyl)-C-(hydrido)-N-(2,6-bis(dibutylamino)-4-ethyl-phenyl]amidinato}di-{butyl}samarium; {[N-(2,6-diphenyl-phenyl)-C-(tetradecyl)-N-(2,6-diphenyl-phenyl)]amidinato}di-{propyl}praseodymium; {[N-(2,6-bis(dibutylamino)-phenyl)-C-(propyl)-N-(2,6-bis(dibutylamino)-phenyl)]amidinato}di-{phenyl}cerium; {[N-(2,6-ditetradecyl-phenyl)-C-(diethylamino)-N-(2,6-ditetradecyl-phenyl)]amidinato}di-{butyl}cerium; {[N-(2,6-dinonadecyl-phenyl)-C-(propyl)-N-(2,6-dinonadecyl-phenyl)]amidinato}di-{ethyl}neodymium; {[N-(2,6-didodecyl-phenyl)-C-(propyl)-N-(2,6-didodecyl-phenyl)]amidinato}di-{methyl}yttrium; {[N-(2,6-dioctadecyl-phenyl)-C-(hydrido)-N-(2,6-dioctadecyl-phenyl)]amidinato}di-{methyl}yttrium; {[N-(2,6-dimethylethylamino-phenyl)-C-(methyl)-N-(2,6-dimethylethylamino-phenyl)]amidinato}di-{methyl}neodymium; {[N-(2,6-diiodo-phenyl)-C-(propyl)-N-(2,6-diiodo-phenyl)]amidinato}di-{heptadecyl}neodymium; {[N-(2,6-dihexyl-phenyl)-C-(ethyl)-N-(2,6-dihexyl-phenyl)]amidinato}di-{diethylamino}praseodymium; {[N-(2,6-bis(dimethylamino)-phenyl)-C-(butyl)-N-(2,6-bis(dimethylamino)-phenyl)]amidinato}di-{butyl}cerium; {[N-(2,6-diheptadecyl-phenyl)-C-(butyl)-N-(2,6-diheptadecyl-phenyl)]amidinato}di-{diethylamino}yttrium; {[N-(2,6-dibenzyl-phenyl)-C-(methyl)-N-(2,6-dibenzyl-phenyl)]amidinato}di-{butyl}neodymium; {[N-(2,6-bis(dibutylamino)-phenyl)-C-(ethyl)-N-(2,6-bis(dibutylamino)-phenyl)]amidinato}di-{ethyl}gadolinium; {[N-(2,6-bis(diethylamino)-phenyl)-C-(butyl)-N-(2,6-bis(diethylamino)-phenyl)]amidinato}di-{propyl}cerium; {[N-(2,6-ditriethylsilylmethyl-phenyl)-C-(propyl)-N-(2,6-ditriethylsilylmethyl-phenyl)]amidinato}di-{butyl}neodymium; {[N-(2,6-ditrimethylsilylethyl-phenyl)-C-(dibutylamino)-N-(2,6-ditrimethylsilylethyl-phenyl)]amidinato}di-{ethyl}yttrium; {[N-(2,6-ditetradecyl-4-methyl-phenyl)-C-(diphenylphosphino)-N-(2,6-ditetradecyl-4-methyl-phenyl]amidinato}di-{4-methylphenoxy}yttrium; {[N-(2,6-dinonyl-phenyl)-C-(ethyl)-N-(2,6-dinonyl-phenyl)]amidinato}di-{propyl}cerium; {[N-(2,6-dibutylamino-phenyl)-C-(butyl)-N-(2,6-dibutylamino-phenyl)]amidinato}di-{iodo}praseodymium; {[N-(2,6-dinonadecyl-phenyl)-C-(ethyl)-N-(2,6-dinonadecyl-phenyl)]amidinato}di-{propyl}neodymium; {[N-(2,6-bis(diethylamino)-phenyl)-C-(methyl)-N-(2,6-bis(diethylamino)-phenyl)]amidinato}di-{propyl}neodymium; {[N-(2,6-diheptyl-phenyl)-C-(methylethylamino)-N-(2,6-diheptyl-phenyl)]amidinato}di-{pentadecyl}cerium; {[P-(2,6-dihexyl-phenyl)-C-(ethyl)-P-(2,6-dihexyl-phenyl)]phosphoamidinato}di-{butyl}cerium; {[N-(2,6-bis(dimethylamino)-phenyl)-C-(butyl)-N-(2,6-bis(dimethylamino)-phenyl)]amidinato}di-{methyl}yttrium; {[N-(2,6-dibutylamino-phenyl)-C-(methyl)-N-(2,6-dibutylamino-phenyl)]amidinato}di-{methyl}yttrium; {[N-(2,6-ditriethylsilylmethyl-phenyl)-C-(butyl)-N-(2,6-ditriethylsilylmethyl-phenyl)]amidinato}di-{hydrido}neodymium; {[N-(2,6-dichloro-phenyl)-C-(methyl)-N-(2,6-dichloro-phenyl)]amidinato}di-{methyl}samarium; {[N-(2,6-diheptadecyl-phenyl)-C-(ethyl)-N-(2,6-diheptadecyl-phenyl)]amidinato}di-{hydrido}praseodymium; {[N-(2,6-ditrimethylsilylethyl-phenyl)-C-(hydrido)-N-(2,6-ditrimethylsilylethyl-phenyl)]amidinato}di-{bromo}yttrium; {[N-(2,6-ditetradecyl-phenyl)-C-(ethyl)-N-(2,6-ditetradecyl-phenyl)]amidinato}di-{methyl}samarium; {[N-(2,6-ditriethylsilylmethyl-phenyl)-C-(butyl)-N-(2,6-ditriethylsilylmethyl-phenyl)]amidinato}di-{propyl}samarium; {[N-(2,6-diundecyl-phenyl)-C-(propyl)-N-(2,6-diundecyl-phenyl)]amidinato}di-{propyl}yttrium; {[N-(2,6-dibutyl-phenyl)-C-(hydrido)-N-(2,6-dibutyl-phenyl)]amidinato}di-{methyl}praseodymium; {[N-(2,6-diheptyl-4-methyl-phenyl)-C-(benzyl)-N-(2,6-diheptyl-4-methyl-phenyl]amidinato}di-{methyl}gadolinium; {[N-(2,6-ditriethylsilylmethyl-phenyl)-C-(ethyl)-N-(2,6-ditriethylsilylmethyl-phenyl)]amidinato}di-{butyl}neodymium; {[N-(2,6-diphenyl-phenyl)-C-(hydrido)-N-(2,6-diphenyl-phenyl)]amidinato}di-{methyl}yttrium; {[N-(2,6-dichloro-phenyl)-C-(diethylamino)-N-(2,6-dichloro-phenyl)]amidinato}di-{dibutylamino}yttrium; {[N-(2,6-ditetradecyl-phenyl)-C-(iodo)-N-(2,6-ditetradecyl-phenyl)]amidinato}di-{propyl}samarium; {[N-(2,6-dibenzyl-phenyl)-C-(butyl)-N-(2,6-dibenzyl-phenyl)]amidinato}di-{perfluorophenyl}praseodymium; {[N-(2,6-ditetradecyl-phenyl)-C-(ethyl)-N-(2,6-ditetradecyl-phenyl)]amidinato}di-{propyl}neodymium; {[N-(2,6-ditetradecyl-phenyl)-C-(ethyl)-N-(2,6-ditetradecyl-phenyl)]amidinato}di-{methyl}cerium; {[N-(2,6-bis(diethylamino)-phenyl)-C-(heptadecyl)-N-(2,6-bis(diethylamino)-phenyl)]amidinato}di-{ethyl}yttrium; {[N-(2,6-dinonyl-phenyl)-C-(methyl)-N-(2,6-dinonyl-phenyl)]amidinato}di-{butyl}neodymium; {[N-(2,6-ditrimethylsilylethyl-phenyl)-C-(hydrido)-N-(2,6-ditrimethylsilylethyl-phenyl)]amidinato}di-{propyl}yttrium; {[N-(2,6-di-4-methylphenoxy-phenyl)-C-(butyl)-N-(2,6-di-4-methylphenoxy-phenyl)]amidinato}di-{perfluorophenyl}neodymium; {[N-(2,6-ditrimethylsilylethyl-4-ethyl-phenyl)-C-(hydrido)-N-(2,6-ditrimethylsilylethyl-4-ethyl-phenyl]amidinato}di-{butyl}neodymium; {[N-(2,6-dibutylamino-phenyl)-C-(hydrido)-N-(2,6-dibutylaminophenyl)]amidinato}di-{butyl}yttrium; {[N-(2,6-diheptyl-phenyl)-C-(pentadecyl)-N-(2,6-diheptyl-phenyl)]amidinato}di-{diphenylphosphino}neodymium; {[N-(2,6-dihexadecyl-phenyl)-C-(butyl)-N-(2,6-dihexadecyl-phenyl)]amidinato}di-{tridecyl}neodymium; {[N-(2,6-dinonyl-phenyl)-C-(ethyl)-N-(2,6-dinonyl-phenyl)]amidinato}di-{hydrido}neodymium; {[N-(2,6-di-4-methylphenoxy-phenyl)-C-(hydrido)-N-(2,6-di-4-methylphenoxy-phenyl)]amidinato}di-{hydrido}yttrium; {[N-(2,6-di4-methylphenoxy-phenyl)-C-(heptyl)-N-(2,6-di4-methylphenoxy-phenyl)]amidinato}di-{methyl}yttrium; {[N-(2,6-dioctyl-phenyl)-C-(methyl)-N-(2,6-dioctyl-phenyl)]amidinato}di-{ethyl}samarium; {[P-(2,6-dihexadecyl-phenyl)-C-(butyl)-P-(2,6-dihexadecyl-phenyl)]phosphoamidinato}di-{propyl}yttrium; {[P-(2,6-diheptadecyl-phenyl)-C-(iodo)-P-(2,6-diheptadecyl-phenyl)]phosphoamidinato}di-{hexyl}europium; {[N-(2,6-ditetradecyl-4-triethylsilylmethyl-phenyl)-C-(perfluorophenyl)-N-(2,6-ditetradecyl-4-triethylsilylmethyl-phenyl]amidinato}di-{ethyl}cerium; {[N-(2,6-dimethylethylamino-4-propyl-phenyl)-C-(iodo)-N-(2,6-dimethylethylamino-4-propyl-phenyl]amidinato}di-{butyl}yttrium; {[N-(2,6-bis(dibutylamino)-phenyl)-C-(chloro)-N-(2,6-bis(dibutylamino)-phenyl)]amidinato}di-{hydrido}neodymium; {[N-(2,6-diundecyl-phenyl)-C-(octadecyl)-N-(2,6-diundecyl-phenyl)]amidinato}di-{phenyl}neodymium; {[N-(2,6-diheptyl-phenyl)-C-(methyl)-N-(2,6-diheptyl-phenyl)]amidinato}di-{butyl}yttrium; {[N-(2,6-dibenzyl-phenyl)-C-(methyl)-N-(2,6-dibenzyl-phenyl)]amidinato}di-{methyl}neodymium; {[N-(2,6-didodecyl-3-ethyl-phenyl)-C-(hydrido)-N-(2,6-didodecyl-3-ethyl-phenyl]amidinato}di-{butyl}yttrium; {[N-(2,6-diphenyl-phenyl)-C-(diphenylphosphino)-N-(2,6-diphenyl-phenyl)]amidinato}di-{butyl}neodymium; {[N-(2,6-bis(diphenylphosphino)-phenyl)-C-(methyl)-N-(2,6-bis(diphenylphosphino)-phenyl)]amidinato}di-{ethyl}yttrium; {[N-(2,6-dibromo-phenyl)-C-(propyl)-N-(2,6-dibromo-phenyl)]amidinato}di-{methyl}yttrium; {[N-(2,6-diheptadecyl-phenyl)-C-(butyl)-N-(2,6-diheptadecyl-phenyl)]amidinato}di-{propyl}yttrium; {[N-(2,6-dichloro-phenyl)-C-(phenyl)-P-(2,6-dichloro-phenyl)]phosphoamidinato}di-{triethylsilylmethyl}yttrium; {[N-(2,6-dioctyl-phenyl)-C-(diethylamino)-N-(2,6-dioctyl-phenyl)]amidinato}di-{propyl}samarium; {[P-(2,6-dioctadecyl-phenyl)-C-(propyl)-P-(2,6-dioctadecyl-phenyl)]phosphoamidinato}di-{chloro}yttrium; {[N-(2,6-diiodo-phenyl)-C-(octyl)-P-(2,6-diiodo-phenyl)]phosphoamidinato}di-{butyl}samarium; {[N-(2,6-dimethylethylamino-phenyl)-C-(propyl)-N-(2,6-dimethylethylamino-phenyl)]amidinato}di-{tridecyl}yttrium; {[N-(2,6-dihexyl-phenyl)-C-(hydrido)-N-(2,6-dihexyl-phenyl)]amidinato}di-{ethyl}yttrium; {[N-(2,6-bis(dimethylamino)-phenyl)-C-(butyl)-N-(2,6-bis(dimethylamino)-phenyl)]amidinato}di-{propyl}yttrium; {[N-(2,6-di4-methylphenoxy-phenyl)-C-(butyl)-N-(2,6-di4-methylphenoxy-phenyl)]amidinato}di-{hydrido}neodymium; {[N-(2,6-bis(dibutylamino)-phenyl)-C-(butyl)-N-(2,6-bis(dibutylamino)-phenyl)]amidinato}di-{butyl}cerium; {[N-(2,6-diiodo-phenyl)-C-(nonyl)-N-(2,6-diiodo-phenyl)]amidinato}di-{tetradecyl}samarium; {[N-(2,6-dioctadecyl-3-hexyl-phenyl)-C-(hexyl)-N-(2,6-dioctadecyl-3-hexyl-phenyl]amidinato}di-{hydrido}neodymium; {[N-(2,6-dibutyl-phenyl)-C-(butyl)-N-(2,6-dibutyl-phenyl)]amidinato}di-{hydrido}neodymium; {[N-(2,6-diundecyl-phenyl)-C-(tetradecyl)-N-(2,6-diundecyl-phenyl)]amidinato}di-{propyl}neodymium; {[P-(2,6-didodecyl-phenyl)-C-(butyl)-P-(2,6-didodecyl-phenyl)]phosphoamidinato}di-{propyl}praseodymium; {[P-(2,6-bis(diethylamino)-4-hexadecyl-phenyl)-C-(methyl)-P-(2,6-bis(diethylamino)-4-hexadecyl-phenyl)]phosphoamidinato}di-{hydrido}yttrium; {[N-(2,6-bis(dimethylamino)-phenyl)-C-(tridecyl)-N-(2,6-bis(dimethylamino)-phenyl)]amidinato}di-{ethyl}samarium; {[N-(2,6-dibenzyl-phenyl)-C-(propyl)-N-(2,6-dibenzyl-phenyl)]amidinato}di-{butyl}cerium; {[N-(2,6-diiodo-phenyl)-C-(propyl)-N-(2,6-diiodo-phenyl)]amidinato}di-{propyl}yttrium; {[N-(2,6-dichloro-phenyl)-C-(butyl)-N-(2,6-dichloro-phenyl)]amidinato}di-{methyl}cerium; {[N-(2,6-diheptyl-phenyl)-C-(tridecyl)-P-(2,6-diheptyl-phenyl)]phosphoamidinato}di-{methyl}samarium; {[N-(2,6-ditriethylsilylmethyl-3-butyl-phenyl)-C-(hydrido)-N-(2,6-ditriethylsilylmethyl-3-butyl-phenyl]amidinato}di-{propyl}cerium; {[N-(2,6-bis(dibutylamino)-phenyl)-C-(butylamino)-N-(2,6-bis(dibutylamino)-phenyl)]amidinato}di-{methyl}yttrium; {[N-(2,6-didodecyl-phenyl)-C-(ethyl)-P-(2,6-didodecyl-phenyl)]phosphoamidinato}di-{tridecyl}praseodymium; {[N-(2,6-ditridecyl-phenyl)-C-(methyl)-N-(2,6-ditridecyl-phenyl)]amidinato}di-{hydrido}yttrium; {[N-(2,6-dipentyl-phenyl)-C-(heptyl)-P-(2,6-dipentyl-phenyl)]phosphoamidinato}di-{hydrido}neodymium; {[N-(2,6-didodecyl-phenyl)-C-(propyl)-N-(2,6-didodecyl-phenyl)]amidinato}di-{methyl}neodymium; {[N-(2,6-ditriethylsilylmethyl-phenyl)-C-(propyl)-N-(2,6-ditriethylsilylmethyl-phenyl)]amidinato}di-{propyl}praseodymium; {[N-(2,6-dibenzyl-phenyl)-C-(hydrido)-N-(2,6-dibenzyl-phenyl)]amidinato}di-{perfluorophenyl}samarium; {[N-(2,6-dinonyl-phenyl)-C-(hexyl)-N-(2,6-dinonyl-phenyl)]amidinato}di-{ethyl}yttrium; {[N-(2,6-ditrimethylsilylethyl-phenyl)-C-(diphenylphosphino)-N-(2,6-ditrimethylsilylethyl-phenyl)]amidinato}di-{propyl}gadolinium; {[P-(2,6-ditridecyl-phenyl)-C-(hydrido)-P-(2,6-ditridecyl-phenyl)]phosphoamidinato}di-{ethyl}samarium; {[N-(2,6-diheptyl-phenyl)-C-(propyl)-N-(2,6-diheptyl-phenyl)]amidinato}di-{4-methylphenoxy}yttrium; {[N-(2,6-diphenyl-phenyl)-C-(ethyl)-N-(2,6-diphenyl-phenyl)]amidinato}di-{heptyl}neodymium; {[N-(2,6-dioctyl-phenyl)-C-(ethyl)-N-(2,6-dioctyl-phenyl)]amidinato}di-{propyl}cerium; {[N-(2,6-didecyl-4-propyl-phenyl)-C-(methyl)-N-(2,6-didecyl-4-propyl-phenyl]amidinato}di-{propyl}europium; {[N-(2,6-di-4-methylphenoxy-phenyl)-C-(butyl)-N-(2,6-di4-methylphenoxy-phenyl)]amidinato}di-{iodo}yttrium; {[N-(2,6-di4-methylphenoxy-phenyl)-C-(triethylsilylmethyl)-P-(2,6-di4-methylphenoxy-phenyl)]phosphoamidinato}di-{methyl}yttrium; {[N-(2,6-bis(dimethylamino)-phenyl)-C-(butyl)-N-(2,6-bis(dimethylamino)-phenyl)]amidinato}di-{butylamino}praseodymium; {[N-(2,6-diheptadecyl-phenyl)-C-(propyl)-N-(2,6-diheptadecyl-phenyl)]amidinato}di-{propyl}cerium; {[N-(2,6-bis(diphenylphosphino)-phenyl)-C-(nonyl)-N-(2,6-bis(diphenylphosphino)-phenyl)]amidinato}di-{diethylamino}cerium; {[N-(2,6-bis(dimethylamino)-phenyl)-C-(methyl)-P-(2,6-bis(dimethylamino)-phenyl)]phosphoamidinato}di-{propyl}yttrium; {[N-(2,6-dibutyl-phenyl)-C-(propyl)-N-(2,6-dibutyl-phenyl)]amidinato}di-{diethylphosphino}cerium; {[N-(2,6-bis(dimethylamino)-4-butyl-phenyl)-C-(butyl)-N-(2,6-bis(dimethylamino)-4-butyl-phenyl]amidinato}di-{octadecyl}yttrium; {[N-(2,6-dihexadecyl-phenyl)-C-(ethyl)-N-(2,6-dihexadecyl-phenyl)]amidinato}di-{propyl}yttrium; {[N-(2,6-diphenyl-4-propyl-phenyl)-C-(ethyl)-N-(2,6-diphenyl-4-propyl-phenyl]amidinato}di-{butyl}neodymium; {[N-(2,6-dinonyl-phenyl)-C-(butyl)-N-(2,6-dinonyl-phenyl)]

amidinato}di-{butyl}yttrium; {[N-(2,6-didecyl-phenyl)-C-(propyl)-N-(2,6-didecyl-phenyl)]amidinato}di-{butyl}neodymium; {[N-(2,6-diphenyl-phenyl)-C-(hydrido)-N-(2,6-diphenyl-phenyl)]amidinato}di-{propyl}yttrium; {[N-(2,6-dinonadecyl-phenyl)-C-(ethyl)-N-(2,6-dinonadecyl-phenyl)]amidinato}di-{butyl}cerium; {[N-(2,6-dibenzyl-phenyl)-C-(hydrido)-N-(2,6-dibenzyl-phenyl)]amidinato}di-{hexyl}europium; {[P-(2,6-diphenyl-phenyl)-C-(propyl)-P-(2,6-diphenyl-phenyl)]phosphoamidinato}di-{perfluorophenyl}praseodymium; {[N-(2,6-dichloro-phenyl)-C-(methyl)-N-(2,6-dichloro-phenyl)]amidinato}di-{methyl}samarium; {[N-(2,6-dihexyl-phenyl)-C-(methyl)-N-(2,6-dihexyl-phenyl)]amidinato}di-{heptyl}neodymium; {[N-(2,6-dihexyl-phenyl)-C-(propyl)-N-(2,6-dihexyl-phenyl)]amidinato}di-{propyl}neodymium; {[N-(2,6-diiodo-phenyl)-C-(butyl)-N-(2,6-diiodo-phenyl)]amidinato}di-{hydrido}yttrium; {[N-(2,6-dichloro-phenyl)-C-(phenyl)-N-(2,6-dichloro-phenyl)]amidinato}di-{methyl}neodymium; {[N-(2,6-dibutyl-phenyl)-C-(butylamino)-N-(2,6-dibutyl-phenyl)]amidinato}di-{butyl}yttrium; {[N-(2,6-bis(diphenylphosphino)-phenyl)-C-(ethyl)-N-(2,6-bis(diphenylphosphino)-phenyl)]amidinato}di-{dimethylamino}yttrium; {[N-(2,6-dipentyl-phenyl)-C-(propyl)-N-(2,6-dipentyl-phenyl)]amidinato}di-{butyl}yttrium; {[N-(2,6-diiodo-phenyl)-C-(propyl)-N-(2,6-diiodo-phenyl)]amidinato}di-{4-methylphenoxy}neodymium; {[N-(2,6-bis(diethylamino)-phenyl)-C-(diethylamino)-N-(2,6-bis(diethylamino)-phenyl)]amidinato}di-{propyl}neodymium; {[N-(2,6-dioctadecyl-phenyl)-C-(triethylsilylmethyl)-N-(2,6-dioctadecyl-phenyl)]amidinato}di-{hydrido}yttrium; {[N-(2,6-dioctadecyl-4-methyl-phenyl)-C-(propyl)-N-(2,6-dibutyl-4-methyl-phenyl]amidinato}di-{methyl}samarium; {[N-(2,6-bis(dimethylamino)-phenyl)-C-(methyl)-N-(2,6-dibenzyl-phenyl)]amidinato}di-{methyl}yttrium; {[N-(2,6-diundecyl-phenyl)-C-(nonyl)-N-(2,6-ditetradecyl-phenyl)]amidinato}di-{ethyl}yttrium; {[N-(2,6-dibenzyl-phenyl)-C-(propyl)-N-(2,6-bis(dibutylamino)-phenyl)]amidinato}di-{butyl}praseodymium; {[N-(2,6-ditriethylsilylmethyl-phenyl)-C-(butyl)-N-(2,6-ditridecyl-phenyl)]amidinato}di-{propyl}samarium; {[N-(2,6-dinonyl-phenyl)-C-(propyl)-N-(2,6-dinonadecyl-phenyl)]amidinato}di-{ethyl}yttrium; {[N-(2,6-dioctadecyl-phenyl)-C-(iodo)-N-(2,6-diheptyl-phenyl)]amidinato}di-{propyl}neodymium; {[N-(2,6-dibutylamino-4-propyl-phenyl)-C-(methyl)-N-(2,6-ditriethylsilylmethyl-4-propyl-phenyl]amidinato}di-{propyl}praseodymium; {[N-(2,6-diiodo-4-propyl-phenyl)-C-(methyl)-N-(2,6-dihexyl-4-propyl-phenyl]amidinato}di-{diphenylphosphino}neodymium; {[N-(2,6-ditridecyl-phenyl)-C-(chloro)-N-(2,6-bis(dibutylamino)-phenyl)]amidinato}di-{decyl}neodymium; {[N-(2,6-didodecyl-phenyl)-C-(propyl)-N-(2,6-diphenyl-phenyl)]amidinato}di-{diphenylphosphino}yttrium; {[N-(2,6-diundecyl-phenyl)-C-(ethyl)-N-(2,6-diundecyl-phenyl)]amidinato}di-{butyl}yttrium; {[P-(2,6-dioctadecyl-4-hydrido-phenyl)-C-(ethyl)-P-(2,6-dihexyl-4-hydrido-phenyl]phosphoamidinato}di-{butyl}samarium; {[N-(2,6-dioctadecyl-phenyl)-C-(propyl)-N-(2,6-diphenyl-phenyl)]amidinato}di-{dimethylamino}neodymium; {[N-(2,6-dinonadecyl-phenyl)-C-(propyl)-N-(2,6-ditriethylsilylmethyl-phenyl)]amidinato}di-{butyl}gadolinium; {[N-(2,6-didodecyl-4-propyl-phenyl)-C-(methyl)-N-(2,6-bis(diethylamino)-4-propyl-phenyl]amidinato}di-{methyl}yttrium; {[N-(2,6-dipropyl-phenyl)-C-(butylamino)-N-(2,6-dimethylethylamino-phenyl)]amidinato}di-{chloro}yttrium; {[N-(2,6-di4-methylphenoxy-phenyl)-C-(butyl)-N-(2,6-bis(diethylamino)-phenyl)]amidinato}di-{hydrido}yttrium; {[N-(2,6-dinonyl-phenyl)-C-(propyl)-N-(2,6-diheptyl-phenyl)]amidinato}di-{propyl}neodymium; {[N-(2,6-dichloro-3-chloro-phenyl)-C-(ethyl)-P-(2,6-dioctyl-3-chloro-phenyl]phosphoamidinato}di-{undecyl}yttrium; {[N-(2,6-dinonyl-phenyl)-C-(propyl)-N-(2,6-dichloro-phenyl)]amidinato}di-{butylamino}yttrium; {[N-(2,6-dihexadecyl-phenyl)-C-(chloro)-N-(2,6-dibenzyl-phenyl)]amidinato}di-{hydrido}yttrium; {[N-(2,6-dipentyl-phenyl)-C-(butylamino)-N-(2,6-ditrimethylsilylethyl-phenyl)]amidinato}di-{hydrido}praseodymium; {[N-(2,6-bis(dibutylamino)-phenyl)-C-(hydrido)-P-(2,6-dipentyl-phenyl)]phosphoamidinato}di-{methylethylamino}cerium; {[N-(2,6-di4-methylphenoxy-4-methyl-phenyl)-C-(undecyl)-N-(2,6-dihexadecyl-4-methyl-phenyl]amidinato}di-{ethyl}neodymium; {[N-(2,6-dipentadecyl-phenyl)-C-(phenyl)-N-(2,6-didecyl-phenyl)]amidinato}di-{methyl}yttrium; {[N-(2,6-diundecyl-phenyl)-C-(butyl)-N-(2,6-dinonyl-phenyl)]amidinato}di-{butyl}europium; {[N-(2,6-diiodo-phenyl)-C-(butyl)-N-(2,6-dihexadecyl-phenyl)]amidinato}di-{propyl}yttrium; {[N-(2,6-dibenzyl-phenyl)-C-(methyl)-N-(2,6-diheptadecyl-phenyl)]amidinato}di-{phenyl}gadolinium; {[N-(2,6-ditrimethylsilylethyl-phenyl)-C-(ethyl)-N-(2,6-bis(dimethylamino)-phenyl)]amidinato}di-{tridecyl}samarium; {[N-(2,6-dibutylamino-phenyl)-C-(propyl)-P-(2,6-ditridecyl-phenyl)]phosphoamidinato}di-{bromo}yttrium; {[N-(2,6-didecyl-phenyl)-C-(methyl)-N-(2,6-dipentyl-phenyl)]amidinato}di-{butyl}neodymium; {[N-(2,6-dibutyl-phenyl)-C-(butylamino)-P-(2,6-dioctadecyl-phenyl)]phosphoamidinato}di-{phenyl}neodymium; {[N-(2,6-dihexadecyl-phenyl)-C-(nonyl)-N-(2,6-dipropyl-phenyl)]amidinato}di-{hydrido}neodymium; {[N-(2,6-dipropyl-phenyl)-C-(propyl)-N-(2,6-dichloro-phenyl)]amidinato}di-{ethyl}yttrium; {[N-(2,6-ditriethylsilylmethyl-phenyl)-C-(propyl)-P-(2,6-dichloro-phenyl)]phosphoamidinato}di-{ethyl}samarium; {[N-(2,6-dipropyl-phenyl)-C-(ethyl)-N-(2,6-dipentyl-phenyl)]amidinato}di-{butyl}gadolinium; {[N-(2,6-didodecyl-phenyl)-C-(methyl)-N-(2,6-dichloro-phenyl)]amidinato}di-{propyl}neodymium; {[N-(2,6-dihexadecyl-4-iodo-phenyl)-C-(tetradecyl)-N-(2,6-didecyl-4-iodo-phenyl]amidinato}di-{heptadecyl}samarium; {[N-(2,6-dinonadecyl-phenyl)-C-(butyl)-N-(2,6-dibutyl-phenyl)]amidinato}di-{ethyl}yttrium; {[N-(2,6-dibromo-phenyl)-C-(propyl)-N-(2,6-diheptyl-phenyl)]amidinato}di-{methyl}yttrium; {[N-(2,6-dihexyl-4-ethyl-phenyl)-C-(chloro)-N-(2,6-bis(dibutylamino)-4-ethyl-phenyl]amidinato}di-{propyl}yttrium; {[N-(2,6-dihexyl-phenyl)-C-(methyl)-N-(2,6-dibromo-phenyl)]amidinato}di-{methyl}yttrium; {[N-(2,6-bis(dibutylamino)-phenyl)-C-(propyl)-N-(2,6-dinonyl-phenyl)]amidinato}di-{ethyl}yttrium; {[N-(2,6-di4-methylphenoxy-phenyl)-C-(butyl)-N-(2,6-bis(diphenylphosphino)-phenyl)]amidinato}di-{ethyl}neodymium; {[N-(2,6-diheptadecyl-phenyl)-C-(butyl)-N-(2,6-ditetradecyl-phenyl)]amidinato}di-{butyl}europium; {[N-(2,6-dibromo-phenyl)-C-(ethyl)-N-(2,6-diundecyl-phenyl)]amidinato}di-{chloro}yttrium; {[N-(2,6-dipentadecyl-4-methyl-phenyl)-C-(heptyl)-N-(2,6-dihexyl-4-methyl-phenyl]amidinato}di-{perfluorophenyl}yttrium; {[N-(2,6-dibutylamino-phenyl)-C-(ethyl)-N-(2,6-dibutyl-phenyl)]amidinato}di-{iodo}cerium; {[N-(2,6-diiodo-phenyl)-C-(propyl)-N-(2,6-ditetradecyl-phenyl)]amidinato}di-{methyl}yttrium; {[N-(2,6-bis(diphenylphosphino)-phenyl)-C-(propyl)-N-(2,6-ditrimethylsilylethyl-phenyl)]amidinato}di-{ethyl}neodymium; {[N-(2,6-dioctadecyl-phenyl)-C-

(ethyl)-N-(2,6-dinonyl-phenyl)]amidinato}di-{methyl}samarium; {[N-(2,6-dioctadecyl-4-propyl-phenyl)-C-(bromo)-N-(2,6-diphenyl-4-propyl-phenyl]amidinato}di-{ethyl}yttrium; {[N-(2,6-dimethylethylamino-phenyl)-C-(heptadecyl)-N-(2,6-dibromo-phenyl)]amidinato}di-{hydrido}cerium; {[N-(2,6-ditrimethylsilylethyl-phenyl)-C-(butyl)-N-(2,6-dibutyl-phenyl)]amidinato}di-{ethyl}yttrium; {[N-(2,6-dinonyl-phenyl)-C-(propyl)-N-(2,6-dichloro-phenyl)]amidinato}di-{butyl}neodymium; {[N-(2,6-dibenzyl-phenyl)-C-(methyl)-N-(2,6-ditrimethylsilylethyl-phenyl)]amidinato}di-{hydrido}neodymium; {[N-(2,6-bis(dimethylamino)-phenyl)-C-(butyl)-N-(2,6-dibromo-phenyl)]amidinato}di-{methyl}neodymium; {[N-(2,6-didecyl-4-hydrido-phenyl)-C-(ethyl)-N-(2,6-dipentadecyl-4-hydrido-phenyl]amidinato}di-{propyl}yttrium; {[N-(2,6-dibenzyl-phenyl)-C-(butyl)-N-(2,6-bis(diphenylphosphino)-phenyl)]amidinato}di-{methyl}neodymium; {[N-(2,6-diheptyl-phenyl)-C-(butyl)-N-(2,6-dinonadecyl-phenyl)]amidinato}di-{methyl}neodymium; {[N-(2,6-bis(diphenylphosphino)-3-methyl-phenyl)-C-(dibutylamino)-N-(2,6-bis(dimethylamino)-3-methyl-phenyl]amidinato}di-{hydrido}cerium; {[N-(2,6-diundecyl-phenyl)-C-(hydrido)-N-(2,6-di4-methylphenoxy-phenyl)]amidinato}di-{methyl}yttrium; {[N-(2,6-dinonadecyl-phenyl)-C-(methyl)-N-(2,6-ditrimethylsilylethyl-phenyl)]amidinato}di-{butyl}samarium; {[N-(2,6-diheptyl-4-dodecyl-phenyl)-C-(propyl)-N-(2,6-dinonadecyl-4-dodecyl-phenyl]amidinato}di-{dibutylamino}europium; {[N-(2,6-ditrimethylsilylethyl-phenyl)-C-(methyl)-N-(2,6-diheptyl-phenyl)]amidinato}di-{butyl}yttrium; {[N-(2,6-bis(diethylamino)-phenyl)-C-(pentadecyl)-N-(2,6-dibutyl-phenyl)]amidinato}di-{hydrido}yttrium; {[N-(2,6-ditridecyl-phenyl)-C-(butyl)-N-(2,6-diphenyl-phenyl)]amidinato}di-{propyl}yttrium; {[N-(2,6-dinonadecyl-phenyl)-C-(butyl)-N-(2,6-diphenyl-phenyl)]amidinato}di-{butyl}europium; {[P-(2,6-dinonadecyl-4-hydrido-phenyl)-C-(hydrido)-P-(2,6-di4-methylphenoxy-4-hydrido-phenyl]phosphoamidinato}di-{methyl}cerium; {[N-(2,6-di4-methylphenoxy-phenyl)-C-(dibutylamino)-N-(2,6-dioctyl-phenyl)]amidinato}di-{tetradecyl}neodymium; {[N-(2,6-dioctyl-phenyl)-C-(butyl)-N-(2,6-dipropyl-phenyl)]amidinato}di-{methyl}yttrium; {[P-(2,6-bis(dibutylamino)-phenyl)-C-(heptyl)-P-(2,6-bis(diethylamino)-phenyl)]phosphoamidinato}di-{butyl}neodymium; {[N-(2,6-dibutylamino-phenyl)-C-(butyl)-N-(2,6-dipropyl-phenyl)]amidinato}di-{hydrido}yttrium; {[N-(2,6-di4-methylphenoxy-phenyl)-C-(methyl)-N-(2,6-dioctadecyl-phenyl)]amidinato}di-{ethyl}samarium; {[N-(2,6-bis(dimethylamino)-phenyl)-C-(methyl)-N-(2,6-didodecyl-phenyl)]amidinato}di-{dimethylamino}neodymium; {[N-(2,6-dihexyl-phenyl)-C-(heptadecyl)-N-(2,6-dipentadecyl-phenyl)]amidinato}di-{propyl}cerium; {[N-(2,6-bis(dimethylamino)-3-nonyl-phenyl)-C-(propyl)-N-(2,6-di4-methylphenoxy-3-nonyl-phenyl]amidinato}di-{hydrido}yttrium; {[N-(2,6-dibenzyl-phenyl)-C-(propyl)-N-(2,6-ditriethylsilylmethyl-phenyl)]amidinato}di-{octyl}yttrium; {[N-(2,6-ditrimethylsilylethyl-phenyl)-C-(methyl)-N-(2,6-dihexyl-phenyl)]amidinato}di-{butylamino}yttrium; {[P-(2,6-ditriethylsilylmethyl-phenyl)-C-(hydrido)-P-(2,6-dihexyl-phenyl)]phosphoamidinato}di-{methylethylamino}yttrium; {[N-(2,6-dibromo-phenyl)-C-(propyl)-N-(2,6-dipentyl-phenyl)]amidinato}di-{butyl}yttrium; {[N-(2,6-dipentyl-phenyl)-C-(butyl)-N-(2,6-bis(diphenylphosphino)-phenyl)]amidinato}di-{ethyl}neodymium; {[N-(2,6-bis(dibutylamino)-phenyl)-C-(butyl)-N-(2,6-diiodo-phenyl)]amidinato}di-{butyl}yttrium; {[N-(2,6-dibenzyl-phenyl)-C-(methylethylamino)-N-(2,6-dibenzyl-phenyl)]amidinato}di-{ethyl}samarium; {[N-(2,6-diheptadecyl-phenyl)-C-(phenyl)-N-(2,6-dipentyl-phenyl)]amidinato}di-{dodecyl}neodymium; {[N-(2,6-dimethylethylamino-phenyl)-C-(ethyl)-N-(2,6-dichloro-phenyl)]amidinato}di-{ethyl}praseodymium; {[N-(2,6-dipentyl-phenyl)-C-(propyl)-N-(2,6-dipropyl-phenyl)]amidinato}di-{butyl}cerium; {[N-(2,6-diiodo-phenyl)-C-(butyl)-N-(2,6-diphenyl-phenyl)]amidinato}di-{propyl}cerium; {[N-(2,6-diiodo-phenyl)-C-(butyl)-N-(2,6-dipentyl-phenyl)]amidinato}di-{propyl}cerium; {[N-(2,6-dihexyl-3-propyl-phenyl)-C-(propyl)-N-(2,6-dihexadecyl-3-propyl-phenyl]amidinato}di-{methyl}neodymium; {[N-(2,6-dihexadecyl-phenyl)-C-(ethyl)-N-(2,6-dinonadecyl-phenyl)]amidinato}di-{methyl}praseodymium; {[N-(2,6-dibutyl-phenyl)-C-(pentyl)-N-(2,6-ditrimethylsilylethyl-phenyl)]amidinato}di-{ethyl}praseodymium; {[N-(2,6-diheptadecyl-phenyl)-C-(methylethylamino)-N-(2,6-di4-methylphenoxy-phenyl)]amidinato}di-{decyl}neodymium; {[N-(2,6-bis(dibutylamino)-phenyl)-C-(ethyl)-N-(2,6-dioctyl-phenyl)]amidinato}di-{butyl}cerium; {[N-(2,6-dipentyl-phenyl)-C-(methyl)-N-(2,6-bis(dibutylamino)-phenyl)]amidinato}di-{heptadecyl}neodymium; {[N-(2,6-dipentyl-phenyl)-C-(methyl)-N-(2,6-dinonyl-phenyl)]amidinato}di-{methyl}neodymium; {[N-(2,6-diheptadecyl-phenyl)-C-(ethyl)-N-(2,6-dichloro-phenyl)]amidinato}di-{propyl}europium; {[N-(2,6-didodecyl-phenyl)-C-(butyl)-N-(2,6-didodecyl-phenyl)]amidinato}di-{propyl}yttrium; {[N-(2,6-dioctadecyl-phenyl)-C-(methyl)-N-(2,6-dihexyl-phenyl)]amidinato}di-{methyl}yttrium; {[N-(2,6-dihexyl-phenyl)-C-(methyl)-P-(2,6-dipropyl-phenyl)]phosphoamidinato}di-{propyl}samarium; {[N-(2,6-diundecyl-4-pentadecyl-phenyl)-C-(propyl)-N-(2,6-diphenyl-4-pentadecyl-phenyl]amidinato}di-{butyl}neodymium; {[N-(2,6-didecyl-phenyl)-C-(propyl)-N-(2,6-diphenyl-phenyl)]amidinato}di-{hydrido}yttrium; {[N-(2,6-dinonadecyl-phenyl)-C-(pentadecyl)-N-(2,6-didecyl-phenyl)]amidinato}di-{dimethylamino}cerium; {[N-(2,6-dipentyl-phenyl)-C-(methyl)-N-(2,6-diheptadecyl-phenyl)]amidinato}di-{hydrido}neodymium; {[N-(2,6-diheptyl-phenyl)-C-(ethyl)-N-(2,6-bis(dibutylamino)-phenyl)]amidinato}{butyl}{iodo}cerium; {[N-(2,6-bis(diethylamino)-phenyl)-C-(butyl)-N-(2,6-dipropyl-phenyl)]amidinato}{ethyl}{chloro}gadolinium; {[N-(2,6-dihexadecyl-phenyl)-C-(methyl)-N-(2,6-dibutyl-phenyl)]amidinato}{heptyl}{propyl}praseodymium; {[P-(2,6-dinonadecyl-phenyl)-C-(propyl)-P-(2,6-dioctadecyl-phenyl)]phosphoamidinato}{butyl}{ethyl}yttrium; {[N-(2,6-dinonyl-phenyl)-C-(hexyl)-N-(2,6-dioctadecyl-phenyl)]amidinato}di-{propyl}gadolinium; {[N-(2,6-dibutyl-phenyl)-C-(methyl)-N-(2,6-bis(diphenylphosphino)-phenyl)]amidinato}{hydrido}{methyl}praseodymium; {[N-(2,6-di-4-methylphenoxy-phenyl)-C-(ethyl)-N-(2,6-diheptyl-phenyl)]amidinato}{butyl}{methyl}gadolinium; {[N-(2,6-bis(diethylamino)-phenyl)-C-(ethyl)-N-(2,6-dibromo-phenyl)]amidinato}{butyl}{pentadecyl}neodymium; {[N-(2,6-bis(diethylamino)-phenyl)-C-(hydrido)-N-(2,6-dinonyl-phenyl)]amidinato}{methyl}{hydrido}neodymium; {[N-(2,6-diphenyl-phenyl)-C-(dodecyl)-N-(2,6-dihexyl-phenyl)]amidinato}{undecyl}{methyl}neodymium; {[N-(2,6-ditriethylsilylmethyl-phenyl)-C-(propyl)-N-(2,6-ditriethylsilylmethyl-phenyl)]amidinato}{methyl}{butyl}cerium; {[N-(2,6-dipentyl-phenyl)-C-(diphenylphosphino)-N-(2,6-diundecyl-phenyl)]amidinato}{methyl}{pentyl}neodymium; {[N-(2,6-didecylphenyl)-C-(iodo)-N-(2,6-dibutylamino-phenyl)]amidinato}{octadecyl}{ethyl}neodymium; {[N-(2,6-dipentadecyl-3-butyl-phenyl)-C-(methyl)-N-(2,6-dibenzyl-3-butyl-phenyl]amidinato}di-{methyl}neodymium; {[N-(2,6-dinonadecyl-phenyl)-C-(ethyl)-N-(2,6-dihexadecyl-phenyl)]amidinato}{heptyl}{hydrido}samarium; {[N-(2,6-bis(dibutylamino)-phenyl)-C-(ethyl)-N-(2,6-diiodo-phenyl)]amidinato}di-{ethyl}neodymium; {[N-(2,6-dihexyl-3-ethyl-phenyl)-C-(propyl)-N-(2,6-di4-methylphenoxy-3-ethyl-phenyl]amidinato}{propyl}{butyl}yttrium; {[N-(2,6-dioctadecyl-4-propyl-phenyl)-C-(ethyl)-N-(2,6-diiodo-4-propyl-phenyl]amidinato}{methyl}{hydrido}yttrium; {[N-(2,6-diheptadecyl-phenyl)-C-(heptadecyl)-N-(2,6-ditridecyl-phenyl)]amidinato}{ethyl)}{methyl}gadolinium; {[N-(2,6-dibutylamino-phenyl)-C-(propyl)-P-(2,6-ditrimethylsilylethyl-phenyl)]phosphoamidinato}{butyl}{phenyl}gadolinium; {[N-(2,6-dinonyl-phenyl)-C-(butyl)-N-(2,6-dihexadecyl-phenyl)]amidinato}{chloro}{methyl}neodymium; {[N-(2,6-dihexyl-phenyl)-C-(butyl)-N-(2,6-di4-methylphenoxy-phenyl)]amidinato}{undecyl}{propyl}neodymium; {[N-(2,6-ditetradecyl-4-ethyl-phenyl)-C-(hexadecyl)-N-(2,6-dibutylamino-4-ethyl-phenyl]amidinato}{methyl}{octadecyl}neodymium; {[N-(2,6-dimethylethylamino-phenyl)-C-(butyl)-N-(2,6-dibutylamino-phenyl)]amidinato}di-{methyl}samarium; {[N-(2,6-didodecyl-3-butyl-phenyl)-C-(butyl)-N-(2,6-dibutylamino-3-butyl-phenyl]amidinato}{ethyl}{butyl}yttrium; {[N-(2,6-dihexyl-phenyl)-C-(butyl)-N-(2,6-dinonyl-phenyl)]amidinato}{octyl}{octadecyl}praseodymium; {[N-(2,6-dibenzyl-phenyl)-C-(ethyl)-N-(2,6-dichloro-phenyl)]amidinato}{hexyl}{ethyl}yttrium; {[N-(2,6-bis(dimethylamino)-phenyl)-C-(hydrido)-N-(2,6-dibromo-phenyl)]amidinato}{heptadecyl}{bromo}neodymium; {[N-(2,6-bis(diethylamino)-phenyl)-C-(propyl)-N-(2,6-bis(dimethylamino)-phenyl)]amidinato}{ethyl}{propyl}cerium; {[N-(2,6-dihexyl-phenyl)-C-(hexyl)-N-(2,6-bis(dibutylamino)-phenyl)]amidinato}{methyl}{propyl}yttrium; {[N-(2,6-diiodo-phenyl)-C-(propyl)-N-(2,6-bis(dimethylamino)-phenyl)]amidinato}{pentadecyl}{ethyl}samarium; {[N-(2,6-didodecyl-phenyl)-C-(hydrido)-P-(2,6-diundecyl-phenyl)]phosphoamidinato}{butyl}{ethyl}europium; {[N-(2,6-ditrimethylsilylethyl-phenyl)-C-(iodo)-N-(2,6-dibutyl-phenyl)]amidinato}{butyl}{propyl}yttrium; {[N-(2,6-bis(diethylamino)-phenyl)-C-(butyl)-N-(2,6-dinonyl-phenyl)]amidinato}{ethyl}{butyl}neodymium; {[N-(2,6-didecyl-4-methyl-phenyl)-C-(methyl)-N-(2,6-diheptyl-4-methyl-phenyl]amidinato}{diethylphosphino}{ethyl}yttrium; {[P-(2,6-dinonadecyl-phenyl)-C-(butyl)-P-(2,6-bis(diethylamino)-phenyl)]phosphoamidinato}{butyl}{methyl}yttrium; {[P-(2,6-ditrimethylsilylethyl-4-butyl-phenyl)-C-(iodo)-P-(2,6-didecyl-4-butyl-phenyl]phosphoamidinato}di-{butyl}yttrium; {[N-(2,6-dibenzyl-phenyl)-C-(butyl)-N-(2,6-diphenyl-phenyl)]amidinato}{triethylsilylmethyl}{propyl}cerium; {[N-(2,6-bis(dimethylamino)-phenyl)-C-(butyl)-N-(2,6-dibutylamino-phenyl)]amidinato}{pentadecyl}{hydrido}praseodymium; {[N-(2,6-ditridecyl-phenyl)-C-(butyl)-N-(2,6-diiodo-phenyl)]amidinato}{butyl}{methyl}samarium; {[N-(2,6-diphenyl-phenyl)-C-(hydrido)-N-(2,6-dimethylethylamino-phenyl)]amidinato}{ethyl}{triethylsilylmethyl}europium; {[N-(2,6-bis(diethylamino)-phenyl)-C-(butyl)-N-(2,6-ditridecyl-phenyl)]amidinato}{hydrido}{methyl}yttrium; {[N-(2,6-diphenyl-phenyl)-C-(methyl)-N-(2,6-dihexyl-phenyl)]amidinato}{propyl}{butyl}neodymium; {[N-(2,6-dioctadecyl-phenyl)-C-(hydrido)-N-(2,6-didecyl-phenyl)]amidinato}{propyl}{hydrido}neodymium; {[N-(2,6-dibenzyl-phenyl)-C-(triethylsilylmethyl)-N-(2,6-didodecyl-phenyl)]amidinato}{propyl}{butylamino}cerium; {[N-(2,6-bis(diphenylphosphino)-phenyl)-C-(hydrido)-N-(2,6-dipropyl-phenyl)]amidinato}{butyl}{propyl}neodymium; {[N-(2,6-ditrimethylsilylethyl-phenyl)-C-(hydrido)-P-(2,6-dimethylethylamino-phenyl)]phosphoamidinato}{4-methylphenoxy}{methyl}europium; {[N-(2,6-diiodo-phenyl)-C-(ethyl)-N-(2,6-dipropyl-phenyl)]amidinato}{propyl}{ethyl}gadolinium; {[N-(2,6-dibenzyl-4-dodecyl-phenyl)-C-(methyl)-N-(2,6-dichloro-4-dodecyl-phenyl]amidinato}{propyl}{butyl}yttrium; {[N-(2,6-dihexyl-phenyl)-C-(methyl)-N-(2,6-dibutylamino-phenyl)]amidinato}{hydrido}{propyl}samarium; {[N-(2,6-diphenyl-phenyl)-C-(methyl)-N-(2,6-dichloro-phenyl)]amidinato}{butylamino}{methylethylamino}neodymium; {[N-(2,6-diundecyl-phenyl)-C-(hydrido)-N-(2,6-dioctadecyl-phenyl)]amidinato}{diphenylphosphino}{nonyl}samarium; {[N-(2,6-dibenzyl-phenyl)-C-(methyl)-N-(2,6-dipentyl-phenyl)]amidinato}di-{ethyl}yttrium; {[N-(2,6-diphenyl-phenyl)-C-(ethyl)-N-(2,6-dichloro-phenyl)]amidinato}{propyl}{hydrido}yttrium; {[N-(2,6-ditrimethylsilylethyl-3-hydrido-phenyl)-C-(hydrido)-N-(2,6-ditriethylsilylmethyl-3-hydrido-phenyl]amidinato}{methyl}{hydrido}samarium; {[N-(2,6-dibromo-phenyl)-C-(methyl)-N-(2,6-diundecyl-phenyl)]amidinato}{ethyl}{diphenylphosphino}cerium; {[N-(2,6-dibutylamino-4-heptadecyl-phenyl)-C-(heptyl)-P-(2,6-diiodo-4-heptadecyl-phenyl]phosphoamidinato}{butyl}{ethyl}samarium; {[N-(2,6-bis(diphenylphosphino)-phenyl)-C-(propyl)-N-(2,6-didodecyl-phenyl)]amidinato}di-{propyl}cerium; {[N-(2,6-didecyl-phenyl)-C-(octadecyl)-N-(2,6-dipentyl-phenyl)]amidinato}{propyl}{ethyl}yttrium; {[N-(2,6-dipentyl-phenyl)-C-(methyl)-P-(2,6-diiodo-phenyl)]phosphoamidinato}di-{ethyl}gadolinium; {[N-(2,6-bis(diphenylphosphino)-phenyl)-C-(ethyl)-N-(2,6-bis(dibutylamino)-phenyl)]amidinato}{tridecyl}{4-methylphenoxy}neodymium; {[N-(2,6-dipentyl-phenyl)-C-(hydrido)-N-(2,6-dibenzyl-phenyl)]amidinato}{octyl}{ethyl}europium; {[N-(2,6-dihexadecyl-phenyl)-C-(butylamino)-N-(2,6-diphenyl-phenyl)]amidinato}{propyl}{butyl}cerium; {[N-(2,6-dioctadecyl-phenyl)-C-(methyl)-N-(2,6-diheptyl-phenyl)]amidinato}{diethylphosphino}{butyl}praseodymium; {[P-(2,6-dibutyl-phenyl)-C-(methyl)-P-(2,6-dihexyl-phenyl)]phosphoamidinato}{decyl}{hydrido}yttrium; {[N-(2,6-dipentadecyl-phenyl)-C-(diphenylphosphino)-N-(2,6-ditridecyl-phenyl)]amidinato}{hydrido}{ethyl}cerium; {[N-(2,6-dihexadecyl-phenyl)-C-(ethyl)-N-(2,6-diiodo-phenyl)]amidinato}{tridecyl}{methyl}cerium; {[N-(2,6-dipentyl-3-perfluorophenyl-phenyl)-C-(propyl)-N-(2,6-ditrimethylsilylethyl-3-perfluorophenyl-phenyl]amidinato}{methyl}{ethyl}yttrium; {[N-(2,6-dihexadecyl-phenyl)-C-(pentyl)-N-(2,6-bis(dimethylamino)-phenyl)]amidinato}{methyl}{butyl}europium; {[N-(2,6-ditriethylsilylmethyl-4-ethyl-phenyl)-C-(methyl)-N-(2,6-dibutyl-4-ethyl-phenyl]amidinato}{propyl}{butyl}yttrium; {[N-(2,6-dipentyl-phenyl)-C-(propyl)-N-(2,6-didecyl-phenyl)]amidinato}{propyl}{methyl}neodymium; {[N-(2,6-didecyl-phenyl)-C-(ethyl)-N-(2,6-bis(diphenylphosphino)-phenyl)]

amidinato}{methylethylamino}{dimethylamino}neodymium; {[N-(2,6-diiodo-phenyl)-C-(iodo)-N-(2,6-diheptyl-phenyl)]amidinato}di-{propyl}cerium; {[N-(2,6-dihexadecyl-phenyl)-C-(hydrido)-N-(2,6-dibutyl-phenyl)]amidinato}{iodo}{methyl}cerium; {[N-(2,6-didodecyl-phenyl)-C-(propyl)-N-(2,6-bis(dibutylamino)-phenyl)]amidinato}{phenyl}{undecyl}praseodymium; {[P-(2,6-ditridecyl-phenyl)-C-(propyl)-P-(2,6-dinonadecyl-phenyl)]phosphoamidinato}{hexyl}{ethyl}yttrium; {[N-(2,6-ditriethylsilylmethyl-phenyl)-C-(nonyl)-N-(2,6-diheptyl-phenyl)]amidinato}{methyl}{butyl}praseodymium; {[N-(2,6-didodecyl-phenyl)-C-(butyl)-N-(2,6-didodecyl-phenyl)]amidinato}{methyl}{octyl}cerium; {[N-(2,6-didecyl-phenyl)-C-(hydrido)-N-(2,6-dihexyl-phenyl)]amidinato}{propyl}{dodecyl}yttrium; {[N-(2,6-dimethylethylamino-phenyl)-C-(propyl)-N-(2,6-didodecyl-phenyl)]amidinato}{hydrido}{phenyl}samarium; {[N-(2,6-diundecyl-phenyl)-C-(dibutylamino)-N-(2,6-diundecyl-phenyl)]amidinato}{ethyl}{dimethylamino}praseodymium; {[N-(2,6-dipentadecyl-4-methyl-phenyl)-C-(butyl)-N-(2,6-diheptyl-4-methyl-phenyl]amidinato}{methyl}{propyl}cerium; {[N-(2,6-dibromo-phenyl)-C-(methyl)-N-(2,6-dioctyl-phenyl)]amidinato}{butyl}{phenyl}neodymium; {[N-(2,6-diiodo-phenyl)-C-(butyl)-N-(2,6-dinonyl-phenyl)]amidinato}di-{methyl}yttrium; {[N-(2,6-dipentadecyl-phenyl)-C-(butyl)-P-(2,6-didecyl-phenyl)]phosphoamidinato}{methyl}{hydrido}europium; {[N-(2,6-diundecyl-phenyl)-C-(diethylphosphino)-N-(2,6-diphenyl-phenyl)]amidinato}di-{methyl}cerium; {[N-(2,6-bis(dibutylamino)-phenyl)-C-(hexadecyl)-N-(2,6-dibromo-phenyl)]amidinato}{diethylphosphino}{propyl}gadolinium; {[N-(2,6-dimethylethylamino-phenyl)-C-(undecyl)-N-(2,6-dibenzyl-phenyl)]amidinato}{butyl}{propyl}cerium; {[N-(2,6-dinonadecyl-phenyl)-C-(butyl)-N-(2,6-dibenzyl-phenyl)]amidinato}{methyl}{iodo}yttrium; {[N-(2,6-dinonadecyl-phenyl)-C-(propyl)-N-(2,6-dihexadecyl-phenyl)]amidinato}{phenyl}{butyl}yttrium; {[N-(2,6-dinonyl-phenyl)-C-(hydrido)-N-(2,6-bis(diphenylphosphino)-phenyl)]amidinato}{propyl}{butyl}yttrium; {[N-(2,6-dinonadecyl-phenyl)-C-(methyl)-N-(2,6-diheptadecyl-phenyl)]amidinato}{butyl}{ethyl}yttrium; {[N-(2,6-diphenyl-4-butyl-phenyl)-C-(nonyl)-N-(2,6-didecyl-4-butyl-phenyl]amidinato}{tridecyl}{perfluorophenyl}yttrium; {[N-(2,6-dibutyl-phenyl)-C-(bromo)-N-(2,6-ditridecyl-phenyl)]amidinato}{heptyl}{methylethylamino}neodymium; {[N-(2,6-dihexadecyl-phenyl)-C-(butyl)-N-(2,6-dinonadecyl-phenyl)]amidinato}{propyl}{methyl}yttrium; {[N-(2,6-dipropyl-phenyl)-C-(methyl)-N-(2,6-ditetradecyl-phenyl)]amidinato}{butyl}{hexyl}yttrium; {[N-(2,6-diundecyl-phenyl)-C-(ethyl)-N-(2,6-didodecyl-phenyl)]amidinato}{ethyl}{hydrido}cerium; {[N-(2,6-ditridecyl-phenyl)-C-(hydrido)-N-(2,6-dichloro-phenyl)]amidinato}{propyl}{methylethylamino}samarium; {[N-(2,6-ditriethylsilylmethyl-phenyl)-C-(ethyl)-N-(2,6-dibutylamino-phenyl)]amidinato}{propyl}{butylamino}neodymium; {[N-(2,6-dipropyl-4-ethyl-phenyl)-C-(methyl)-N-(2,6-di4-methylphenoxy-4-ethyl-phenyl]amidinato}{ethyl}{butyl}yttrium; {[N-(2,6-bis(diethylamino)-3-propyl-phenyl)-C-(propyl)-N-(2,6-dinonyl-3-propyl-phenyl]amidinato}{4-methylphenoxy}{nonyl}yttrium; {[N-(2,6-bis(diethylamino)-phenyl)-C-(propyl)-N-(2,6-dichloro-phenyl)]amidinato}{iodo}{methyl}yttrium; {[N-(2,6-dihexyl-phenyl)-C-(ethyl)-N-(2,6-dinonadecyl-phenyl)]amidinato}{octyl}{hydrido}praseodymium; {[N-(2,6-diheptyl-phenyl)-C-(methylethylamino)-N-(2,6-dinonadecyl-phenyl)]amidinato}{triethylsilylmethyl}{butyl}europium; {[N-(2,6-dibenzyl-phenyl)-C-(chloro)-N-(2,6-dibutyl-phenyl)]amidinato}{diethylphosphino}{undecyl}samarium.

The following structures are shown to exemplify the naming convention used above:

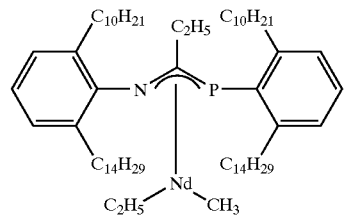

{[N-(2-decyl-6-tetradecyl-phenyl)-C-(ethyl)-P-(2-decyl-6-tetradecyl-phenyl)]phosphoamidinato}{ethyl}{methyl}neodymium The "phosphoamidinato" portion of the above name indicates that the backbone of the ancillary ligand comprises N, C, and P. Working backwards in the name, the "P-(2-decyl-6-tetradecyl-phenyl)" portion of the name indicates that a substituted phenyl ring connects to the phosphorous of the ancillary ligand backbone. The phenyl ring is substituted at its 2 and 6 position with a decyl and a tetradecyl radical, respectively. The "C-(ethyl)-" portion of the name indicates that an ethyl radical connects to the carbon atom of the ancillary ligand backbone. Substituents taking the position of this ethyl group are sometimes referred to as apical substitutents. The final portion of the ancillary ligand is "N-(2-decyl-6-tetradecyl-phenyl)". It indicates that a substituted phenyl ring connects to the nitrogen of the ancillary ligand backbone. As can be seen, the phenyl ring is substituted in the same way as discussed above. The remainder of the name represents the transition metal center, in this case neodymium, and the ligands identified as Q, above, in this case ethyl and methyl.

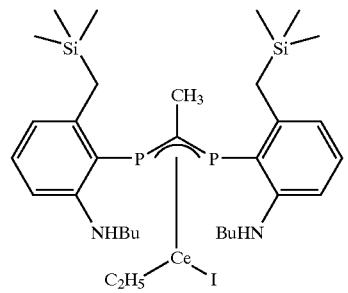

{[P-(2-butylamino-6-trimethylsilylethyl-phenyl)-C-(methyl)-P-(2-butylamino-6-trimethylsilylethyl-phenyl)]phosphoamidinato}{ethyl}{iodo}cerium

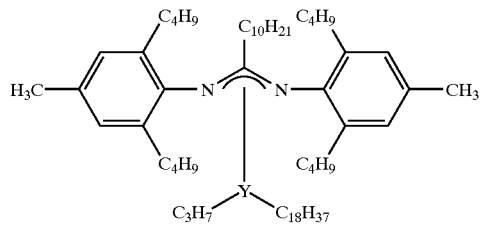

{[N-(2,6-dibutyl-4-methyl-phenyl)-C-(decyl)-N-(2,6-dibutyl-4-methyl-phenyl] amidinato}{propyl}{octadecyl}yttrium

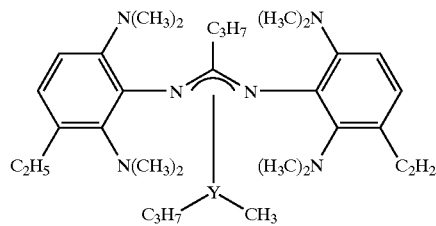

{[N-(2,6-bis(dimethylamino)-3-ethyl-phenyl)-C-(propyl)-N-(2,6-bis(dimethylamino)-3-ethyl-phenyl] amidinato}{methyl}{propyl}yttrium

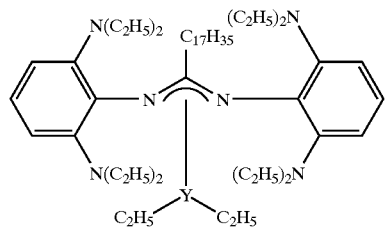

{[N-(2,6-bis(diethylamino)-phenyl)-C-(heptadecyl)-N-(2,6-bis(diethylamino)-phenyl)]amidinato}di-{ethyl}yttrium

EXAMPLES

The following examples are presented to illustrate the discussion above. Although the examples may be directed toward certain invention embodiments, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, and THF=tetrahydrofuran.

All parts, proportions, and percentages are by weights unless otherwise indicated. All molecular weights are weight average molecular weight unless otherwise noted. (The isolated yields of the compounds synthesized are given in mol %).

Molecular weights (weight average molecular weight (Mw) and number average molecular weight (Mn)) were measured by Gel Permeation Chromatography. Reported GPC data (Mw, Mn and Mw/Mn) that are labeled with "[a]", were determined as follows: Gel permeation chromatography (GPC) analysis was carried out on a Polymer Laboratories Ltd. (PL-GPC210) chromatograph using 1,2,4-trichlorobenzene (TCB) as the mobile phase at 150° C. The samples were prepared by dissolving the polymer in the mobile phase solvent in an external oven at 0.1% (weight/volume) and were run without filtration (column: 4PL-Gel Mixed A). The molecular weight was referenced polystyrene (Mw=65500, PDI=1.02) standards. The polystyrene was used for column calibration—single point calibration for Triple Detector (RI+Visco+LS, 90°) (VISCOTEK™, Software: TRISEC™).

Reported GPC data (Mw, Mn and Mw/Mn) that are labeled with [b]) were determined as following: GPC measurements were carried out by high temperature GPC at 150° C., using 1,2,4-trichlorobenzene as solvent and narrow MWD polystyrene standard sample as reference. The measurements were performed on PL-GPC210 chromatograph with 4PL-Gel Mixed A Columns, RALLS™ lightscattering detector (Precision Detector, RI+LS, 15°+90°, PD2040 at 800 nm), H502 Viscometer (VISCOTEK™), refractive detector and DM 400 datamanager (VISCOTEK™). Every value is the average of two independent measurements.

Reported GPC data (Mw, Mn and Mw/Mn) that are labeled with "[c]") were determined as follows: GPC measurements were carried out by using a Waters 150 Gel Permeation Chromatograph. This chromatograph was equipped with a differential refractive index detector and calibrated using polystyrene standards. Samples were run in either THF (45° C.) or in 1,2,4-trichlorobenzene (145° C.), depending upon the sample's solubility, using three Shodex GPC AT-80 M/S columns in series. This general technique is discussed in "Liquid Chromatography of Polymers and Related Materials III'" J. Cazes Ed., Marcel Decker, 1981, page 207. No column spreading corrections were employed but data on generally accepted standards, e.g. National Bureau of Standards Polyethylene 1475, demonstrated a precision with 0.1 units for $M_w/M_n$, which was calculated from elution times. Numerical analyses were performed using Expert Ease® software available from Waters Corporation.

All preparations were performed under an inert nitrogen atmosphere, using standard Schlenk or glovebox techniques, unless mentioned otherwise. Dry solvents (toluene, THF, diethyl ether, pentane, hexane) were distilled from sodium or Na/K alloy before use. The toluene used in the polymerization experiments (Aldrich anhydrous, 99.5%) was passed through columns with alumina (Fluka™), supported copper scavenger (BASF R3-11™) and molecular sieves (4 Å). Ethylene (AGA polymer grade) was passed through columns with supported copper scavenger (BASF R3-11™) and molecular sieves (4 Å) before being passed to the reactor. Deuterated solvents were either dried on Na/K alloy and vacuum transferred before use ($C_6D_6$, THF-$d_8$, toluene-$d_8$), or degassed and dried on 4 Å molecular sieves ($C_6D_5Br$).

Example 1

Synthesis of N,N'-Bis-(2,6-diisopropylphenyl) benzamidine

A stirred mixture of $P_2O_5$ (1.5 g, 10.5 mmol), hexamethyldisiloxane (3.35 mL, 16 mmol) and dichloromethane (3 mL) was refluxed for 30 minutes. The volatiles were removed by distilling the mixture at 160° C. Benzoic acid (0.152 g, 1.25 mmol) and 2,6-diisopropylaniline (0.47 mL, 2.5 mmol) were added to the viscous syrup, and this mixture was heated at 170° C. for 6 hours. The mixture was poured into a 1 M KOH solution (50 mL), producing oil that solidified in the course of two days. The solid was washed with water, then crystallized from ethanol/water to give 0.3 g (54%) of the amidine product. MP 128° C.; IR (Nujol) 3362 (NH), 1611 cm$^{-1}$ (C=N). $^1$H NMR (CDCl$_3$): δ 6.8–7.4 (m, 11H total, Ar), 5.70 (s, 1H, NH), 3.23 and 3.16 (overlapping sept, 4H total, Pr$^i$ CH), 1.35 (d, J=7.1 Hz, 6H, Pr$^i$ Me), 1.23 (d, J=6.8 Hz, 6H, Pr$^i$ Me), 0.98 (d, J=6.8 Hz, 6H, Pr$^i$ Me), 0.84 (d, J=6.8 Hz, 6H, Pr$^i$ Me). $^{13}$C NMR (CDCl$_3$, APT): δ 153.5 (NCN), 145.0, 139.2, 134.8, 134.0 (Ar C), 129.0, 128.6, 127.6, 127.4, 123.5, 123.3 and 123.1 (Ar CH), 28.3 and 28.1 (Pr$^i$ CH), 24.9, 24.2, 22.2 and 22.1 (Pr$^i$ Me). MS (EI); m/z (%)=440 [M$^+$] (15.6), 264 (100). HRMS: calcd. for C$_{31}$H$_{40}$N$_2$: 440.670; found 440.318. Anal. [C$_{31}$H$_{40}$N$_2$] (440.67) calcd: C, 84.49; H, 9.15; N, 6.36. Found: C, 84.45; H, 9.25; N, 6.33.

Alternatively, the compound was prepared from the corresponding imidoyl chloride and 2,6-diisopropyl aniline. A solution of 2,6-diisopropylaniline (0.885 g, 5 mmol), triethylamine (2.5 mL), and N-2,6-diisopropylbenzimidoyl chloride (1.50 g, 5 mmol) in 10 mL of toluene was refluxed for 24 h. The mixture was washed with water, dried (over Na$_2$SO$_4$), and concentrated. After a single crystallization from ethanol/water, 1.88 g (85%) of the benzamidine was obtained; it was identical to the compound described above as seen by MP and NMR spectroscopy.

Example 2

Synthesis of [PhC(N-2,6-Pr$^i{}_2$C$_6$H$_3$)$_2$]Y(CH$_2$SiMe$_3$)$_2$ (THF)

A solution of (Me$_3$SiCH$_2$)$_3$Y(THF)$_2$ (0.31 g, 0.63 mmol) in pentane (30 ml) was reacted with [PhC(N-2,6-Pr$^i{}_2$C$_6$H$_3$)$_2$]H (0.27 g, 0.63 mmol) at room temperature. The reaction mixture was stirred for 3 hours, after which the volatiles were removed under vacuum. Residual THF was removed from the remaining sticky solid by stirring with pentane (5 ml), which was subsequently removed under vacuum. Extracting with pentane (2×20 ml) and concentrating and cooling the extract to −30° C. gave the crystalline product (0.40 g, 0.51 mmol, 64%). The identity of the product was confirmed by single crystal X-ray diffraction.

$^1$H NMR (300 MHz, C$_6$D$_6$): δ 7.11–7.08 (m, 2H, Ar—Pr$^i{}_2$), 7.00 (m, 5H, Ph), 6.65–6.61 (m, 4H, Ar—Pr$^i{}_2$), 3.69 (m, 4H α-THF), 3.61 (sept, $^3$J$_{HH}$=6.6 Hz, 4H, CHMe$_2$), 1.37 (d, $^3$J$_{HH}$=6.6 Hz, 12H, CHMe$_2$), 1.14 (m, 4H β-THF), 1.01 (d, $^3$J$_{HH}$=6.6 Hz, 12H, CHMe$_3$), 0.29 (s, 18H, CH$_2$SiMe$_3$), −0.11 (d, $^2$J$_{YH}$=3.0 Hz, 4H, CH$_2$SiMe$_3$).

$^{13}$C NMR (75.4 MHz, C$_6$D$_6$): δ 174.8 (NCN), 143.2 (ipso-Ph), 142.2 (ipso-C$_6$H$_3$), 132.2 (C$_6$H$_3$ C), 130.4 (d, $^1$J$_{CH}$=159.8 Hz, Ar CH), 129.2 (d, $^1$J$_{CH}$=161.1 Hz, Ar CH), 127.0 (d, $^1$J$_{CH}$=158.6 Hz, Ar CH), 124.7 (d, $^1$J$_{CH}$=158.6 Hz, Ar CH), 123.9 (d, $^1$J$_{CH}$=150.0 Hz, Ar CH), 70.7 (t, $^1$J$_{CH}$=147.6 Hz, α-THF), 39.5 (dt, $^1$J$_{YC}$=40.3 Hz, $^1$J$_{CH}$=100.1 Hz, YCH$_2$SiMe$_3$), 28.6 (d, $^1$J$_{CH}$=126.9 Hz, CHMe$_2$), (q, $^1$J$_{CH}$=126.9 Hz, CHMe$_2$), 24.9 (t, $^1$J$_{CH}$=124.4 Hz, β-THF), 23.5 (q, $^1$J$_{CH}$=125.7 Hz, CHMe$_2$), 4.2 (q, J$_{CH}$=117.2 Hz, YCH$_2$SiMe$_3$).

Anal. [C$_{43}$H$_{69}$N$_2$OSi$_2$Y] (775.11) calcd: C, 66.63; H, 8.97; N, 3.61; Y, 11.47. Found: C, 66.16; H, 8.95; N, 3.54; Y, 11.32.

Example 3

Reaction of [PhC(N-2,6-Pr$^i{}_2$C$_6$H$_3$)$_2$]Y(CH$_2$SiMe$_3$)$_2$ (THF) with [HNMe$_2$Ph][B(C$_6$F$_5$)$_4$]

A solution of [PhC(N-2,6-Pr$^i{}_2$C$_6$H$_3$)$_2$]Y(CH$_2$SiMe$_3$)$_2$ (THF) (23 mg, 30.0 μmol) in THF-d$_8$ (0.6 ml) was reacted with [HNMe$_2$Ph][B(C$_6$F$_5$)$_4$] (24 mg, 30.0 μmol). The resulting solution was transferred to an NMR tube and analyzed by NMR spectroscopy, which showed full conversion to the cationic species {[PhC(N-2,6-Pr$^i{}_2$C$_6$H$_3$)$_2$]Y(CH$_2$SiMe$_3$)(THF-d$_8$)$_n$}[B(C$_6$F$_5$)$_4$], SiMe$_4$, and free PhNMe$_2$.

$^1$H NMR (500 MHz, THF-d$_8$): δ 7.12–7.09 (m, 2H, Ar—Pr$^i{}_2$), 7.06 (m, 5H, Ph), 6.96–6.94 (m, 4H, Ar—Pr$^i{}_2$), 3.33 (sept, $^3$J$_{HH}$=6.50 Hz, 4H, CHMe$_2$), 2.87 (s, 6H, Me$_2$NPh), 1.24 (d, $^3$J$_{HH}$=6.5 Hz, 12H, CHMe$_2$), 0.86 (d, $^3$J$_{HH}$=6.5 Hz, 12H, CHMe$_2$), −0.02 (s, 9H, CH$_2$SiMe$_3$), −0.15 (d, $^2$J$_{YH}$=3.0 Hz, 2H, CH$_2$SiMe$_3$).

6.96 (d, $^3$J$_{HH}$=8.50 Hz, 4H, Me$_2$NPh), 6.67 (d, $^3$J$_{HH}$=8.00 Hz, 2H, Me$_2$NPh), 6.58 (t, $^3$J$_{HH}$=7.00 Hz, 1H, Me$_2$NPh), $^{13}$C{$^1$H} NMR (125.7 MHz, THF-d$_8$): δ 179.3 (NCN), 144.4 (ipso-Ar), 143.5 (ipso-Ar), 132.5 (Ar), 132.2 (Ar), 131.8 (Ar), 130.4 (Ar), 128.7 (Ar), 127.1 (Ar), 126.7 (Ar), 42.3 (d, $^1$J$_{YC}$=42.73 Hz, YCH$_2$SiMe$_3$), 29.7 (CHMe$_3$), 26.0 (CHMe$_3$), 25.9 (m, β-THF), 24.5 (CHMe$_3$), 4.8 (YCH$_2$SiMe$_3$).

$^{19}$F NMR (188.15 MHz, 20° C., C$_6$D$_5$Br) δ: −133.89 (o-CF), −165.98 (p-CF), −169.48 (m-CF).

Example 4

Ethylene Polymerization with {PhC(N-2,6-Pr$^i{}_2$C$_6$H$_3$)$_2$}Y(CH$_2$SiMe$_3$)$_2$(THF) and [HNMe$_2$Ph][B(C$_6$F$_5$)$_4$]

In a drybox, solutions of [PhC(N-2,6-Pr$^i{}_2$C$_6$H$_3$)$_2$]Y(CH$_2$SiMe$_3$)$_2$(THF) (10 μmol) and [HNMe$_2$Ph][B(C$_6$F$_5$)$_4$] (10 μmol), each in 10 ml of toluene were prepared. These were stored in separate serum-capped vials. Polymerization was performed in a stainless steel 0.5 L autoclave, pre-dried and flushed with nitrogen, charged with 150 ml of dry toluene, equilibrated at the desired reaction temperature (50° C. in this example), and pressurized with ethylene (5 bar). The solution of [HNMe$_2$Ph][B(C$_6$F$_5$)$_4$] was injected into the reactor first (using a pneumatically operated injector), and the reaction was started by subsequently injecting the [PhC(N-2,6-Pr$^i{}_2$C$_6$H$_3$)$_2$]Y(CH$_2$SiMe$_3$)$_2$(THF) solution. The ethylene pressure was kept constant during the reaction by providing a replenishing flow. The reactor was stirred for the required reaction time and then vented. The polymer was repeatedly rinsed with methanol and dried in a vacuum oven. Experiments were carried out at 50° C. with run times of 5, 10, 20 and 30 minutes. The results are summarized in Table 1.

TABLE 1

Ethylene polymerization with [{PhC(N-2,6-Pr$^i{}_2$C$_6$H$_3$)$_2$}Y(CH$_2$SiMe$_3$)$_2$THF] and [HNMe$_2$Ph][B(C$_6$F$_5$)$_4$]

| Run Time (min) | Ethylene Pressure (bar) | PE (g) | Productivity (kg mol$^{-1}$bar$^{-1}$h$^{-1}$) | M$_w$ | M$_w$/M$_n$ |
|---|---|---|---|---|---|
| 5 | 5 | 4.15 | 1037 | 429600[a] | 1.21[a] |
|  |  |  |  | 656700[b] | 1.32[b] |
|  |  |  |  | 418981[c] | 1.71[c] |
| 10 | 5 | 6.35 | 793 | 643700[a] | 1.18[a] |
|  |  |  |  | 943000[b] | 1.26[b] |
|  |  |  |  | 501680[c] | 2.02[c] |
| 20 | 5 | 7.61 | 461 | 854400[a] | 1.24[a] |
|  |  |  |  | 1362000[b] | 1.91[b] |
|  |  |  |  | 931745[c] | 2.48[c] |

TABLE 1-continued

Ethylene polymerization with [{PhC(N-2,6-Pr$^i_2$C$_6$H$_3$)$_2$} Y(CH$_2$SiMe$_3$)$_2$THF] and [HNMe$_2$Ph][B(C$_6$F$_5$)$_4$]

| Run Time (min) | Ethylene Pressure (bar) | PE (g) | Productivity (kg mol$^{-1}$bar$^{-1}$h$^{-1}$) | $M_w$ | $M_w/M_n$ |
|---|---|---|---|---|---|
| 30 | 5 | 10.00 | 400 | 1269000[a] | 1.14[a] |
|  |  |  |  | 2292000[b] | 1.63[b] |
|  |  |  |  | 1210714[c] | 2.21[c] |

Conditions:
10 μmol catalyst, 1 equiv. of [HNMe$_2$Ph][B(C$_6$F$_5$)$_4$], 5 bar ethylene, 50° C., stirring speed 605 rpm, 170 ml toluene, 0.5 L stainless steel autoclave
[a,b,c]GPC analysis techniques as described in the general section.

Example 5

Synthesis of [PhC(N-2,6-Pr$^i_2$C$_6$H$_3$)$_2$]Sc(CH$_2$SiMe$_3$)$_2$(THF)

Method (a): A solution of (Me$_3$SiCH$_2$)$_3$Sc(THF)$_2$ (0.45 g, 1.00 mmol) in pentane (30 ml) was reacted with [PhC(N-2,6-Pr$^i_2$C$_6$H$_3$)$_2$]H (0.44 g, 1.00 mmol) at room temperature. The reaction mixture was stirred for 3 hours, after which the volume of the solution was reduced to ca. 10 ml. Cooling to −30° C. gave the product (0.55 g, 0.76 mmol, 76.%).

Method (b): To a suspension of ScCl$_3$(THF)$_3$ (0.36 g, 1.00 mmol) in THF (60 m), LiCH$_2$SiMe$_3$ (0.28 g, 3.00 mmol) was added at ambient temperature. The mixture was stirred overnight, after which [PhC(N-2,6-Pr$^i_2$C$_6$H$_3$)$_2$]H (0.44 g, 1.00 mmol) was added. The solution was stirred for three hours after which the volatiles were removed under vacuum. Residual THF was removed from the solids by stirring with pentane (5 ml). The pentane was subsequently removed under vacuum. The mixture was extracted with pentane (2×50 ml), the extract was concentrated to 20 ml and cooled (−30° C.) yielding the pure product (0.51 g, 70.0%).

$^1$H NMR (500 MHz, C$_6$D$_6$, δ): 7.14–7.13 (m, 2H, C$_6$H$_3$), 7.04 (m, 5H, Ph), 6.62–6.60 (m, 4H, C$_6$H$_3$), 3.80 (m, 4H α-THF), 3.65 (sept, $^3J_{HH}$=6.5 Hz, 4H, CHMe$_2$), 1.38 (d, $^3J_{HH}$=6.5 Hz, 12H, CHMe$_2$), 1.24 (m, 4H β-THF), 0.95 (d, $^3J_{HH}$=6.5 Hz, 12H, CHMe$_2$), 0.42 (br, 4H, CH$_2$SiMe$_3$), 0.26 (s, 18H, CH$_2$SiMe$_3$).

$^1$H NMR (500 MHz, C$_7$D$_8$, −60° C., δ): 7.16–7.14 (m, 2H, C$_6$H$_3$), 7.07 (m, 5H, Ph), 6.51–6.50 (m, 4H, C$_6$H$_3$), 3.89 (sept, $^3J_{HH}$=6.5 Hz, 2H, CHMe$_2$), 3.77 (m, 4H α-THF), 3.44 (sept, $^3J_{HH}$=6.5 Hz, 2H, CHMe$_2$), 1.66 (d, $^3J_{HH}$=6.5 Hz, 6H, CHMe$_2$), 1.20 (d, $^3J_{HH}$=6.5 Hz, 6H, CHMe$_2$), 1.05 (d, $^3J_{HH}$=6.5 Hz, 6H, CHMe$_2$), 1.04 (m, 4H β-THF), 0.82 (d, $^3J_{HH}$=6.5 Hz, 6H, CHMe$_2$), 0.63 (d, $^2J_{HH}$=11.1 Hz, 2H, CH$_2$SiMe$_3$), 0.34 (s, 18H, CH$_2$SiMe$_3$), 0.24 (d, $^2J_{HH}$=11.1 Hz, 2H, CH$_2$SiMe$_3$).

$^{13}$C NMR (125.7 MHz, C$_6$D$_6$, δ): 175.4 (NCN), 143.2 (Ph ipso-C), 142.6 (C$_6$H$_3$ ipso-C), 131.5 (C$_6$H$_3$C), 130.8 (d, $^1J_{CH}$=150.8 Hz, C$_6$H$_3$), 129.6 (d, $^1J_{CH}$=157.8 Hz, Ph), 127.1 (d, $^1J_{CH}$=158.2 Hz, Ph), 125.1 (d, $^1J_{CH}$=157.9 Hz, Ph), 124.2 (d, $^1J_{CH}$=156.1 Hz, C$_6$H$_3$), 71.3 (t, $^1J_{CH}$=145.6 Hz, α-THF), 45.0 (t, $^1J_{CH}$=95.5 Hz, ScCH$_2$SiMe$_3$), 28.4 (d, $^1J_{CH}$=129.8 Hz, CHMe$_2$), 25.8 (q, $^1J_{CH}$=126.3 Hz, CHMe$_2$), 25.3 (t, $^1J_{CH}$=135.1 Hz, β-THF), 24.0 (q, $^1J_{CH}$=124.6 Hz, CHMe$_2$), 3.9 (q, J$_{CH}$=117.5 Hz, ScCH$_2$SiMe$_3$).

Anal. [C$_{43}$H$_{69}$N$_2$OSi$_2$Sc] (731.16) calcd.: C, 70.64; H, 9.51; N, 3.83. Found: C, 70.40; H, 9.63; N, 3.83.

Example 6

Ethylene Polymerization with {PhC(N-2,6-Pr$^i_2$C$_6$H$_3$)$_2$}Sc(CH$_2$SiMe$_3$)$_2$(THF) and [HNMe$_2$Ph][B(C$_6$F$_5$)$_4$]

An ethylene polymerization experiment was performed with 10 μmol of {PhC(N-2,6-Pr$^i_2$C$_6$H$_3$)$_2$}Sc(CH$_2$SiMe$_3$)$_2$ (THF) and [HNMe$_2$Ph][B(C$_6$F$_5$)$_4$] activator, following the general procedure described in example 4. The reactor temperature was 50° C., and the run time was 5 minutes. This yielded 0.68 g of polyethylene (productivity 108.8 kg polymer/mol Y.h.bar; GPC: Mw=105000, Mw/Mn=1.92).

Example 7

Synthesis of N,N'-Bis-(2,6-diisopropylphenyl)-pentafluorobenzamidine

A stirred mixture of P$_2$O$_5$ (10.65 g, 37.5 mmol), hexamethyldisiloxane (17 mL, 80 mmol) and dichloromethane (15 mL) was refluxed for 30 minutes. The volatiles were distilled off by heating the mixture to 160° C. Pentafluorobenzoic acid (1.26 g, 6.25 mmol) and 2,6-diisopropylphenylamine (2.5 mL, 13.3 mmol) were added to the viscous syrup, and this mixture was heated at 160° C. for 19 hours. The mixture was poured into a 1 M KOH solution (200 mL), and this was extracted with ether (100, 100 and 50 mL). The combined extracts were concentrated and the concentrate was filtered through a layer of alumina (3 cm cross section) The filtrate was concentrated and crystallized from ethanol/water to give 1.65 g (50%) of the amidine, MP 166–168° C.

IR (Nujol) 3376 (NH), 1636 cm$^{-1}$ (C=N). $^1$H NMR (CDCl$_3$) δ 7.19 (d, J=8.0 Hz, 2H, o-Ar), 7.10 (ps. t, 2H total, p-Ar), 6.94 (d, J=7.7 Hz, 2H, o-Ar), 5.78 (s, 1H, NH), 3.28 and 3.19 (overlapping sept, 4H total, Pr$^i$ CH), 1.33 (d, J=7.0 Hz, 6H, Pr$^i$ Me), 1.15 (d, J=7.0 Hz, 6H, Pr$^i$ Me), 1.08 (d, J=6.6 Hz, 6H, Pr$^i$ Me), 0.84 (d, J=6.6 Hz, 6H, Pr$^i$ Me).

$^{13}$C NMR (CDCl$_3$, APT) δ 144.1, 142.1, 139.3, 136.4, 128.8 (C), CF's broad, 125.9, 122.0, 121.0, and 120.8 (Ar CH), 25.9 and 25.5 (Pr$^i$ CH), 23.2, 21.9, 19.7 and 19.0 (Pr$^i$ Me). MS (EI); m/z (%)=530 [M$^+$] (31), 354 (100). HRMS: calcd. for C$_{31}$H$_{35}$N$_2$F$_5$: 530.272; found 530.271. Anal. [C$_{31}$H$_{35}$N$_2$F$_5$] (530.27) calcd: C, 70.17; H, 6.65; N, 5.28. Found: C, 70.15; H, 6.60; N, 5.27.

Example 8

Synthesis of [C$_6$F$_5$C(N-2,6-Pr$^i_2$C$_6$H$_3$)$_2$]Y(CH$_2$SiMe$_3$)$_2$(THF)

A solution of (Me$_3$SiCH$_2$)$_3$Y(THF)$_2$ (0.49 g, 1.00 mmol) in pentane (30 ml) was reacted with [C$_6$F$_5$C(N-2,6-Pr$^i_2$C$_6$H$_3$)$_2$]H (0.27 g, 0.53 mmol) at room temperature. The reaction mixture was stirred for 3 hours, after which the volatiles were removed under vacuum. Residual THF was removed from the remaining sticky solid by stirring with pentane (5 ml), which was also subsequently removed under vacuum. Extracting with pentane (3×20 ml) and concentrating and cooling the extract to −30° C. gave the product (0.60 g, 0.70 mmol, 70%).

$^1$H NMR (300 MHz, C$_6$D$_6$): δ 6.98–6.89 (m, 6H, C$_6$H$_3$), 3.59 (sept, $^3J_{HH}$=6.6 Hz, 4H, CHMe$_2$), 3.55 (m, 4H α-THF), 1.30 (d, $^3J_{HH}$=6.6 Hz, 12H, CHMe$_2$), 1.19 (d, $^3J_{HH}$=6.6 Hz, 12H, CHMe$_2$), 1.14 (m, 4H β-THF), 0.28 (s, 18H, CH$_2$SiMe$_3$), −0.05 (d, $^2J_{YH}$=3.3 Hz, 4H, CH$_2$SiMe$_3$). $^{13}$C NMR (75.4 MHz, C$_6$D$_6$): δ 177.7 (NCN), 143.6 (C$_6$H$_3$ ipso-C), 143.1 (d, $^1J_{CH}$=250.2 Hz, CF), 141.1 (C$_6$F$_5$, ipso-C), 138.1 (d, $^1J_{CH}$=245.8 Hz, CF), 137. (d, $^1J_{CH}$=254.9 Hz, CF), 128.7 (C$_6$H$_3$ ipso-C), 125.7 (d, $^1J_{CH}$=159.8 Hz, C$_6$H$_3$), 123.8 (d, $^1J_{CH}$=156.2 Hz, C$_6$H$_3$), 69.7 (t, $^1J_{CH}$=152.5 Hz, α-THF), 41.2 (dt, $^1J_{CH}$=101.3 Hz, $^1J_{YC}$=41.5 Hz, YCH$_2$SiMe$_3$), 28.3 (d, $^1J_{CH}$=126.9 Hz, CHMe$_2$), 26.9 (q, $^1J_{CH}$=125.7 Hz, CHMe$_2$), 25.0 (t, $^1J_{CH}$=135.4 Hz, β-THF), 23.0 (q, $^1J_{CH}$=126.9 Hz, CHMe$_2$), 4.2 (q, J$_{CH}$=118.4 Hz, YCH$_2$SiMe$_3$).

$^{19}$F NMR (188.15 MHz, 20° C., C$_6$D$_6$) δ: −132.41 (d, $^3$J$_{FF}$=19 Hz, o-CF), −151.35 (t, $^3$J$_{FF}$=21 Hz, p-CF), −161.77 (d, $^3$J$_{FF}$=17 Hz, m-CF). Anal. [C$_{43}$H$_{64}$F$_5$N$_2$OSi$_2$Y] (865.06) calcd: C, 59.70; H, 7.46; N, 3.24; Y, 10.28. Found: C, 60.72; H, 7.68; N, 3.41; Y, 10.07.

Example 9

Reaction of [C$_6$F$_5$C(N-2,6-Pr$^i_2$C$_6$H$_3$)$_2$]Y(CH$_2$SiMe$_3$)$_2$(THF) with [HNMe$_2$Ph][B(C$_6$F$_5$)$_4$]

A solution of [C$_6$F$_5$C(N-2,6-Pr$^i_2$C$_6$H$_3$)$_2$]Y(CH$_2$SiMe$_3$)$_2$(THF) (31.1 mg, 36 μmol) in THF-d$_8$ (0.6 ml) was reacted with [HNMe$_2$Ph][B(C$_6$F$_5$)$_4$] (28.8 mg, 36 μmol). The obtained solution was transferred to an NMR tube and analyzed by NMR spectroscopy, which showed full conversion to the cationic species {[C$_6$F$_5$C(N-2,6-Pr$^i_2$C$_6$H$_3$)$_2$]Y(CH$_2$SiMe$_3$)(THF-d$_8$)$_n$}[B(C$_6$F$_5$)$_4$], SiMe$_4$, and free PhNMe$_2$.

$^1$H NMR (500 MHz, THF-d$_8$): δ 7.13–7.01 (m, 6H, C$_6$H$_3$), 6.89 (t, $^3$J$_{HH}$=8.50 Hz, 2H, m-Ph), 6.64 (d, $^3$J$_{HH}$=8.50 Hz, 2H, o-Ph), 6.58 (t, $^3$J$_{HH}$=8.00 Hz, 1H, p-Ph), 3.37 (hept br, 4H, CHMe$_2$), 2.85 (s, 6H, Me$_2$NPh), 1.17 (d, $^3$J$_{HH}$=6.60 Hz, 12H CHMe$_2$), 1.10 (d, $^3$J$_{HH}$=6.6 Hz, 12H, CHMe$_2$), 0.01 (s, 12H, SiMe$_4$), −0.03 (s, 9H, CH$_2$SiMe$_3$), −0.04 (d, $^3$J$_{YH}$=2.95 Hz, 2H, CH$_2$SiMe$_3$).

$^{13}$C{$^1$H} NMR (125.7 MHz, THF-d$_8$, δ): 170.4 (NCN), 150.1 (d, $^1$J$_{CF}$=241.5 Hz, BC$_6$F$_5$), 145.4 (Cipso-C$_6$F$_5$), 144.3 (d, $^1$J$_{CF}$=251.6 Hz, C$_6$F$_5$), 143.9 (d, $^1$J$_{CF}$=251.6 Hz, BC$_6$F$_5$), 141.7 (Cipso-C$_6$F$_5$), 140.0 (d, $^1$J$_{CF}$=251.0 Hz, BC$_6$F$_5$), 139.4 (d, $^1$J$_{CF}$=241.5 Hz, C$_6$F$_5$), 139.0 (d, $^1$J$_{CF}$=249.6 Hz, BC$_6$F$_5$), 130.4 (C$_6$H$_3$), 128.1 (C$_6$H$_3$), 126.3 (C$_6$H$_3$), 45.2 (d, $^1$J$_{YC}$=42.7 Hz, YCH$_2$SiMe$_3$), 29.3 (CHMe$_3$), 27.8 (CHMe$_3$), 25.9 (m, β-THF), 24.8 (CHMe$_3$), 4.7 (YCH$_2$SiMe$_3$).

$^{19\ NMR}$ (188.15 MHz, 20° C., C$_6$D$_6$) δ: −128.4 (d, $^3$J$_{FF}$=19 Hz, o-CF, C$_6$F$_5$), −133.1 (d, $^3$J$_{FF}$=10 Hz, o-CF, B(C$_6$F$_5$)$_4$), −142.8 (t, $^3$J$_{FF}$=21 Hz, p-CF, C$_6$F$_5$), −162.7 (t, $^3$J$_{FF}$=21 Hz, p-CF, B(C$_6$F$_5$)$_4$), −160.1 (d, $^3$J$_{FF}$=17 Hz, m-CF, C$_6$F$_5$), −160.1 (d, $^3$J$_{FF}$=18 Hz, m-CF, B(C$_6$F$_5$)$_4$).

Example 10

Ethylene Polymerization with [{C$_6$F$_5$C(N-2,6-Pr$^i_2$C$_6$H$_3$)$_2$}Y(CH$_2$SiMe$_3$)$_2$THF] and [HNMe$_2$Ph][B(C$_6$F$_5$)$_4$]

Following the general procedure described in example 4, ethylene polymerization experiments were performed at four different reaction temperatures (30, 50, 80, and 100° C). The results are summarized in Table 2.

TABLE 2

Ethylene polymerization with [C$_6$F$_5$C(N-2,6-Pr$^i_2$C$_6$H$_3$)$_2$] Y(CH$_2$SiMe$_3$)$_2$(THF) and [HNMe$_2$Ph][B(C$_6$F$_5$)$_4$].

| Temp (° C.) | Run time (min) | PE (g) | Productivity (kg mol$^{-1}$bar$^{-1}$h$^{-1}$) | M$_w$ | M$_w$/M$_n$ |
|---|---|---|---|---|---|
| 30 | 10 | 0 | 0 | | |
| 50 | 10 | 0 | 0 | | |
| 80 | 20 | 5.85 | 354 | 126400$^a$ | 1.74$^a$ |
| | | | | 129580$^c$ | 1.89$^c$ |
| 100 | 20 | 1.83 | 110 | 29300$^a$ | 2.00$^a$ |
| | | | | 35031$^c$ | 2.17$^c$ |

Conditions:
10 μmol catalyst, 1 equiv. of [HNMe$_2$Ph][B(C$_6$F$_5$)$_4$], 5 bar ethylene, stirring speed 605 rpm, 170 ml toluene, 0.5 L stainless steel autoclave,
$^{a,c}$GPC analysis techniques as described in the general section.

Example 11

Ethylene Polymerization with [C$_6$F$_5$C(N-2,6-Pr$^i_2$C$_6$H$_3$)$_2$]Y(CH$_2$SiMe$_3$)$_2$(THF), [HNMe$_2$Ph][B(C$_6$F$_5$)$_4$] and B(C$_6$F$_5$)$_3$ In a drybox, solutions were made of [PhC(N-2,6-Pr$^i_2$C$_6$H$_3$)$_2$]Y(CH$_2$SiMe$_3$)$_2$(THF) (10 μmol), [HNMe$_2$Ph][B(C$_6$F$_5$)$_4$] (10 μmol) and B(C$_6$F$_5$)$_3$ (10 μmol), each in 10 ml of toluene. These solutions were prepared in separate vials sealed with a serum cap. Ethylene polymerization was performed in a stainless steel 0.5 L autoclave, pre-dried and flushed with nitrogen, charged with 150 ml of dry toluene, equilibrated at the desired reaction temperature, and pressurized with ethylene (5 bar). The solution of [HNMe$_2$Ph][B(C$_6$F$_5$)$_4$] was injected first into the reactor (using a pneumatically operated injector), and then the [PhC(N-2,6-Pr$^i_2$C$_6$H$_3$)$_2$]Y(CH$_2$SiMe$_3$)$_2$(THF) solution was injected. The reaction was started by subsequently injecting the B(C$_6$F$_5$)$_3$ solution. The ethylene pressure was kept constant during the reaction by providing a replenishing flow. The reactor was stirred for 20 minutes, after which the reactor was vented. The polymer was rinsed repeatedly with methanol and subsequently dried in a vacuum oven. The results of the polymerization experiments are summarized in Table 3.

TABLE 3

Ethylene polymerization with [C$_6$F$_5$C(N-2,6-Pr$^i_2$C$_6$H$_3$)$_2$] Y(CH$_2$SiMe$_3$)$_2$(THF), [HNMe$_2$Ph][B(C$_6$F$_5$)$_4$] and B(C$_6$F$_5$)$_3$.

| Temp (° C.) | PE (g) | Productivity (kg mol$^{-1}$ bar$^{-1}$h$^{-1}$) | M$_w$ | M$_w$/M$_n$ |
|---|---|---|---|---|
| 50 | 6.03 | 367 | 473100$^a$ | 1.52$^a$ |
| | | | 788653$^c$ | 2.57$^c$ |
| 80 | 2.00 | 121 | 130600$^a$ | 1.76$^a$ |
| | | | 151716$^c$ | 1.98$^c$ |

Conditions:
10 μmol catalyst, 1 equiv. of [HNMe$_2$Ph][B(C$_6$F$_5$)$_4$] and B(C$_6$F$_5$)$_3$, Run time 20 min, 605 rpm, 180 ml toluene, 0.5 L stainless steel autoclave, Ethylene pressure 5 bar
$^{a,c}$GPC analysis techniques as described in the general section

Example 12

Synthesis of [PhC(N-2,6-Pr$^i_2$C$_6$H$_3$)$_2$]Y(CH$_2$SiMe$_3$)$_2$(THF)$_2$ A solution of (Me$_3$SiCH$_2$)$_3$Y(THF)$_2$ (0.30 g, 0.60 mmol) in pentane (30 ml) was reacted with [PhC(N-2,6-Pr$^i_2$C$_6$H$_3$)$_2$]H (0.26 g, 0.60 mmol) at room temperature. The reaction mixture was stirred for 3 hours, after which the volume of the solution was reduced to 10 ml. Cooling to −30° C. gave the product (0.36 g, 0.43 mmol, 72%). The identity of the product was corroborated by single crystal X-ray diffraction.

$^1$H NMR (500 MHz, C$_6$D$_6$, δ): 7.10 (m, 2H, Ar), 6.99 (m, 6H, Ar), 6.63–6.61 (m, 3H, Ar), 3.64 (m, 8H α-THF), 3.61 (sept, $^3$J$_{HH}$=6.5 Hz, 8H, CHMe$_2$), 1.37 (d, $^3$J$_{HH}$=6.5 Hz, 12H, CHMe$_2$), 1.26 (m, 8H β-THF), 1.00 (d, $^3$J$_{HH}$=6.5 Hz, 12H, CHMe$_2$), 0.28 (s, 18H, CH$_2$SiMe$_3$), −0.13 (d, $^2$J$_{YH}$=2.5 Hz, 4H, CH$_2$SiMe$_3$). $^{13}$C NMR (125.7 MHz, C$_6$D$_6$, δ): 174.8 (NNCPh), 143.3 (Ph ipso-C), 142.2 (C$_6$H$_3$ ipso-C), 132.2 (C$_6$H$_3$C), 130.4 (d, $^1$J$_{CH}$=157.9 Hz, C$_6$H$_3$), 129.2 (d, $^1$J$_{CH}$=159.6 Hz, Ph), 127.1 (d, $^1$J$_{CH}$=159.6 Hz, Ph), 124.8 (d, $^1$J$_{CH}$=159.6 Hz, Ph), 123.9 (d, $^1$J$_{CH}$=154.4 Hz, C$_6$H$_3$), 69.55 (t, $^1$J$_{CH}$=147.4 Hz, α-THF), 39.0 (dt, $^1$J$_{YC}$=40.3 Hz, $^1$J$_{CH}$=101.8 Hz, YCH$_2$SiMe$_3$), 28.6 (d, $^1$J$_{CH}$=128.1 Hz, CHMe$_2$), 25.8 (q, $^1$J$_{CH}$=126.3 Hz, CHMe$_2$), 25.3 (t, $^1$J$_{CH}$=124.4 Hz, β-THF), 23.5 (q, $^1$J$_{CH}$=126.3 Hz, CHMe$_2$), 4.3 (q, J$_{CH}$=115.8 Hz, YCH$_2$SiMe$_3$).

Anal. [C$_{47}$H$_{77}$N$_2$O$_2$Si$_2$Y] (847.21) calcd: C, 66.63; H, 9.16; N, 3.31; Y, 10.49. Found: C, 66.50; H, 8.83; N, 3.29; Y, 11.28.

Example 13

Synthesis of [C$_6$F$_5$C(N-2,6-Pr$^i_2$C$_6$H$_3$)$_2$]Y(CH$_2$SiMe$_3$)$_2$(THF)$_2$ A solution of (Me$_3$SiCH$_2$)$_3$Y(THF)$_2$ (0.27 g, 0.54 mmol) in pentane (30 ml) was reacted with [C$_6$F$_5$C(N-2,6-Pr$^i_2$C$_6$H$_3$)$_2$]H (0.29 g, 0.54 mmol) at room temperature. The reaction mixture was stirred for 3 hours, after which the volume of the solution was reduced to 10 ml. Cooling to −30° C. gave the product (0.32 g, 0.35 mmol, 65%).

$^1$H NMR (300 MHz, C$_6$D$_6$, δ): 7.02–6.90 (m, 6H, C$_6$H$_3$), 3.53 (sept, $^3$J$_{HH}$=6.6 Hz, 4H, CHMe$_2$), 3.51 (m, 8H α-THF), 1.29 (d, $^3$J$_{HH}$=6.6 Hz, 12H, CHMe$_2$), 1.16 (d, $^3$J$_{HH}$=6.6 Hz, 12H, CHMe$_2$), 1.10 (m, 8H β-THF), 0.24 (s, 18H, CH$_2$SiMe$_3$), −0.05 (d, $^2$J$_{YH}$=3.3 Hz, 4H, CH$_2$SiMe$_3$). $^{19}$F NMR (188.15 MHz, 20° C., C$_6$D$_6$) δ: −132.9 (d, $^3$J$_{FF}$=19.19 Hz, o-CF), −151.8 (t, $^3$J$_{FF}$=21.26 Hz, p-CF), −162.7 (d, $^3$J$_{FF}$=17.43 Hz, m-CF).

Example 14

Ethylene Polymerization with [ArC(N-2,6-Pr$^i_2$C$_6$H$_3$)$_2$]Y(CH$_2$SiMe$_3$)$_2$(THF)$_2$ (Ar=C$_6$H$_5$, C$_6$F$_5$) with [HNMe$_2$Ph][B(C$_6$F$_5$)$_4$] Activator Following the general procedure described in example 4, for each dialkyl complex two experiments were performed (at 50° C. and 80° C. reactor temperature), as shown in Table 4. Polyethylene could be recovered from none of the experiments, and no reaction exotherm was observed.

TABLE 4

Ethylene polymerization with [ArC(N-2,6-Pr$^i_2$C$_6$H$_3$)$_2$]Y(CH$_2$SiMe$_3$)$_2$(THF)$_2$ (Ar = C$_6$H$_5$, C$_6$F$_5$) with [HNMe$_2$Ph][B(C$_6$F$_5$)$_4$] activator.

| Compound (Ar =) | Temp (° C.) | PE (g) | Productivity (kg mol$^{-1}$h$^{-1}$) |
|---|---|---|---|
| C$_6$H$_5$ | 50 | 0.0 | 0.0 |
| C$_6$H$_5$ | 80 | 0.0 | 0.0 |
| C$_6$F$_5$ | 50 | 0.0 | 0.0 |
| C$_6$F$_5$ | 80 | 0.0 | 0.0 |

Conditions:
10 μmol catalyst, 1 equiv. of [HNMe$_2$Ph][B(C$_6$F$_5$)$_4$], Run time 10 min, 605 rpm, 170 ml toluene, 0.5 L stainless steel autoclave
Ethylene pressure 5 bar Example 15

Ethylene Polymerization with [ArC(N-2,6-Pr$^i_2$C$_6$H$_3$)$_2$]Y(CH$_2$SiMe$_3$)$_2$(THF)$_2$ (Ar=C$_6$H$_5$, C$_6$F$_5$) with [HNMe$_2$Ph][B(C$_6$F$_5$)$_4$] Activator and TIBAO In a drybox, solutions were made of [ArC(N-2,6-Pr$^i_2$C$_6$H$_3$)$_2$]Y(CH$_2$SiMe$_3$)$_2$(THF)$_2$ (for Ar=C$_6$H$_5$ or C$_6$F$_5$ (10 μmol) in 10 ml toluene, solid [HNMe$_2$Ph][B(C$_6$F$_5$)$_4$] (10 μmol) and TiBAO (100 μmol) were mixed together in 10 ml toluene. Each solution was prepared in a vial sealed with a serum cap. Ethylene polymerization was performed in a stainless steel 1.0 L autoclave, pre-dried and flushed with nitrogen, charged with 200 ml of dry toluene, equilibrated at the desired reaction temperature, and pressurized with ethylene (5 bar). The solution of [HNMe$_2$Ph][B(C$_6$F$_5$)$_4$]/TiBAO was injected first into the reactor (using a pneumatically operated injector), then the solution of [ArC(N-2,6-Pr$^i_2$C$_6$H$_3$)$_2$]Y(CH$_2$SiMe$_3$)$_2$(THF)$_2$ (for Ar=C$_6$H$_5$ or C$_6$F$_5$) was added. The ethylene pressure was kept constant during the reaction by providing a replenishing flow. The reactor was stirred for 5 or 20 minutes, after which the reactor was vented. The polymer was rinsed repeatedly with methanol and subsequently dried in a vacuum oven. The results of the polymerization experiments are summarized in Table 5.

TABLE 5

Ethylene polymerization with [ArC(N-2,6-Pr$^i_2$C$_6$H$_3$)$_2$]Y(CH$_2$SiMe$_3$)$_2$(THF)$_2$ (Ar = C$_6$H$_5$, C$_6$F$_5$) with [HNMe$_2$Ph][B(C$_6$F$_5$)$_4$] activator and TIBAO.

| Compound (Ar =) | Run Time (min) | PE (g) | Productivity (kg mol$^{-1}$ bar$^{-1}$h$^{-1}$) | M$_w$ | M$_w$/M$_n$ |
|---|---|---|---|---|---|
| C$_6$H$_5$ | 20 | 18.91 | 1146 | 688500[a] | 2.05[a] |
| C$_6$H$_5$ | 5 | 11.10 | 2665 | 361400[a] | 1.89[a] |
| C$_6$F$_5$ | 20 | 20.66 | 1252 | 213800[a] | 2.48[a] |
|  |  |  |  | 265354[c] | 3.39[c] |
| C$_6$F$_5$ | 5 | 11.15 | 2677 | 185200[a] | 2.35[a] |
|  |  |  |  | 193656[c] | 2.01[c] |

Conditions:
10 μmol catalyst, 1 equiv. of [HNMe$_2$Ph][B(C$_6$F$_5$)$_4$], 10 equiv. of TiBAO, Temperature 50° C., ethylene pressure 5 bar
605 rpm, 220 ml toluene, 1.0 L stainless steel autoclave
[a,c]GPC analysis techniques as described in the general section.

Example 16

Synthesis of [PhC(N-2,6-Pr$^i_2$C$_6$H$_3$)$_2$]La(CH$_2$SiMe$_3$)$_2$(THF)$_2$

Solid LiCH$_2$SiMe$_3$ (0.85 g, 9.00 mmol) was added to a suspension of LaBr$_3$(THF)$_4$ (2.00 g, 3.00 mmol) in THF (100 ml, ambient temperature). Within 5 minutes a colorless solution formed. The solution was stirred overnight; after which, it was reacted with [PhC(N-2,6-Pr$^i_2$C$_6$H$_3$)$_2$]H (1.30 g, 3.20 mmol). The resulting yellowish solution was stirred for three hours after which the volatiles were removed under vacuum. Residual THF was removed from the solids by stirring with pentane (5 ml), which was subsequently removed under vacuum. The mixture was extracted with pentane (4×50 ml). The obtained extract was concentrated to 20 ml and cooled (−30° C.), yielding the product (0.90 g, 33%).

$^1$H NMR (500 MHz, C$_6$D$_6$, δ): 7.11 (d, $^3$J$_{HH}$=7.5 Hz, 2H, C$_6$H$_3$), 6.98 (m, 5H, Ph), 6.65 (d, $^3$J$_{HH}$=6.5 Hz, 4H, C$_6$H$_3$), 3.65 (m, 8H α-THF), 3.66 (hept, $^3$J$_{HH}$=6.5 Hz, 4H, CHMe$_2$), 1.36 (d, $^3$J$_{HH}$=6.5 Hz, 12H, CHMe$_2$), 1.30 (m, 8H β-THF), 1.02 (d, $^3$J$_{HH}$=6.5 Hz, 12H, CHMe$_2$), 0.30 (s, 18H, CH$_2$SiMe$_3$), −0.34 (s, 4H, CH$_2$SiMe$_3$).

$^{13}$C NMR (125.7 MHz, C$_6$D$_6$, δ): 171.7 (NCN), 145.0 (Ph ipso-C), 141.8 (C$_6$H$_3$ ipso-C), 133.4 (C$_6$H$_3$ C), 130.3 (d, $^1$J$_{CH}$=159.5 Hz, C$_6$H$_3$), 128.6 (d, $^1$J$_{CH}$=157.9 Hz, Ph), 126.9 (d, $^1$J$_{CH}$=159.6 Hz, Ph), 124.1 (d, $^1$J$_{CH}$=159.6 Hz, Ph), 123.8 (d, $^1$J$_{CH}$=152.6 Hz, C$_6$H$_3$), 69.4 (t, $^1$J$_{CH}$=147.3 Hz, α-THF), 56.1 (t, $^1$J$_{CH}$=103.6 Hz, LaCH$_2$SiMe$_3$), 28.6 (d, $^1$J$_{CH}$=126.3

Hz, CHMe$_2$), 25.5 (q, $^1J_{CH}$=124.6 Hz, CHMe$_2$), 25.3 (t, $^1J_{CH}$=135.1 Hz, β-THF), 23.5 (q, $^1J_{CH}$=126.2 Hz, CHMe$_2$), 4.8 (q, J$_{CH}$=115.8 Hz, LaCH$_2$SiMe$_3$).

Anal. [C$_{47}$H$_{77}$N$_2$O$_2$Si$_2$La] (897.21) calcd: C, 62.93; H, 8.65; N, 3.12; La, 15.49. Found: C, 62.39 H, 8.66; N, 3.07; La, 15.33

Example 17

Synthesis of [PhC(N-2,6-Pr$^i_2$C$_6$H$_3$)$_2$]Nd(CH$_2$SiMe$_3$)$_2$(THF)$_2$

Solid LiCH$_2$SiMe$_3$ (0.90 g, 9.60 mmol) was added to a suspension of NdCl$_3$(THF)$_3$ (1.5 g, 3.20 mmol) in THF (60 ml, ambient temperature). Within 5 minutes, a bright blue solution had formed. The solution was stirred overnight, after which, [PhC(N2,6-Pr$^i_2$C$_6$H$_3$)$_2$]H (1.45 g, 3.20 mmol) was added. The resulting blue solution was stirred for three hours. Then the volatiles were removed under vacuum. Residual THF was removed from the solids by stirring with pentane (5 ml), which was subsequently removed under vacuum. The mixture was extracted with pentane (4×50 ml). The obtained blue extract was concentrated to 20 ml and cooled (−30° C.), yielding the product (1.40 g, 49%). The identity of the product was corroborated by single crystal X-ray diffraction.

$^{13}$C NMR (125.7 MHz, C$_6$D$_6$, δ): 174.6 (NCN), 149.8 (Ph ipso-C), 148.0 (C$_6$H$_3$ ipso-C), 143.9 (C$_6$H$_3$C), 135.6 (d, $^1J_{CH}$=156.1 Hz, C$_6$H$_3$), 131.6 (d, $^1J_{CH}$=157.9 Hz, Ph), 129.1 (d, $^1J_{CH}$=154.4 Hz, Ph), 127.2 (d, $^1J_{CH}$=161.4 Hz, Ph), 114.9 (d, $^1J_{CH}$=152.6 Hz, C$_6$H$_3$), 36.3 (br, α-THF), (NdCH$_2$SiMe$_3$ could not be detected), 32.1(q, $^1J_{CH}$=115.8 Hz, NdCH$_2$SiMe$_3$), 27.3 (q, J$_{CH}$=126.32 Hz, CHMe$_2$), 21.0 (d, $^1J_{CH}$=129.8 Hz, CHMe$_2$), 17.5 (t, $^1J_{CH}$=133.4 Hz, β-THF), 23.0 (q, $^1J_{CH}$=128.08 Hz, CHMe$_2$).

Anal. [C$_{47}$H$_{77}$N$_2$O$_2$Si$_2$Nd] (902.55) calcd: C, 62.55; H, 8.60; N, 3.10. Found: C, 61.53; H, 8.48; N, 3.04.

Example 18

Ethylene Polymerization with [{PhC(N-2,6-Pr$^i_2$C$_6$H$_3$)$_2$}M(CH$_2$SiMe$_3$)$_2$(THF)$_2$ (M=La, Nd) and [HNMe$_2$Ph][B(C$_6$F$_5$)$_4$]

Ethylene polymerization experiments were performed following the general procedure described in example 4, as shown in table 6.

TABLE 6

Ethylene polymerization with
[{PhC(N-2,6-Pr$^i_2$C$_6$H$_3$)$_2$}M(CH$_2$SiMe$_3$)$_2$(THF)$_2$ (M = La, Nd) and [HNMe$_2$Ph][B(C$_6$F$_5$)$_4$].

| Compound (M =) | PE (g) | Productivity (kg mol$^{-1}$bar$^{-1}$h$^{-1}$) | M$_w$ | M$_w$/M$_n$ |
|---|---|---|---|---|
| La | 0.0 | 0.0 | | |
| Nd | 0.20 | 25.0 | 301000[b] | 1.75[b] |

Conditions:
10 μmol catalyst, 1 equiv. of [HNMe$_2$Ph][B(C$_6$F$_5$)$_4$], 605 rpm, Temp 50° C.
Ethylene pressure 5 bar
150 ml toluene
Time 10 min
0.5 L stainless steel autoclave
[b]GPC analysis techniques as described in the general section.

Example 19

Ethylene Polymerization with [{PhC(N2,6-Pr$^i_2$C$_6$H$_3$)$_2$}M(CH$_2$SiMe$_3$)$_2$(THF) (M=La, Nd), [HNMe$_2$Ph][B(C$_6$F$_4$)$_4$] and TIBAO Ethylene polymerization experiments were performed following the general procedure described in Example 15. The results are summarized in Table 7.

TABLE 7

Ethylene polymerization with
[{PhC(N-2,6-Pr$^i_2$C$_6$H$_3$)$_2$}M(CH$_2$SiMe$_3$)$_2$(THF)$_2$ (M = La, Nd), [HNMe$_2$Ph][B(C$_6$F$_5$)$_4$] and TIBAO.

| Compound (M =) | PE (g) | Productivity (kg mol$^{-1}$bar$^{-1}$h$^{-1}$) | Time (min) | M$_w$ | M$_w$/M$_n$ |
|---|---|---|---|---|---|
| La | 2.62 | 104 | 30 | 517000[b] | 2.17[b] |
| Nd | 18.67 | 1131 | 20 | 321600[b] | 1.99[b] |

Conditions:
10 μmol catalyst, 1 equiv. of [HNMe$_2$Ph][B(C$_6$F$_5$)$_4$], 10 equiv. of TiBAO run time 20 min, Temperature 50° C.
ethylene pressure 5 bar
605 rpm, 200 ml toluene, 1.0 L stainless steel autoclave
[b]GPC analysis techniques as described in the introduction.

While certain representative embodiments and details have been shown to illustrate the invention, it will be apparent to skilled artisans that various process and product changes from those this document discloses may be made without departing from this invention's scope.

All patents, test procedures, and other cited documents are fully incorporated by reference to the extent that this material is consistent with this specification and for all jurisdictions in which such incorporation is permitted. All documents to which priority is claimed are fully incorporated by reference for all jurisdictions in which such incorporation is permitted. Although dependent claims have single dependencies in accordance with U.S. practice, each of the features in any of the dependent claims can be combined with each of the features of one or more of the other dependent claims dependent upon the same independent claim or claims.

Certain features of the present invention are described in terms of a set of numerical upper limits and a set of numerical lower limits. It should be appreciated that ranges formed by any combination of these limits are within the scope of the invention unless otherwise indicated.

What is claimed is:

1. A composition of matter comprising the reaction product of an activator and catalyst precursor where the catalyst precursor comprises:

(a) a Group-3 or lanthanide metal;

(b) an amidinate or phosphoamidinate connected to the metal where the amidinate or phosphoamidinate comprises:

a central carbon atom connected between two nitrogen atoms, two phosphorus atoms, or one nitrogen and one phosphorus atom;

an adjuvant moiety connected to each nitrogen or phosphorus atom, respectively, where the adjuvant moiety comprises:

two first R-groups, where the first R-groups are independently C$_1$–C$_{30}$ hydrocarbyl radicals or selected from the group consisting of trifluoromethyl, 2,6-dichlorophenyl, fluoro, chloro, bromo, methoxy, or dimethylamino radicals;

an aryl group connected to both of the first R-groups where each first R-group connects to the aryl group at a position adjacent to the adjuvant moiety nitrogen or adjuvant moiety phosphorus connection; and at least one second R-group where the second R-group is independently hydrogen or a C$_1$–C$_{30}$ hydrocarbyl radical or selected from the group consisting of trifluoromethyl, 2,6-dichlorophenyl, fluoro, chloro, bromo, methoxy, or dimethylamino radicals;
an apical substituent that connects to the central carbon atom where the apical substituent is selected from $C_1$–$C_{30}$ hydrocarbyl radicals;
(c) 0, 1, or 2 Lewis bases connected to the metal;
(d) a ligand abstractable by an activator; and
(e) a ligand in which an olefin can insert between it and the metal.

2. The composition of matter of claim 1 where the first R-groups are independently methyl, ethyl, propyl, cyclohexyl, phenyl, butyl, 2,2-dimethylethyl, dimethylphenylmethyl, or methyldiphenylmethyl, radicals.

3. The composition of matter of claim 1 where the second R-group is independently a hydrogen, methyl, ethyl, propyl, cyclohexyl, phenyl, butyl, 2,2-dimethylethyl, dimethylphenylmethyl, or methyldiphenylmethyl, radical.

4. A composition of matter comprising the reaction product of an activator and catalyst precursor where the catalyst precursor has the following formula:

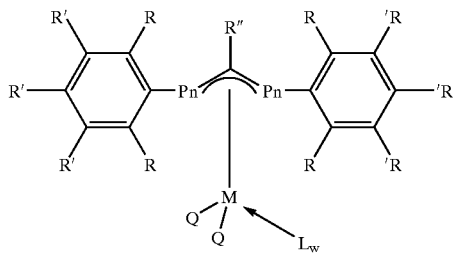

where
(a) M is a Group-3 or lanthanide metal;
(b) Pn, R, R', and R" are part of an amidinate ligand (both Pn=nitrogen) or a phosphoamidinate (one or more Pn=phosphorus) where
  R is a first R-group independently selected from $C_1$–$C_{30}$ hydrocarbyl radicals or selected from the group consisting of trifluoromethyl, 2,6-dichlorophenyl, fluoro, chloro, bromo, methoxy, or dimethylamino radicals;
  R' is a second R-group independently selected from hydrogen or $C_1$–$C_{30}$ hydrocarbyl radicals or selected from the group consisting of trifluoromethyl, 2,6-dichlorophenyl, fluoro, chloro, bromo, methoxy, or dimethylamino radicals;
  R" is an apical substituent independently selected from $C_1$–$C_{30}$ hydrocarbyl radicals;
(c) Q is a ligand abstractable by an activator or a ligand in which an olefin can insert between it and the metal;
(d) L is an optional Lewis base; and
(e) w=0, 1, or 2.

5. The composition of matter of claim 4 where the first R-groups are independently methyl, ethyl, propyl, cyclohexyl, phenyl, butyl, 2,2-dimethylethyl, dimethylphenylmethyl, or methyldiphenylmethyl, radicals.

6. The composition of matter of claim 4 where the second R-groups are independently hydrogen, methyl, ethyl, propyl, cyclohexyl, phenyl, butyl, 2,2-dimethylethyl, dimethylphenylmethyl, or methyldiphenylmethyl, radicals.

7. A composition of matter comprising an activator and a catalyst precursor where the catalyst precursor comprises:
(a) a Group-3 or lanthanide metal;
(b) an amidinate (comprising two nitrogen atoms) or phosphoamidinate (comprising two phosphorus atoms or one nitrogen and one phosphorus atom) connected to the metal where the amidinate or phosphoamidinate comprises:
  a central carbon atom connected between two nitrogen atoms, two phosphorus atoms, or one nitrogen and one phosphorus atom;
  an adjuvant moiety connected to each nitrogen or phosphorus atom, respectively, where the adjuvant moiety comprises:
    two first R-groups where the side groups are independently $C_1$–$C_{30}$ hydrocarbyl radicals or selected from the group consisting of trifluoromethyl, 2,6-dichlorophenyl, fluoro, chloro, bromo, methoxy, or dimethylamino radicals;
    an aryl group connected to both of the first R-groups where each first R-group connects to the aryl group at a position adjacent to the adjuvant moiety nitrogen or adjuvant moiety phosphorus connection; and
    at least one second R-group where the second R-group is independently hydrogen, or $C_1$–$C_{30}$ hydrocarbyl radicals or selected from the group consisting of trifluoromethyl, 2,6-dichlorophenyl, fluoro, chloro, bromo, methoxy, or dimethylamino radicals;
  an apical substituent that connects to the central carbon atom where the apical substituent is a $C_1$–$C_{30}$ hydrocarbyl radical;
(c) 0, 1, or 2 Lewis bases connected to the metal;
(d) a ligand abstractable by an activator; and
(e) a ligand in which an olefin can insert between it and the metal.

8. The composition of matter of claim 7 where the first R-groups are methyl, ethyl, propyl, cyclohexyl, phenyl, butyl, 2,2-dimethylethyl, dimethylphenylmethyl, or methyldiphenylmethyl radicals.

9. The composition of matter of claim 7 where the second R-groups are independently hydrogen, methyl, ethyl, propyl, cyclohexyl, phenyl, butyl, 2,2-dimethylethyl, dimethylphenylmethyl, or methyldiphenylmethyl, radicals.

10. A composition of matter comprising an activator and a catalyst precursor where the catalyst precursor has the following formula:

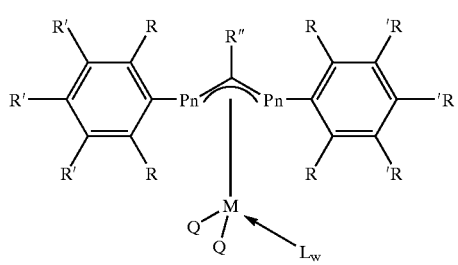

where
(a) M is a Group-3 or lanthanide metal;
(b) Pn, R, R', and R" are part of an amidinate ligand (both Pn=nitrogen) or a phosphoamidinate (one or more Pn=phosphorus) where
  R is a first R-group independently selected from $C_1$–$C_{30}$ hydrocarbyl radicals or selected from the group consisting of trifluoromethyl, 2,6-dichlorophenyl, fluoro, chloro, bromo, methoxy, or dimethylamino radicals;

R' is a second R-group independently selected from hydrogen or $C_1$–$C_{30}$ hydrocarbyl radicals or selected from the group consisting of trifluoromethyl, 2,6-dichlorophenyl, fluoro, chloro, bromo, methoxy, or dimethylamino radicals;

R" is an apical substituent independently selected from $C_1$–$C_{30}$ hydrocarbyl radicals;

(c) Q is a ligand abstractable by an activator or a ligand in which an olefin can insert between it and the metal;

(d) L is an optional Lewis base; and (e) w=0, 1, or 2.

11. The composition of matter of claim 10 where the first R-groups are independently methyl, ethyl, propyl, cyclohexyl, phenyl, butyl, 2,2-dimethylethyl, dimethylphenylmethyl, or methyldiphenylmethyl, radicals.

12. The composition of matter of claim 10 where the second R-groups are independently hydrogen, methyl, ethyl, propyl, cyclohexyl, phenyl, butyl, 2,2-dimethylethyl, dimethylphenylmethyl, or methyldiphenylmethyl, radicals.

13. The composition of claims 1, 4, 7 or 10 where each first R-group is an isopropyl radical.

14. The composition of claims 1, 4, 7, or 10 where the apical substituent is phenyl or perfluorophenyl.

15. The composition of claims 1, 4, 7, or 10 where the metal is a lanthanide.

16. The composition of claim 15 where the metal is neodymium.

17. The composition of claims 1, 4, 7, or 10 where the metal is a Group-3 transition metal.

18. The composition of claim 17 where the metal is yttrium.

19. The composition of claims 1, 4, 7, or 10 where the ligand abstractable by an activator is a radical independently selected from hydride, halide, hydrocarbyl, hydrocarbylsilyl, alkoxide, aryloxide, amide, or phosphide radicals.

20. The composition of claim 19 where the ligand abstractable by an activator is independently selected from 3-methylpentyl, butoxy, butyl, dimethylamido, 3,6-dimethylphenoxy, dimethylphosphido, diphenylamido, diphenylphosphido, ethoxy, ethyl(triethylsilyl), ethyl (trimethylsilyl), ethylpentylphosphido, heptyl, hexoxy, hexyl, isohexyl, isopentoxy, isopentyl, isopropoxy, isopropyl, methoxy, methyl(triethylsilyl), methyl (trimethylsilyl), methylethylamido, 2-methy-4-ethylphenoxy, methylethylphosphido, methylnonylphosphido, methylpropylamido, methylpropylphosphido, octyl, pentoxy, pentyl, phenoxy, phenylethylamido, phenylethylphosphido, propoxy, propyl, t-butoxy, or t-butyl.

21. The composition of claim 20 where the ligand abstractable by an activator is independently selected from methyl(triethylsilyl), methyl(trimethylsilyl), phenyl, neopentyl, or benzyl.

22. The composition of claims 1, 4, 7, or 10 where the ligand in which an olefin can insert between it and the metal is independently a hydride, halide, hydrocarbyl, hydrocarbylsilyl, alkoxide, aryloxide, amide, or phosphide radical.

23. The composition of claim 22 where the ligand in which an olefin can insert is independently selected from 3-methylpentyl, butoxy, butyl, dimethylamido, 3,6-dimethylphenoxy, dimethyl-phosphido, diphenylamido, diphenylphosphido, ethoxy, ethyl(triethylsilyl), ethyl (trimethylsilyl), ethylpentylphosphido, heptyl, hexoxy, hexyl, isohexyl, iso-pentoxy, isopentyl, isopropoxy, isopropyl, methoxy, methyl(triethylsilyl), methyl (trimethylsilyl), methylethylamido, 2-methy-4-ethylphenoxy, methylethylphosphido, methylnonylphosphido, methylpropylamido, methylpropylphosphido, octyl, pentoxy, pentyl, phenoxy, phenylethylamido, phenylethylphosphido, propoxy, propyl, t-butoxy, or t-butyl.

24. The composition of claim 23 where the ligand in which an olefin can insert between it and the metal is independently selected from methyl(triethylsilyl), methyl(trimethylsilyl), phenyl, neopentyl, or benzyl.

25. The composition of claims 1 or 10 where
   (a) the Group-3 or lanthanide metal is yttrium;
   (b) the apical substituent is one phenyl or perfluorophenyl radical;
   (c) one adjuvant moiety is connected to each nitrogen atom of the amidinate where each adjuvant moiety consists of a 2,6-diisopropyl-phenyl radical;
   (d) the Lewis base is one tetrahydrofuran molecule;
   (e) the ligand abstractable by an activator is a methyl (trimethylsilyl) radical; and
   (f) the ligand in which an olefin can insert between it and the metal is a methyl(trimethylsilyl) radical.

26. An olefin polymerization process comprising providing the composition of matter of claims 1, 4, 7 or 10.

27. A polymer prepared by providing at least one composition of claims 1, 4, 7, or 10.

28. An article of manufacture produced using the polymer of claim 27.

29. An article of manufacture produced using the process of claim 26.

30. An article of manufacture produced using the composition of claims 1, 4, 7, or 10.

31. An olefin polymerization process comprising providing the composition of claim 25.

32. A polymer prepared by providing at least one composition of claim 25.

33. An article of manufacture produced using the composition of claim 25.

* * * * *